US007919261B2

(12) United States Patent
Fantin et al.

(10) Patent No.: US 7,919,261 B2
(45) Date of Patent: Apr. 5, 2011

(54) METHODS FOR PREDICTING TREATMENT RESPONSE BASED ON THE EXPRESSION PROFILES OF PROTEIN AND TRANSCRIPTION BIOMARKERS

(75) Inventors: Valeria R. Fantin, Cambridge, MA (US); Jacqueline W. Pierce, Wellesley, MA (US); Andrey Loboda, Philadelphia, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 246 days.

(21) Appl. No.: 12/086,102

(22) PCT Filed: Dec. 1, 2006

(86) PCT No.: PCT/US2006/046208
§ 371 (c)(1),
(2), (4) Date: Jun. 5, 2008

(87) PCT Pub. No.: WO2007/067476
PCT Pub. Date: Jun. 14, 2007

(65) Prior Publication Data
US 2009/0304594 A1  Dec. 10, 2009

(51) Int. Cl.
*G01N 33/53* (2006.01)
(52) U.S. Cl. ....................................... 435/7.1
(58) Field of Classification Search .................. None
See application file for complete search history.

(56) References Cited

OTHER PUBLICATIONS

Tockman et al (Cancer Res., 1992, 52:2711s-2718s).*
Frank et al (Cancer Treatment and Research, 2003, 115: 267-291).*
Sommer VH et al., Leukemia, vol. 18, pp. 1288-1295 (2004), "In vivo activation of STAT3 in cutaneous T-cell lymphoma. Evidence for an antiapoptotic function of STAT3".
Kari, L et al., The Journal of Experimental Medicine, vol. 197, No. 11, pp. 1477-1488 (2003), "Classification and prediction of survival in patients with the leukemic phase of cutaneous T cell lymphoma".
Alas, S et al., Clinical Cancer Research, vol. 9, pp. 316-326 (2003), "Inhibition of constitutive STAT3 activity sensitizes resistant non-hodgkin's lymphoma and multiple myeloma to chemotherapeutic drug-mediated apoptosis".
Ikuta, K et al., Oncology Reports, vol. 13, pp. 217-222 (2005), "Overexpression of constitutive signal transducer and activator of transcription 3 mRNA in cisplatin-resistant human non-small cell lung cancer cells".
Khoury, JD et al., Clinical Cancer Research, vol. 9, pp. 3692-3699 (2003), "Differential expression and clinical significance of tyrosine-phosphorylated STAT3 in ALK+ and ALK− anaplastic large cell lymphoma".
Mitchell, TJ et al., Immunology, vol. 114, pp. 301-312 (2005), "Signal transducer and activator of transcription (STAT) signalling and T-cell lymphomas".

Roberts, D et al., British Journal of Cancer, vol. 92, pp. 1149-1158 (2005), "Identification of genes associated with platinum drug sensitivity and resistance in human ovarian cancer cells".
Yu, H et al., Nature Reviews Cancer, vol. 4, pp. 97-105 (2004), "The STATS of cancer—new molecular targets come of age".
George SR et al., Nature Reviews Drug Discovery, vol. 1, pp. 808-820 (2002), "G-protein-coupled receptor oligomerization and its potential for drug discovery".
Mellado, M et al., Annual Review of Immunology, vol. 19, pp. 397-421 (2001), "Chemokine signaling and functional responses: The role of receptor dimerization and TK pathway activation".
Schlessinger, J, Cell, vol. 103, pp. 211-225 (2000), "Cell signaling by receptor tyrosine kinases".
Yarden, Y, European Journal of Cancer, vol. 37, pp. S3-S8 (2001), "The EGFR family and its ligands in human cancer: signalling mechanisms and therapeutic opportunities".
Herbst, RS et al., Cancer, vol. 94, No. 5, pp. 1593-1611 (2002), "Monoclonal antibodies to target epidermal growth factor receptor-positive tumors".
Yarden, Y et al., Nature Reviews Molecular Cell Biology, vol. 2, pp. 127-137 (2001), "Untangling the ErbB signalling network".
McCormick, F, Trends in Cell Biology, vol. 9, No. 12, pp. M53-M56 (1999), "Signalling networks that cause cancer".
Blume-Jensen, P et al., Nature, vol. 411, pp. 355-365 (2001), "Oncogenic kinase signaling".
Davie, JR, Current Opinion in Genetics & Development, vol. 8, pp. 173-178 (1998), "Covalent modifications of histones: expression from chromatin templates".
Kouzarides, T, Current Opinion in Genetics & Development, vol. 9, pp. 40-48 (1999), "Histone acetylases and deacetylases in cell proliferation".
Strahl, BD et al., Nature, vol. 403, pp. 41-45 (2000), "The language of covalent histone modifications".
Ng, HH et al., Trends in Biolochemical Sciences, vol. 25, pp. 121-126 (2000), "Histone deacetylases: silencers for hire".
Gray, SG et al., Experimental Cell Research, vol. 262, pp. 75-83 (2001), "The human histone deacetylase family".
Petricoin, EF et al., Nature Reviews Drug Discovery, vol. 1, pp. 683-695 (2002), "Clinical proteomics: Translating benchside promise into bedside reality".
Sidransky, D, Nature Reviews Cancer, vol. 2, pp. 210-219 (2002), "Emerging molecular markers of cancer".
Wargovich, MJ et al., Cancer Epidemiology, Biomarkers & Prevention, vol. 5, pp. 355-360 (1996), "Aberrant crypts as a biomarker for colon cancer: Evaluation of potential chemopreventive agents int he rat".

(Continued)

*Primary Examiner* — Sean E Aeder
(74) *Attorney, Agent, or Firm* — Li Su; David A. Muthard

(57) ABSTRACT

The invention disclosed herein describes novel biomarkers useful for risk assessment, screening, prognosis and selection and monitoring of therapy for HDAC mediated cell proliferative disorders. In particular, the invention provides the identities of three particular proteins whose expression patterns are strongly predictive of a particular patient's treatment outcome, e.g., non-responsiveness to SAHA. The expression profile, or pattern, whether embodied in nucleic acid expression, protein expression, or other expression formats will find use in identifying and selecting patients afflicted with a particular HDAC mediated cancer who are likely to be non-responsive to SAHA-based therapy and thus candidates for other treatments.

1 Claim, 7 Drawing Sheets

OTHER PUBLICATIONS deVere White, RW et al., Oncology, vol. 12, No. 12, pp. 1717-1726 (1998), "Predicting prognosis in patients with superficial bladder cancer".

Stein JP et al., The Journal of Urology, vol. 160, pp. 645-659 (1998), "Prognostic markers in bladder cancer: A comtemporary review of the literature".

Cook, AM et al., Proceedings of the American Society of Clinical Oncology, vol. 17, abstract 1199 (1998), "The utility of tumour markers in assessing the response to chemotherapy in advanced bladder cancer".

van Haaften-Day, C et al., Cancer, vol. 92, No. 11, pp. 2637-2644 (2001), "OVX1, Macrophage-colony stimulating factor, and CA-125-II as tumor markers for epithelial ovarian carcinoma, a critical appraisal".

Sambrook, J et al., Molecular Cloning: A Laboratory Manual, vol. I and II (1989).

Mullis KB et al., Methods in Enzymology, vol. 155, pp. 335-350 (1987), "Specific synthesis of DNA in vitro via a polymerase-catalyzed chain reaction".

Karlin, S et al., Proceedings of the National Academy of Sciences, vol. 87, pp. 2264-2268 (1990), "Methods for assessing the statistical significance of molecular sequence features by using general scoring schemes".

Karlin, S et al., Proceedings of the National Academy of Sciences, vol. 90, pp. 5873-5877 (1993), "Applications and statistics for multiple high-scoring segments in molecular sequences".

Myers, EW et al., CABIOS, vol. 4, No. 1, pp. 11-17 (1988), "Optimal alignments in linear space".

Bird, RE et al., Science, vol. 242, pp. 423-426 (1988), "Single-chain antigen-binding proteins".

Huston, JS et al., Proceedings of the National Academy of Sciences, vol. 85, pp. 5879-5883 (1988), "Protein engineering of antibody binding sites: Recovery of specific activity in an anti-digoxin single-chain Fv analogue produced in *Escherichia coli*".

Frank, DA, Cancer Treatment and Research, vol. 115, pp. 267-291 (2003), "STAT signaling in cancer: insights into pathogenesis and treatment strategies in signal transduction in cancer".

Bromberg, J., "Stat proteins and oncogenesis", Journal of Clinical Investigation, 109(9):1139-1142; American Socitey for Clinical Investigation; XP002269665, ISSN:0021-9738, (May 2002).

Klampfer, L. et al., "Requirement for Histone Deacetylase Activity for Signaling by STAT1", Journal of Biological Chemistry, 279(29):30358-30368;XP009127861, ISSN: 0021-9258, (Jul. 16, 2004).

Sun, W. H., et al., "Interferon-alpha Resistance in a Cutaneous T-Cell Lymphoma Cell Line is Associated with Lack of STAT1 Expression", Blood 91(2):570-576; XP009127766; ISSN: 0006-4971, (Jan. 15, 1998).

Zhang, C., et al., "Selective Induction of Apoptosis by Histone Deacetylase Inhibitor SAHA in Cutaneous T-Cell Lymphoma Cells: Relevance to Mechanism of Therapeutic Action", The Journal of Investigative Dermatology, 125(5):1045-1052;XP002563294, ISSN: 0022-202X (Nov. 2005).

\* cited by examiner

NR-Patient ID 082140

PR-Patient ID 057172

METHODS FOR PREDICTING TREATMENT RESPONSE BASED ON THE EXPRESSION PROFILES OF PROTEIN AND TRANSCRIPTION BIOMARKERS

PRIORITY CLAIM

This application is a §371 National Stage Application of PCT/US2006/046208, filed on Dec. 1, 2006, which claims priority from US Provisional Application Ser. No. 60/742,394, filed on Dec. 5, 2005.

FIELD OF THE INVENTION

The present invention relates generally to the identification of novel biomarkers, whose individual or collective expression patterns are useful for risk assessment, early detection, establishing prognosis, and evaluation of intervention.

BACKGROUND OF THE INVENTION

The interactions of cell surface membrane components play crucial roles in transmitting extracellular signals to a cell in normal physiology, and in disease conditions. Many types of cell surface receptors undergo dimerization, oligomerization, or clustering in connection with the transduction of an extracellular event or signal, e.g. ligand-receptor binding, into a cellular response, such as proliferation, increased or decreased gene expression, or the like, e.g. George et al, Nature Reviews Drug Discovery, 1: 808-820 (2002); Mellado et al, Ann. Rev. Immunol., 19: 397421 (2001); Schlessinger, Cell, 103: 211-225 (2000); Yarden, Eur. J. Cancer, 37: S3-S8 (2001). The role of such signal transduction events in diseases, such as cancer, has been the object of intense research and has led to the development of several new drugs and drug candidates, e.g. Herbst and Shin, Cancer, 94: 1593-1611 (2002); Yarden and Sliwkowski, Nature Reviews Molecular Cell Biology, 2: 127-137 (2001); McCormick, Trends in Cell Biology, 9: 53-56 (1999); Blume-Jensen and Hunter, Nature, 411: 355-365 (2001).

Many disease states are characterized by differences in the expression levels of various genes either through changes in the copy number of the genetic DNA or through changes in levels of transcription of particular genes (e.g., through control of initiation, provision of RNA precursors, RNA processing, etc.). Dynamic changes in the nucleosomal packaging of DNA must occur to allow transcriptional proteins to contact with the DNA template. One of the most important mechanisms influencing chromatin remodeling and gene transcription are the posttranslational modification of histones and other cellular proteins by acetylation and subsequent changes in chromatin structure (Davie, 1998, Curr Opin Genet Dev 8, 173-8; Kouzarides, 1999, Curr Opin Genet Dev 9, 40-8; Strahl and Allis, 2000, Nature 403, 41-4).

Histones are small, positively charged proteins which are rich in basic amino acids (positively charged at physiological pH), which contact the phosphate groups (negatively charged at physiological pH) of DNA. The majority of histones are synthesized during the S phase of the cell cycle, and newly synthesized histones quickly enter the nucleus to become associated with DNA. Within minutes of its synthesis, new DNA becomes associated with histones in nucleosomal structures.

There are five main classes of histones, H1, H2A, H2B, H3, and H4. The amino acid sequences of histones H2A, H2B, H3, and H4 show remarkable conservation between species, whereas H1 varies somewhat, and in some cases is replaced by another histone, e.g., H5. Four pairs of each of H2A, H2B, H3, and H4 together form a disk-shaped octomeric protein core, around which DNA (about 140 base pairs) is wound to form a nucleosome. Individual nucleosomes are connected by short stretches of linker DNA associated with another histone molecule (e.g., H1, or in certain cases, H5) to form a structure resembling a beaded string, which is itself arranged in a helical stack, known as a solenoid.

Briefly, acetylation neutralizes the positive charge of the lysine side chain, and is thought to impact chromatin structure. Hyperacetylation of the N-terminal tails of histones H3 and H4 correlates with gene activation whereas deacetylation can mediate transcriptional repression. When this occurs in genes critical to growth inhibition, the resulting silencing of transcription could promote tumor progression.

Specifically, in the case of histone hyperacetylation, changes in electrostatic attraction for DNA and steric hindrance introduced by the hydrophobic acetyl group leads to destabilization of the interaction of histones with DNA. As a result, acetylation of histones disrupts nucleosomes and allows the DNA to become accessible to the transcriptional machinery. Removal of the acetyl groups allows the histones to bind more tightly to DNA and to adjacent nucleosomes and thus to maintain a transcriptionally repressed chromatin structure. Consequently, STAT expression correlates with transcriptional activation, whereas histone deacetylation is associated with gene repression.

Acetylation is mediated by a series of enzymes with histone acetyltransferase (HAT) activity. Conversely, acetyl groups are removed by specific histone deacetylase (HDAC) enzymes whose deregulation is associated with several cancers. Disruption of these mechanisms gives rise to transcriptional misregulation and may lead to tumorigenic transformation. In addition, other molecules such as transcription factors alter their activity and stability depending on their acetylation status. The recruitment of histone acetyltransferases (HATs) and histone deacetylases (HDACs) is considered as a key element in the dynamic regulation of many genes playing important roles in cellular proliferation and differentiation. Defects in both HATs and HDACs have been reported in a variety of cancers. See Kouzarides, T., "Histone acetylases and deacetylases in cell proliferation," *Curr. Opin. Genet. Dev.,* 9: 40-48 (1999) for an excellent review.

A growing number of histone deacetylases (HDACs) have been identified. See, for example, Ng, H. H. and Bird, A., "Histone deacetylases: silencers for hire." *Trends Biochem. Soc.,* vol. 25:121-126 (2000). Mammalian histone deacetylases can be divided into three subclasses (see, for example, Gray and Ekstrom, Exp Cell Res, January 15; 262(2):75-83 (2001)). HDACs 1, 2, 3, and 8 which are homologues of the yeast RPD3 protein constitute class I. HDACs 4, 5, 6, 7, 9, and 10 are related to the yeast Hda 1 protein and form class II. Recently, several mammalian homologues of the yeast Sir2 protein have been identified forming a third class of deacetylases which are NAD dependent. All of these HDACs appear to exist in the cell as subunits of a plethora of multiprotein complexes. In particular, class I and II HDACs have been shown to interact with transcriptional corepressors, mainly N-CoR and SMMT, which serve as bridging factors required for the recruitment of HDACs to transcription factors.

Since histone deacetylases (HDACs) are involved in cell cycle progression and differentiation, and their deregulation is associated with several cancers, recent efforts have focused on identifying potent HDAC inhibitors (HDACi). Recently, certain compounds that induce terminal differentiation have been reported to inhibit histone deacetylases. Indeed, suberoylanilide hydroxamic acid (SAHA) is a potent inhibitor of HDACs that causes growth arrest, differentiation, and/or apoptosis of many tumor types in vitro and in vivo. Because of its low toxicity, SAHA is currently in clinical trials for the treatment of cancer. SAHA is reported to be effective in preventing the formation of mammary tumors in rats, and lung tumors in mice.

Cancer diseases account for nearly one-quarter of deaths in the United States, exceeded only by heart diseases. The disease contributes to a major financial burden to the community and to individuals. A central paradigm in the care and treatment of patients presenting with cellular proliferative disorders mediated by HDAC(HDAC+) to offer better risk assessment, screening, diagnosis, prognosis and selection and monitoring of therapy. At present, cancer patients often undergo chemotherapy and radiotherapy. However, the treatment outcome is not always satisfactory.

In the early clinical development of anti-cancer agents, clinical trials are typically designed to evaluate the safety tolerability, and pharmacokinetics, as well as to identify a suitable dose and schedule for further clinical evaluation. Scientists believe that the development of new validated intermediate end points will lead to significant reductions in healthcare and drug development costs as well as provide a tool for achieving successful preventive intervention. Increasingly, efforts are being expended towards identifying high-risk individuals who are at risk of, or susceptible to, becoming resistant to a particular therapeutic moiety or alternatively, not responding to a particular therapeutic moiety. Earlier identification of such at-risk patients would help in the development of molecular-targeted interventions to prevent or delay neoplasia. Mindful that prognosis and prediction of response are necessary for the selection of neoadjuvant or adjuvant chemotherapy, it would be useful to be able to identify clinically relevant intermediate end points, which may predict not only the final outcome of a chemopreventive trial but also help identify high-risk patients. After all, avoiding ineffective therapies is as important as identifying effective ones.

As a consequence, a great deal of effort is being directed to using new technologies to find new classes of biomarkers, which is becoming one of the highly prized targets of cancer research. See Petricoin et al, Nature Reviews Drug Discovery, 1: 683-695 (2002); Sidransky, Nature Reviews Cancer, 2: 210-219 (2002). Overall, risk biomarkers will find use not only in diagnosis but also predict response to therapy, identify potential candidates who may best be suited for a particular chemopreventive intervention, aid in the rational design of future intervention therapy. The study of biomarkers that can possibly predict how a person's disease may progress or respond to treatment, falls under the category of chemoprevention. Biomarkers used to measure a response to an intervention are called surrogate endpoint biomarkers or SEBs (Kelloff et al. Cancer Epidemiology, Biomarkers and Prev., 5: 355-360 (1996). Examples of biomarkers include genetic markers (e.g., nuclear aberrations [such as micronuclei], gene amplification, and mutation), cellular markers (e.g., differentiation markers and measures of proliferation, such as thymidine labeling index), histologic markers (e.g., premalignant lesions, such as leukoplakia and colonic polyps), and biochemical and pharmacologic markers (e.g., ornithine decarboxylase activity).

The identification of these biomarkers may be carried out by analyzing changes in specific polypeptides or mRNA, as predicted by the known biology associated with the molecule targeted by the agent of interest. Alternatively, biomarkers can be identified by analyzing global changes in polypeptides or mRNA in cells or tissues exposed to efficacious doses of the agent. Once identified, these biomarkers can be used to tailor a patient's clinical protocol such as, for example, being able to predict a patient's response to a particular treatment protocol with a particular therapeutic moiety.

Current predictive and prognostic biomarkers include DNA ploidy, S-phase, Ki-67, Her2/neu (c-erb B-2), p53, p21, the retinoblastoma (Rb) gene, MDR1, bcl-2, cell adhesion molecules, blood group antigens, tumor associated antigens, proliferating antigens, oncogenes, peptide growth factors and their receptors, tumor angiogenesis and angiogenesis inhibitors, and cell cycle regulatory proteins. Beta human chorionic gonadotropin ($\beta$-hCG), carcinoembryonic antigen, CA-125, CA 19-9, and others have been evaluated and shown to correlate with clinical response to chemotherapy. See de Vere White R. W., Stapp E, "Predicting prognosis in patients with superficial bladder cancer" Oncology(Hunting), 12(12):1717-23; discussion 1724-6 (1998); Stein J P et al., "Prognostic markers in bladder cancer: a contemporary review of the literature" J. Urol.; 160 (3 Pt 1):645-59 (1998); Cook A M et al., "The utility of tumour markers in assessing the response to chemotherapy in advanced bladder cancer" Proc. Annu. Meet. Am. Soc. Clin. Oncol., 17:1199 (1998).

In the case of cancer, molecular markers such as the level of HER2/neu, p53, BCL-2 and estrogen/progesterone receptor expression have been clearly shown to correlate with disease status and progression. This example demonstrates the value of diagnostic and prognostic markers in cancer therapy. Reports from retrospective studies have shown that multivariate predictive models combining existing tumor markers improve cancer detection. See van Haaften-Day C, Shen Y, Xu F, et al., "OVX1, macrophage-colony stimulating factor, and CA-125-II as tumor markers for epithelial ovarian carcinoma: a critical appraisal.", Cancer (Phila), 92: 2837-44, (2001).

Notwithstanding the above references, the scientific literature is innocently silent of any teachings about prognostic biomarkers useful for tailoring a therapeutic protocol involving an HDAC-inhibitor.

The present invention aims at overcoming the above deficiencies by providing clinically relevant prognostic tools that may be used to identify a patient at risk of failing a therapeutic regiment involving a particular HDAC inhibitor, e.g., SAHA. Towards this end, the present invention describes for the first time a link between STAT protein expression and/or activation status (hyper-vs. hypo-phosphorylation patterns) and clinical response to SAHA. That is, it has been demonstrated in the examples appearing hereunder that the expression profiles of at least one of STAT-1, -3 and -5, individually or collectively, is predictive of the patient's response to treatment with SAHA.

SUMMARY OF THE INVENTION

The present invention relates to the identification of novel biomarkers and their use in achieving successful preventive intervention. A broad aspect of the invention relates to the identification of specific signal transducers and activators of transcription (STAT) protein as risk biomarkers for correlating their expression patterns as potential predictors of responsiveness to treatment with a particular HDAC-inhibitor—SAHA.

In another aspect, the present invention relates to the identification and use of gene expression patterns (or profiles or "signatures") which are clinically relevant to various cancers mediated by aberrant HDAC activity. In particular, the identities of genes or gene products that are correlated with patient survival are provided.

The invention thus provides for the identification and use of gene expression patterns (or profiles or "signatures") which correlate with (and thus able to discriminate between) patients with good or poor treatment outcomes. In one embodiment, the invention provides patterns that are able to identify patients with HDAC-mediated cancers that are likely to be non-responsive to treatment with an HDAC-inhibitor from those that are responsive or likely to be responsive to an HDAC-inhibitor treatment. Responsiveness may be viewed in terms of better survival outcomes over time.

In a first aspect, the present invention provides a non-subjective means for the identification of patients with HDAC mediated cancer as likely to have a good or poor response outcome to SAHA treatment by assaying for the expression patterns disclosed herein. Thus, where subjective interpretation may have been previously used to determine the prognosis and/or treatment of such cancer patients, the present invention provides objective expression patterns, which may be used alone or in combination with subjective criteria to provide a more accurate assessment of cancer patient outcomes or expected outcomes, including responsiveness to treatment with a particular therapeutic moiety. The expression patterns of the invention thus provide a means to determine cancer prognosis.

The gene expression patterns comprise one or more than one genes/sequences capable of discriminating between cancer treatment outcomes with significant accuracy. The sequences are identified as correlating with cancer treatment outcomes such that the levels of their expression are relevant to a determination of the preferred treatment protocols for a given patient.

Gene expression patterns of the invention are identified as described below. In one example, a large sampling of the gene expression profile of a sample is obtained through quantifying the expression levels of mRNA corresponding to many genes. This profile is then analyzed to identify genes or proteins, the expressions of which are positively, or negatively, correlated, with responsiveness to treatment with SAHA. An expression profile of a subset of human proteins or genes may then be identified by the methods of the present invention as correlated with a particular outcome. The use of multiple samples increases the confidence which a gene or sequence may be believed to be correlated with a particular treatment outcome. Without sufficient confidence, it remains unpredictable whether expression of a particular gene or sequence is actually correlated with an outcome and also unpredictable whether expression of a particular gene or protein may be successfully used to identify the outcome for an HDAC mediated cancer patient (HDAC+cancer patient). In one embodiment, the HDAC mediated cancer is lymphoma. In a particular embodiment, the HDAC mediated cancer is cutaneous T cell lymphoma (cancer).

A profile of genes or gene products that are highly correlated with one outcome relative to another may be used to assay a sample from a subject afflicted with cancer to predict the likely responsiveness (or lack thereof) to SAHA in the subject from whom the sample was obtained. Such an assay may be used as part of a method to determine the therapeutic treatment for said subject based upon the cancer outcome identified.

The correlated genes may be used singly with significant accuracy or in combination to increase the ability to accurately correlate a molecular expression phenotype with a treatment outcome. This correlation is a way to molecularly provide for the determination of survival outcomes and treatment responsiveness as disclosed herein. Additional uses of the correlated gene(s)/proteins are in the classification of cells and tissues; determination of prognosis; and determination and/or alteration of therapy.

The ability to discriminate or identify a high-risk SAHA-resistant patient is conferred by the identification of expression of the individual or group of genes or proteins as relevant and not by the form of the assay used to determine the actual level of expression. An assay may utilize any identifying feature of an identified individual gene or protein as disclosed herein as long as the assay reflects, quantitatively or qualitatively, expression of the gene or protein in the "transcriptome" (the transcribed fraction of genes in a genome) or the "proteome" (the translated fraction of expressed genes in a genome). Identifying features include, but are not limited to, unique nucleic acid sequences used to encode (DNA), or express (RNA), said gene or epitopes specific to, or activities of, a protein encoded by said gene. All that is required is the identity of the gene(s)/proteins necessary to identify a potential patient at-risk of failing a SAHA-based treatment or a SAHA-resistant patient.

In one aspect, the invention provides for the identification of a gene or protein expression patterns by analyzing global, or near global, gene or protein expression from single cells or homogenous cell populations which have been dissected away from, or otherwise isolated or purified from diseased cancer cells beyond that possible by a simple biopsy. Because the expression of numerous genes and/or proteins fluctuate between cells from different patients as well as between cells from the same patient sample, multiple data from expression of individual genes and/or proteins and gene/protein expression patterns are used as reference data to generate models which in turn permit the identification of individual gene and/or protein(s), the expression of which are most highly correlated with particular treatment outcomes.

In additional embodiments, the invention provides physical and methodological means for detecting the expression of gene(s) identified by the models generated by individual expression patterns. These means may be directed to assaying one or more aspects of the DNA template(s) underlying the expression of the gene(s), of the RNA used as an intermediate to express the gene(s), or of the proteinaceous product expressed by the gene(s).

A broad aspect of the invention, there is provided a method to determine the outcome of a subject afflicted with cancer by assaying a cell containing sample from said subject for expression of one or more of the genes or protein sequences (risk biomarkers) disclosed herein as correlating with responsiveness to a SAHA based therapy.

In a second aspect, the invention provides a non-subjective means based on the expression of at least one protein, or combinations thereof, for the identification of patients presenting with cancer as likely to have a poor survival outcome following SAHA treatment. In other words, the protein expression patterns will find use in predicting which patients will have an unfavorable outcome if subjected to treatment with SAHA, "unfavorable" referring to SAHA-resistance. The herein disclosed protein biomarkers are members of the expression patterns disclosed herein which will find utility in being strongly predictive of clinical outcome pertaining to SAHA treatment.

The identified sequences, e.g., amino acid sequences of any one or more of the risk biomarkers disclosed herein may thus be used in the methods of the invention for predicting a particular patient's responsiveness to SAHA treatment via analysis of lymphoma cells in a tissue or cell containing sample from a subject. As such, the present invention provides a non-empirical means for determining SAHA responsiveness in cancer patients. This provides advantages over the use of a "wait and see" approach following treatment with SAHA.

The expression levels of the identified sequences may be used alone or in combination with other sequences capable of determining responsiveness to SAHA treatment. Preferably, the sequences of the invention are used alone or in combination with each other, such as in the format of a ratio of expression levels that can have improved predictive power over analysis based on expression of sequences corresponding to individual gene/proteins(s).

The biomarker sequences are of proteins known as "signal transducers and activators of transcription proteins (STAT). Preferred sequences are STAT-1, STAT-3 and STAT-5, including splice variants and analogs thereof. STAT-5 is intended to include both STAT-5a and STAT-5b, each of which is encoded by a different gene.

The present invention thus provides means for correlating a molecular expression phenotype with a physiological response or lack thereof to a therapeutic moiety. This correlation, in turn, provides a way to molecularly diagnose and/or determine treatment for a cancer afflicted subject. Use of the sequences to identify cells of a sample as responsive, or not, to SAHA treatment may be used to determine the choice, or alteration, of therapy used to treat such cells in the subject, as well as the subject itself, from which the sample originated.

An assay of the invention may utilize a means related to the expression level of the sequences disclosed herein as long as the assay reflects, quantitatively or qualitatively, expression of the sequence. Preferably, however, a quantitative assay means is preferred. The ability to determine SAHA responsiveness and thus outcome of treatment therewith is provided by the recognition of the relevancy of the level of expression of the identified sequences and not by the form of the assay used to determine the actual level of expression. Identifying features of the sequences include, but are not limited to, unique nucleic acid sequences used to encode (DNA), or express (RNA), the disclosed sequences or epitopes specific to, or activities of, proteins encoded by the sequences. Alternative means include detection of nucleic acid amplification as indicative of increased expression levels (STAT -1, -3 or -5 sequences) or protein expression levels or STAT phosphorylation as indicative of increased or decreased expression levels. Stated differently, the invention may be practiced by assaying one or more aspect of the DNA template(s) underlying the expression of the disclosed sequence(s), of the RNA used as an intermediate to express the sequence(s), or of the proteinaceous product expressed by the sequence(s). As such, the detection of the amount of, stability of, or degradation (including rate) of, such DNA, RNA and proteinaceous molecules may be used in the practice of the invention.

The practice of the present invention is unaffected by the presence of minor mismatches between the disclosed sequences and those expressed by cells of a subject's sample. A non-limiting example of the existence of such mismatches are seen in cases of sequence polymorphisms between individuals of a species, such as individual human patients within Homo sapiens. Knowledge that expression of the disclosed sequences (and sequences that vary due to minor mismatches) is correlated with the presence of non-normal or abnormal cells and cancer is sufficient for the practice of the invention with an appropriate cell containing sample via an assay for expression.

An embodiment of the invention thus provides for the identification of the expression levels of the disclosed sequences by analysis of their expression in a sample of diseased cells. In one preferred embodiment, the sample contains single cells or homogenous cell populations which have been dissected away from, or otherwise isolated or purified from cancer cells beyond that possible by a simple biopsy. Alternatively, un-dissected cells within a "section" of tissue may be used. Multiple means for such analysis are available, including detection of expression within an assay for global, or near global, gene expression in a sample (e.g. as part of a gene expression profiling analysis such as on a microarray) or by specific detection, such as quantitative PCR (Q-PCR), or real time quantitative PCR, Western blot or translocation assays in the case of detecting phosphorylated STAT.

The present invention also provides a method for predicting patient prognosis comprising the step of analyzing the level of expression of one or more of the biomarkers of the invention, wherein the expression profile of the biomarker in normal and patient samples are analyzed, and a variation in the expression level of the biomarker in the patient sample is prognostic/predictive of whether the patient is likely to succeed in a SAHA-based therapy. The patient samples include, but are not limited to, blood, amniotic fluid, plasma, semen, bone marrow, and tissue biopsy.

The invention also provides methods for determining or predicting whether an individual requiring therapy for a disease state or disorder such as cancer will or will not respond to treatment, prior to administration of the treatment, wherein the treatment comprises one or more agents that modulate HDAC activity. The one or more agents that modulate HDAC activity can be small molecules or biological molecules. In one aspect, the agent is a small molecule that inhibits HDAC activity.

Generally, the sequences of three of the proteins or genes encoding these proteins e.g., the preferred biomarkers of the invention display increased expression in cancer cells that are unresponsive to SAHA treatment (and by definition decreased expression in responsive cases). In other instances, one may analyze the activated form of any one or more of the STAT proteins disclosed herein, e.g., analyzing the phosphorylation status of a STAT protein. Hyper-phosphorylation is indicative that the STAT proteins have been activated in response to an external stimulus. An increase expression generally refers to at least a 2 fold increase over the control or normal cells.

In one embodiment of the present invention, the biomarkers comprise one or more STAT proteins that demonstrate altered expression relative to control, such that it is predictive of identifying a patient who is likely to be non-responsive to treatment with an HDAC-inhibitor, e.g., SAHA. Preferably, the STAT is one of STAT-1, -3 or -5.

In a broad aspect, the invention provides a method for determining whether a cancer patient will respond therapeutically to a method of treating cancer comprising administering an agent that modulates HDAC activity. The method proposes analyzing the expression profile of at least one or more of the biomarkers disclosed herein in a cancerous or diseased tissue and comparing the same to the expression profile of the same protein(s) in a control population, wherein an increase in the expression profile in the diseased tissue sample is predicative of the patient's response to the HDAC modulating agent. In the methods of the invention, the gene expression profiles may be embodied in nucleic acid expression, protein expression, or other expression formats, each or all of which, may be used to predict survival of subjects afflicted with cancer and the likelihood of responsiveness to treatment with an HDAC-inhibitor.

In one aspect of the invention, the method of the invention comprises use of a biomarker selected from the group consisting of STAT-1, -3 or -5. The level of the at least one biomarker can be, for example, be the level of expression of the protein and/or the mRNA transcript of the protein.

Alternatively, expression includes determining the phosphorylation status of at least one of the three STAT proteins disclosed herein, wherein a hyper-phosphorylation status is indicative that the patient is at risk of not responding to a treatment regiment comprising SAHA. Preferably, the analysis comprises determining the collective expression of all three proteins. Preferably, the HDAC inhibitor is SAHA.

As used herein, "response" or "responding" includes, for example, a biological response (e.g., a cellular response) or a clinical response (e.g., improved symptoms, a therapeutic effect, or an adverse event) in the mammal.

The invention also provides a method for determining whether a cancer patient should continue treatment with an HDAC modulator or predict a patient's clinical outcome wherein the patient is already in a HDAC inhibitor treatment protocol. This method proposes measuring in a cancerous tissue the level of at least one or more STAT proteins over a period of time, wherein an increase in the level of the at least one biomarker compared to the level of the same protein in another patient undergoing the same treatment indicates that the patient with increased levels of at least one STAT protein is likely to not to respond favorably to further treatment with the HDAC inhibitor. Consequently, the above method enables one to identify a patient currently undergoing cancer treatment with an HDAC-inhibitor who may be at risk of developing resistance to the HDAC-inhibitor.

The invention also provides a method for treating a cancer patient with an anti-cancer agent. According to this method, a high-risk patient identified according to the methods of the invention may be exposed to a STAT reducing agent in an amount sufficient to reduce either STAT expression or activation, followed by treatment with the anti-cancer agent that modulates HDAC activity. Within this context, a decrease in the levels of expression of STAT in said patient following treatment with a STAT modulating agent indicates that the patient will likely respond therapeutically to a method of treating cancer by subsequently, exposing the patient to SAHA.

In yet another aspect, the present invention relates to a method of identifying an agent that can modulate STAT phosphorylation. The method involves exposing a group of cells that express hyper-phosphorylated STAT to a test agent and comparing the phosphorylation status of STAT in the cells to that of control cells wherein a difference in the phosphorylation status of STAT indicates that the agent can modulate STAT phosphorylation.

In still another aspect, the present invention relates to a method of determining prognosis of a HDAC-mediated cancer patient by analyzing phosphorylation status of STAT in a particular diseased or cancerous tissue or cells of the patient wherein hyper-phosphorylation status indicates a poor clinical course and hypo-phosphorylation status indicates a more favorable clinical course.

The invention also provides screening assays for determining if a patient will be susceptible or resistant to treatment with one or more agents that modulate HDAC activity.

Another aspect of the present invention is a method for detecting if a diseased status is not likely to respond therapeutically to treatment with an anti-cancer agent, comprising the step of analyzing the level of expression of one or more biomarkers, wherein the expression profile level of at least one of the biomarkers of the invention in normal and disease tissues are analyzed, and a variation in the expression level of at least one biomarker, preferably all three biomarkers, is indicative of a disease status likely to be resistant to a particular anti-cancer therapy.

In another embodiment, the invention pertains to a method of determining the phenotype of cells comprising detecting the differential expression, relative to normal cells, of at least one biomarker of the invention, wherein the expression of at least one biomarker is differentially expressed by at least a factor of two, at least a factor of five, at least a factor of twenty, or at least a factor of fifty.

In another aspect, the invention provides a kit for predicting treatment outcome or evaluating the treatment outcome of an anti-cancer agent in a patient, comprising one or more biomarkers of the invention. This aspect contemplates a kit comprising a pair of primers for amplification or a probe for hybridization of cDNA of a nucleic acid encoding any one or more polypeptide biomarkers of the invention, e.g., STAT-1, STAT-3, STAT-5 in a biological sample obtained from said patient; and an instructional material for use of the primers or the probe to determine the presence or the absence of the cDNA in the biological sample.

In another aspect, the invention provides a kit for predicting treatment outcome or evaluating the treatment outcome of an anti-cancer agent in a patient, comprising one or more antibodies having binding specificity to at least one or more of the polypeptide biomarkers of the invention in the biological sample from the subject; and an instructional material for use of the antibody(s) to determine the presence or the absence of the polypeptide biomarker in the biological sample.

Another aspect of the invention encompasses a method for predicting the treatment outcome of an anticancer agent in a subject suffering from a HDAC mediated tumor, comprising: obtaining a biological sample (diseased) from a patient; and detecting the cDNA of a nucleic acid encoding any one or more of the polypeptide biomarkers defined herein in the sample, wherein an increase in the expression of the cDNA in the sample relative to a normal or control sample predicts that the patient is at risk of non-responsiveness to treatment with an HDACi such as SAHA.

Another embodiment proposes a similar assay, the proceeding assay, except that the treatment outcome prediction relies on an increased expression of any one or more of the polypeptide biomarkers of the invention relative to a control or normal sample. However, the analysis of expression is based not on the levels of cDNA or mRNA encoding any one or more of the STAT proteins disclosed (Southern or Northern Blot) but instead on determining expression levels of the polypeptides corresponding to any one or more of STAT proteins detailed herein. The level of expression is relative to normal cells and the biomarkers of the invention are hyper-phosphorylated STAT -1, STAT-3 and/or STAT-5 relative to hypo-phosphorylated. Hyper-phosphorylated STAT proteins corresponding to one or more of STAT -1, -3 or -5 are predictive of the patient's likelihood to be SAHA-resistant.

In another aspect, the invention proposes a method of predicting treatment outcome of a cancer patient comprising analyzing in a sample of diseased cells or tissue obtained from a cancer patient the level of STAT translocation in nucleus of said cell, and comparing the same to cells in a control or normal cells, wherein an increase in the level of expression of any one or more of the polypeptide biomarkers of the invention in the nucleus of the cells in the diseased sample relative to normal or control sample is predictive of an unfavorable treatment outcome for said patient. In other words, the expression pattern predicts that the patient is likely to be SAHA-resistant and thus would not respond therapeutically to treatment with an HDACi like SAHA.

Yet another aspect of the invention is directed to a method for treating a tumor in a subject, comprising administrating an effective amount of an antibody, or a nucleic acid or a fragment thereof, as defined herein, to the subject.

Yet another aspect of the invention proposes developing a cell line expressing any one or more of the STAT protein biomarkers of the invention in order to develop a model to identify potential HDAC modulators effective to treat patient expressing higher than normal levels of any one or more of the STAT polypeptide biomarkers of the invention. The cell line may enable one to identify therapeutic moieties capable of eliciting a favorable therapeutic response from otherwise SAHA-resistant cells. Animal models following the same protocol are also envisioned by the invention.

The biological sample used in the invention is preferably selected from the group consisting of serum, plasma, and a tissue sample, but generally excludes a normal placental tissue. Those skilled in the art should understand that in the methods of the invention, the "providing a biological sample from a subject" is not a necessary feature to exploit the invention. Therefore, some embodiments of the invention may exclude this step.

While the present invention is described mainly in the context of human cancer, it may be practiced in the context of cancer, lung cancer, colon cancer or any other HDAC mediated cellular proliferative disorder that is generally responsive to treatment with an HDAC-inhibitor. Any animal known to be potentially afflicted by cancer may be used.

DETAILED DESCRIPTION OF THE INVENTION

Figure 1A:
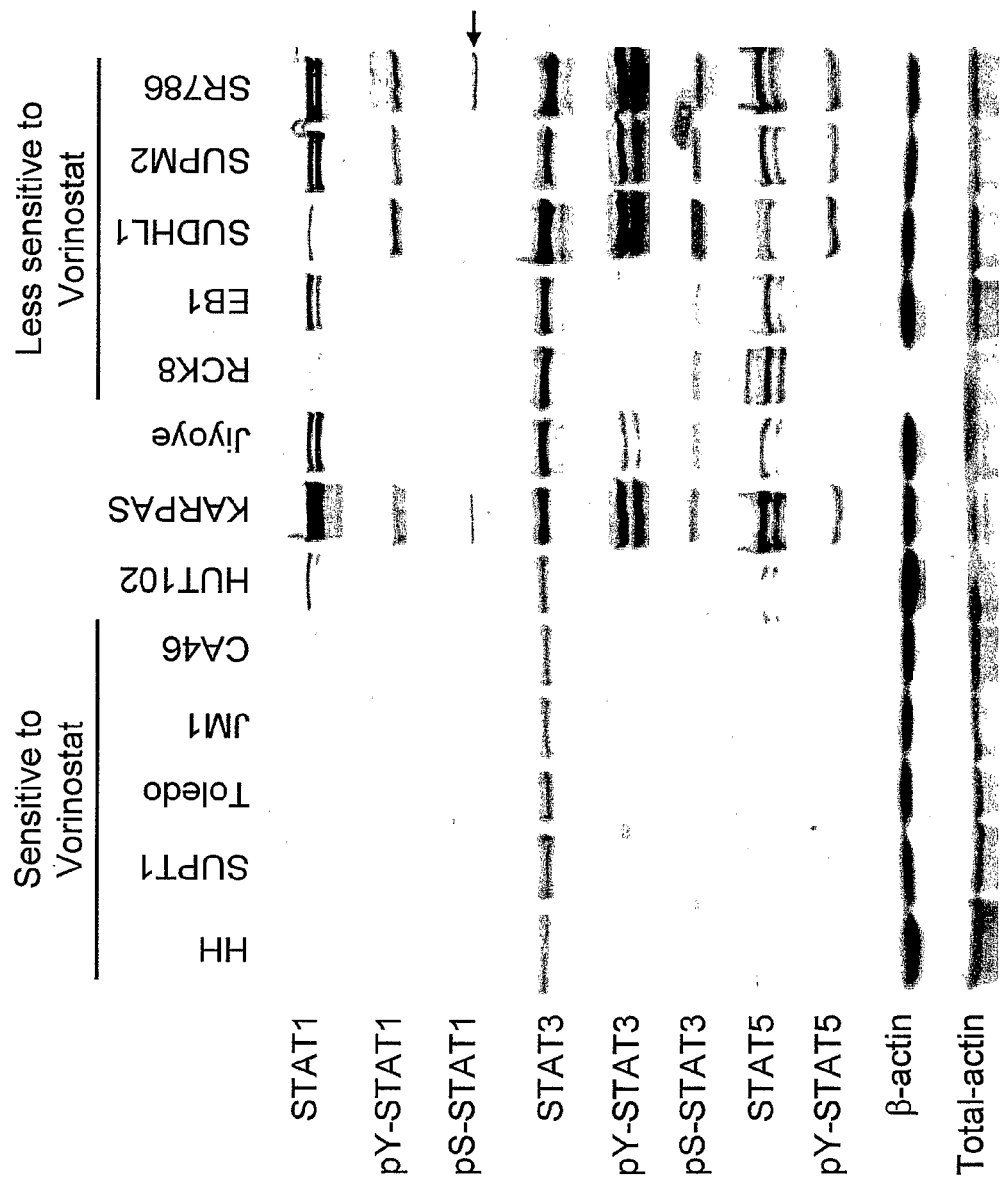
FIG. 1A. An Evaluation of expression and phosphorylation of STAT-1, STAT-3 and STAT-5 across a panel of human lymphoma cell lines. Whole cell lysates from lymphoma cell lines displaying diverse SAHA (vorinostat) sensitivity were prepared as described in the examples detailed here below. Samples were immunoblotted with antibodies against STAT-1, -3 and -5 as well as antibodies that react with the phosphorylated forms of the proteins. Samples were probed with antibodies against β-actin and total actin as loading controls.

Introduction
A. Biomarkers for Predicting Treatment Response to an Anti-Cancer Agent by Cancer Patients A sought after approach apart from currently accepted methods for screening for cancer has been the search for biomarkers that have value in prognosis and treatment of cancer including predicting whether a cancer patient is likely to benefit from treatment with a given anti-cancer agent.

Cutaneous T-cell lymphomas and peripheral T-cell lymphomas are forms of non-Hodgkin's lymphoma. Cutaneous T-cell lymphomas (CTCL) are a group of lymphoproliferative disorders characterized by localization of malignant T lymphocytes to the skin at presentation. CTCL frequently involves the skin, bloodstream, regional lymph nodes and spleen. Mycosis fungoides (MF), the most common and indolent form of CTCL, is characterized by patches, plaques or tumors containing epidermotropic $CD4^+CD45RO^+$ helper/memory T cells. MF may evolve into a leukemic variant, Sezary syndrome (SS), or transform to large cell lymphoma. The condition causes severe skin itching, pain and edema. Currently, CTCL is treated topically with steroids, photochemotherapy and chemotherapy, as well as radiotherapy. Peripheral T-cell lymphomas originate from mature or peripheral (not central or thymic) T-cell lymphocytes as a clonal proliferation from a single T-cell and are usually either predominantly nodal or extranodal tumors. They have T-cell lymphocyte cell-surface markers and clonal arrangements of the T-cell receptor genes. Approximately 16,000 to 20,000 people in the U.S. are affected by either CTCL or PTCL. These diseases are highly symptomatic. Patches, plaques and tumors are the clinical names of the different presentations. Patches are usually flat, possibly scaly and look like a "rash." Mycosis fungoides patches are often mistaken for eczema, psoriasis or non-specific dermatitis until a proper diagnosis of mycosis fungoides is made. Plaques are thicker, raised lesions. Tumors are raised "bumps" which may or may not ulcerate. A common characteristic is itching or pruritus, although many patients do not experience itching. It is possible to have one or all three of these phases. For most patients, existing treatments are palliative but not curative.

According to the National Cancer Institute, head and neck cancers account for three percent of all cancers in the U.S. Most head and neck cancers originate in the squamous cells lining the structures found in the head and neck, and are often referred to as squamous cell carcinomas of the head and neck (SCCHN). Some head and neck cancers originate in other types of cells, such as glandular cells. Head and neck cancers that originate in glandular cells are called adenocarcinomas. Head and neck cancers are further defined by the area in which they begin, such as the oral cavity, nasal cavity, larynx, pharynx, salivary glands, and lymph nodes of the upper part of the neck. It is estimated that 38,000 people in the U.S. developed head and neck cancer 2002. Approximately 60% of patients present with locally advanced disease. Only 30% of these patients achieve long-term remission after treatment with surgery and/or radiation. For patients with recurrent and/or metastatic disease, the median survival is approximately six months.

The biomarkers of this invention can also be applied to a wide variety of HDAC mediated cellular proliferative disorders. Within the context of the present invention, HDAC mediated cellular proliferative disorders include cancers; including, but not limited to, solid tumors (e.g., tumors of the head and neck, lung, breast, colon, prostate, bladder, rectum, brain, gastric tissue, bone, ovary, thyroid, or endometrium), hematological malignancies (e.g., leukemias, lymphomas, myelomas), carcinomas (e.g. bladder carcinoma, renal carcinoma, breast carcinoma, colorectal carcinoma), neuroblastoma, or melanoma. Non-limiting examples of these cancers include diffuse large B-cell lymphoma (DLBCL), T-cell lymphomas or leukemias, e.g., cutaneous T-cell lymphoma (CTCL), noncutaneous peripheral T-cell lymphoma, lymphoma associated with human T-cell lymphotrophic virus (HTLV), adult T-cell leukemia/lymphoma (ATLL), as well as acute lymphocytic leukemia, acute nonlymphocytic leukemia, acute myeloid leukemia, chronic lymphocytic leukemia, chronic myelogenous leukemia, Hodgkin's disease, non-Hodgkin's lymphoma, myeloma, multiple myeloma, mesothelioma, childhood solid tumors, neuroblastoma, retinoblastoma, glioma, Wilms' tumor, bone cancer and soft-tissue sarcomas, common solid tumors of adults such as head and neck cancers (e.g., oral, laryngeal and esophageal), genitourinary cancers (e.g., prostate, bladder, renal, uterine, ovarian, testicular, rectal and colon), lung cancer (e.g., small cell carcinoma and non-small cell lung carcinoma, including squamous cell carcinoma and adenocarcinoma), breast cancer, pancreatic cancer, melanoma and other skin cancers, stomach cancer, brain cancer, liver cancer, adrenal cancer, kidney cancer, thyroid cancer, basal cell carcinoma, squamous cell carcinoma of both ulcerating and papillary type, metastatic skin carcinoma, medullary carcinoma, osteo sarcoma, Ewing's sarcoma, veticulum cell sarcoma, and Kaposi's sarcoma. Also included are pediatric forms of any of the cancers described herein.

In a particular embodiment, the biomarkers of this invention can be applied to cancers such as Hodgkin's disease, non-Hodgkin's disease, myeloma, follicular cancer, mantle cell cancer, lymphomas such as anaplastic large cell lymphoma (ALCL), Burkitts lymphoma, DLBCL, histiocytic lymphoma, CTCL, B-cell primary effusion lymphoma (PEL), B-cell lymphoma and T-cell lymphoma. In another particular embodiment, the biomarkers of this invention can be applied to T-cell lymphomas. In a further particular embodiment, the biomarkers of this invention can be applied to multiple myeloma.

For over a decade, since the discovery of SAHA and its potential to treat HDAC-mediated cancers, the search for biomarkers for cancer treatment and treatment outcome in general has been in a state of evolution. Biomarkers for cancer have at least five potential uses in the management of patient care. Ideally, they would be used for risk assessment, for early diagnosis, for establishing prognosis, for monitoring treatment, and predicting whether a patient is resistant to particular anti-cancer agent (treatment outcome). Additionally, such markers could play a valuable role in successful early clinical intervention and developing alternative therapeutic interventions.

It is further advantageous for the sampling methods used in conjunction with biomarker analysis to be minimally invasive or non-invasive. Examples of such sampling methods include serum, stool, swabs, and the like. Non-invasive and minimally invasive methods increase patient compliance, and generally reduce cost.

Clinically, the two criteria that are important for assessing the effectiveness of biomarkers are selectivity and sensitivity. Selectivity of a biomarker defined clinically refers to percentage of patients correctly diagnosed. Sensitivity of a biomarker in a clinical context is defined as the probability that the disease is detected at a curable stage. Ideally, biomarkers would have 100% clinical selectivity and 100% clinical sensitivity. To date, no single biomarker has been identified that has an acceptably high degree of selectivity and sensitivity required to be effective in the broad range of needs in patient care management. The present invention aims to provide polypeptide biomarkers that may be used for risk assessment and predict with a high degree of reliability the treatment outcome with respect to a patient expressing higher than normal levels of one or more of the disclosed polypeptide biomarkers and thus provide substantive value in various aspects of patient care management. In the main, the invention as disclosed herein identifies a panel of (3) three polypeptide biomarkers as well as methods of identifying said biomarkers and correlating their expression patterns with treatment outcome particularly with respect to HDAC mediated cancers such as cancer, wherein the HDACi is SAHA.

The nucleotide and amino acid sequences of each biomarker member of the panel of biomarkers disclosed herein are well known. The preferred protein biomarkers for use in the invention methods are STAT-1, STAT-3 and STAT-5 including splice variants thereof as well as nucleic acid and protein analogs thereof. Each of these references are incorporated by reference herein in their entirety.

The invention further discloses antibodies that specifically or selectively bind to the protein biomarkers of the invention allowing measurement of the expression of the protein products of the invention and kits containing these polypeptides and/or polynucleotides.

In a first aspect, the disclosed invention relates to the identification and use of gene expression patterns (or profiles or "signatures") which discriminate between (or are correlated with) patients likely to respond to treatment with SAHA compared to those that are likely not to respond to treatment with SAHA or are susceptible to being SAHA resistant. Such patterns may be determined by the methods of the invention by use of a number of reference cell or tissue samples, such as those reviewed by a pathologist of ordinary skill in the pathology of cancer, which reflect cancer cells as opposed to normal or other non-cancerous cells. The outcomes experienced by the subjects from whom the samples may be correlated with expression data to identify patterns that correlate with the outcomes following SARA treatment. Because the overall gene expression profile differs from person to person, cancer to cancer, and cancer cell to cancer cell, correlations between certain cells and genes expressed or over-expressed may be made as disclosed herein to identify genes that are capable of discriminating between and identifying SAHA resistant patients (high-risk or at-risk patients) potentially SAHA-responsive patients. The identification may be made by using expression profiles of various homogenous cancer cell populations, which were isolated by microdissection, such as, but not limited to, laser capture microdissection (LCM) of 100-1000 cells. The expression level of each gene of the expression profile may be correlated with a particular outcome. Alternatively, the expression levels of multiple genes may be clustered to identify correlations with particular outcomes. The same holds true for protein expression profiles.

An embodiment using a nucleic acid based assay to determine expression is by immobilization of one or more sequences of the genes identified herein, e.g., those encoding any one or more of the members of the panel of biomarkers disclosed herein, on a solid support, including, but not limited to, a solid substrate as an array or to beads or bead based technology as known in the art. Alternatively, solution based expression assays known in the art may also be used. The immobilized gene(s) may be in the form of polynucleotides that are unique or otherwise specific to the gene(s) such that the polynucleotide would be capable of hybridizing to a DNA or RNA corresponding to the gene(s). These polynucleotides may be the full length of the gene(s) or be short sequences of the genes (up to one nucleotide shorter than the full length sequence known in the art by deletion from the 5' or 3' end of the sequence) that are optionally minimally interrupted (such as by mismatches or inserted non-complementary base pairs) such that hybridization with a DNA or RNA corresponding to the gene(s) is not affected. Preferably, the polynucleotides used are from the 3' end of the gene, such as within about 350, about 300, about 250, about 200, about 150, about 100, or about 50 nucleotides from the polyadenylation signal or polyadenylation site of a gene or expressed sequence. Polynucleotides containing mutations relative to the sequences of the disclosed genes may also be used so long as the presence of the mutations still allows hybridization to produce a detectable signal.

The immobilized gene(s) may be used to determine the state of nucleic acid samples prepared from sample cancer cell(s) for which the outcome of the sample's subject (e.g. patient from whom the sample is obtained) is not known or for confirmation of an outcome that is already assigned to the sample's subject. Without limiting the invention, such a cell may be from a patient with cancer cancer. The immobilized polynucleotide(s) need only be sufficient to specifically hybridize to the corresponding nucleic acid molecules derived from the sample under suitable conditions. While even a single correlated gene sequence may to able to provide adequate accuracy in discriminating between two cancer outcomes, it is preferable to correlate expression of all three gene sequences e.g., encoding one of STAT-1, -3 and -5 as a subset capable of predicting treatment outcome in order to increase the accuracy of the method.

The present invention includes the use of gene(s) the expression of which identify different treatment outcome for cancer patients with an HDAC inhibitor, preferably SAHA, such as to permit simultaneous identification of cancer patient survival/treatment outcome based upon assaying a cancer sample from said patient.

A broad embodiment discloses a panel of three polypeptide biomarkers with the selectivity and sensitivity required for managing patient care for predicting treatment outcome of cancer patients considering SAHA based therapy.

A biomarker, as defined by the National Institutes of Health (NIH) is a molecular indicator of a specific biological property; a biochemical feature or facet that can be used to measure the progress of disease or the effects of treatment. Thus, a biomarker is an organic biomolecule which is differentially present in a sample taken from a subject of one phenotypic status (e.g., having a disease) as compared with another phenotypic status (e.g., not having the disease). It is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. Therefore, they are useful inter alia, as markers for disease (diagnostics), therapeutic effectiveness of a drug (theranostics) toxicity. Based on the novel discovery detailed herein, differential expression of the biomarkers in a diseased cell relative to normal makes it now possible to predict treatment outcome.

As such the invention encompasses polynucleotides and polypeptides which can be used to detect and monitor differential nucleic acid or protein expression corresponding to at least one biomarker of the invention for predicting whether the patient is at risk of or susceptible to becoming SAHA-resistant. The invention also allows the monitoring of therapeutic treatments for cancer patients.

Thus, in accordance with the above, the present invention provides for the identification and use of three sets of sequences for the determination of responsiveness to SAHA treatment in cancer cancer. The differential expression of these sequences in cancer relative to normal T cells is used to predict SAHA responsiveness in a subject.

In a broad aspect, the invention is based upon the discovery that differential expression of at least one or more of the STAT protein biomarkers in a diseased sample relative to a control is predictive as to whether the patient is likely to become or is SAHA-resistant. A broad aspect of the invention is based upon the identification of specific STAT protein overexpression and phosphorylation status s, e.g., STAT-1, STAT-3 and STAT-5 as a predictor of vorinostat (SAHA) response in HDAC-mediated disorders lymphoma.

In accordance therewith, in an embodiment of the disclosure, expression levels of polynucleotides encoding one or more of the polypeptide biomarkers of the invention, e.g., inactivated STAT-1, 3 or 5 in a diseased sample relative to normal or a control sample are used in predicting whether the patient presenting with cancer is likely to benefit from treatment with a particular HDACi, e.g., SAHA. Such analysis of polynucleotide expression levels is frequently referred to in the art as gene expression profiling. In gene expression profiling, levels of mRNA in a sample are measured as a leading indicator of a biological state, in this case, as an indicator of SARA-resistance. One of the most common methods for analyzing gene expression profiling is to create multiple copies from mRNA in a biological sample using a process known as reverse transcription. In the process of reverse transcription, the mRNA from the sample is used to create copies of the corresponding DNA sequence from which the mRNA was originally transcribed. In the reverse transcription amplification process, copies of DNA are created without the regulatory regions in the gene known as introns. These multiple copies made from mRNA are therefore referred to as copy DNA, or cDNA.

Since the reverse transcription procedure amplifies copies of cDNA proportional to the original level of mRNA in a sample, it has become a standard method that allows the analysis of even low levels of mRNA present in a biological sample. Genes may either be up regulated or down regulated in any particular biological state, and hence mRNA levels shift accordingly.

Thus a method for measuring expression levels of polynucleotides encoding any one or more of the biomarker polypeptides of the invention comprises obtaining a biological sample for a cancer patient; isolating cellular RNA from the sample; amplifying copies of cDNA from the sample for each biomarker in the biomarker panel of the invention e.g., STAT-1, STAT-3, STAT-5 or splice variants and or analogs thereof; and quantifying levels of cDNA amplified from the sample, wherein a change in the levels of cDNA relative to a normal or control sample is indicative the treatment outcome for said cancer patient.

Examples of detection modes contemplated for the disclosed methods include, but are not limited to spectroscopic techniques, such as fluorescence and UV-Vis spectroscopy, scintillation counting, and mass spectroscopy. Complementary to these modes of detection, examples of labels for the purpose of detection and quantitation used in these methods include, but are not limited to chromophoric labels, scintillation labels, and mass labels. The expression levels of polynucleotides and polypeptides measured using these methods may be normalized to a control established for the purpose of the targeted determination. These methods are believed useful in providing determinations as the basis of effective management of patient care for CRC. These methods may also be used in the discovery of therapeutic interventions for CRC. Additionally, not only biopsy samples from sigmoidoscopy, colonoscopy, or surgery may be analyzed by these methods, but biological samples from non-invasive or minimally evasive collection methods are indicated for these methods, as well.

It is further contemplated in what is disclosed to provide kits having the reagents and procedures that facilitate the ready implementation of the methods, and provide consistency and quality control thereby.

Practice of the present invention will employ, unless otherwise indicated, conventional techniques of molecular biology, microbiology, recombinant DNA technology, electrophysiology, and pharmacology, that are within the skill of the art. Such techniques are explained fully in the literature. See, for example, Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan eds., Academic Press, Inc.); Transcription and Translation (Hames et al. eds. 1984); Gene Transfer Vectors For Mammalian Cells (J. H. Miller et al. eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. eds. (1991) IRL Press).

In another aspect, the invention provides a method of re-sensitizing or reversing a patients previously resistant to treatment with Vorinostat. According to this method, a patient previously or newly identified as being resistant to treatment with Vorinostat, can be sensitized to treatment in accordance with an embodiment of the invention. The proposed method contemplates administering to said patient an effective amount of a JAK inhibitor prior to or in combination with an effective amount of Vorinostat.

All patents, patent applications and publications cited herein, whether supra or infra, are hereby incorporated by reference in their entirety and are deemed representative of the prevailing state of the art.

As used in this specification and the appended claims, the singular forms "a," "an" and "the" include plural references unless the content clearly dictates otherwise. Thus, for example, reference to "a primer" includes two or more such primers, reference to "an amino acid" includes more than one such amino acid, and the like.

Definitions of Terms as Used Herein

As used herein, the term "amplified", when applied to a nucleic acid sequence, refers to a process whereby one or more copies of a particular nucleic acid sequence is generated from a template nucleic acid, preferably by the method of polymerase chain reaction (Mullis and Faloona, 1987, Methods Enzymol., 155:335). "Polymerase chain reaction" or "PCR" refers to an in vitro method for amplifying a specific nucleic acid template sequence. The PCR reaction involves a repetitive series of temperature cycles and is typically performed in a volume of 50-100 µl. The reaction mix comprises dNTPs (each of the four deoxynucleotides dATP, dCTP, dGTP, and dTTP), primers, buffers, DNA polymerase, and nucleic acid template. The PCR reaction comprises providing a set of polynucleotide primers wherein a first primer contains a sequence complementary to a region in one strand of the nucleic acid template sequence and primes the synthesis of a complementary DNA strand, and a second primer contains a sequence complementary to a region in a second strand of the target nucleic acid sequence and primes the synthesis of a complementary DNA strand, and amplifying the nucleic acid template sequence employing a nucleic acid polymerase as a template-dependent polymerizing agent under conditions which are permissive for PCR cycling steps of (i) annealing of primers required for amplification to a target nucleic acid sequence contained within the template sequence, (ii) extending the primers wherein the nucleic acid polymerase synthesizes a primer extension product. "A set of polynucleotide primers" or "a set of PCR primers" can comprise two, three, four or more primers. In one embodiment, an exo-Pfu DNA polymerase is used to amplify a nucleic acid template in PCR reaction. Other methods of amplification include, but are not limited to, ligase chain reaction (LCR), polynucleotide-specific based amplification (NSBA), or any other method known in the art.

According to the invention, an "array" contemplates a specific set of genes immobilized to a support, or a set of corresponding 5' ends or a set of corresponding 3' ends or a set of corresponding internal coding regions.

As used herein, the term "analog" in the context of proteinaceous agent (e.g., proteins, polypeptides, peptides, and antibodies) refers to a proteinaceous agent that possesses a similar or identical function as a second proteinaceous agent but does not necessarily comprise a similar or identical amino acid sequence of the second proteinaceous agent, or possess a similar or identical structure of the second proteinaceous agent. A proteinaceous agent that has a similar amino acid sequence refers to a second proteinaceous agent that satisfies at least one of the following: (a) a proteinaceous agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a second proteinaceous agent; (b) a proteinaceous agent encoded by a nucleotide sequence that hybridizes under stringent conditions to a nucleotide sequence encoding a second proteinaceous agent of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, or at least 150 contiguous amino acid residues; and (c) a proteinaceous agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding a second proteinaceous agent. A proteinaceous agent with similar structure to a second proteinaceous agent refers to a proteinaceous agent that has a similar secondary, tertiary or quaternary structure to the second proteinaceous agent. The structure of a proteinaceous agent can be determined by methods known to those skilled in the art, including but not limited to, peptide sequencing, X-ray crystallography, nuclear magnetic resonance, circular dichroism, and crystallographic electron microscopy. Within the context of the present invention, "analogs" of each of STAT-1, STAT-3 and STAT-5 are also encompassed by the methods of the invention.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, word length=12 to obtain nucleotide sequences homologous to a nucleic acid molecules of the present invention. BLAST protein searches can be performed with the XBLAST program parameters set, e.g., to score—50, word length=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

A "biologically active analog" and "analog" are used interchangeably herein to cover an organic or inorganic molecule that exhibits substantially the same agonist or antagonist effect of the first organic or inorganic molecule. A "nucleotide analog", as used herein, refers to a nucleotide in which the pentose sugar and/or one or more of the phosphate esters is replaced with its respective analog. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., including any associated counterions, if present. Also included within the definition of "nucleotide analog" are nucleobase monomers which can be polymerized into polynucleotide analogs in which the DNA/RNA phosphate ester and/or sugar phosphate ester backbone is replaced with a different type of linkage. Further included within "nucleotide analogs" are nucleotides in which the nucleobase moiety is non-conventional, i.e., differs from one of G, A, T, U or C. Generally a non-conventional nucleobase will have the capacity to form hydrogen bonds with at least one nucleobase moiety present on an adjacent counter-directional polynucleotide strand or provide a non-interacting, non-interfering base.

"Antibody" means an immunoglobulin or a derivative thereof that specifically binds to, and is thereby defined as complementary with, a particular spatial and polar organization of another molecule. The antibody can be monoclonal or an antibody derived from or comprised in a polyclonal antiserum, monoclonal antibodies are preferred. It can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc.

The term "antibody" also encompasses antigen-binding fragments of an antibody. The term "antigen-binding fragment" of an antibody (or simply "antibody portion," or "fragment"), as used herein, refers to one or more fragments of a full-length antibody that retain the ability to specifically bind to a polypeptide encoded by one of the genes of a biomarker of the invention. Examples of binding fragments encompassed within the term "antigen-binding fragment" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. The antibody is preferably monospecific, e.g., a monoclonal antibody, or antigen-binding fragment thereof. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition. See, for example Harlow and Lane, "Antibodies, A Laboratory Manual" CSH Press 1988, Cold Spring Harbor N.Y.

As used herein, the terms "attaching" and "spotting" refer to a process of depositing a nucleic acid onto a substrate to form a nucleic acid array such that the nucleic acid is stably bound to the substrate via covalent bonds, hydrogen bonds or ionic interactions.

As used herein, the baseline level used for the correlation can be determined by one of skill in the art. In one aspects the baseline level is the level of the at least one biomarker in a patient that is from normal tissue or from a non-cancerous patient. In another aspect, the baseline level is the level of the at least one biomarker, preferably all three in the patient that will be treated with an HDAC modulating agent but has not yet been exposed to the agent. In yet another aspect, the baseline level is the level of the at least one biomarkers of the invention in the patient that has been treated with a HDAC modulating agent, and wherein the baseline level is selected at a point during the treatment where the patient appear snot to be responding to treatment with the HDAC modulating agent. The point can be, for example, an established time period or measurement of a criteria (e.g., a biological or clinical response) set prior to initiation of the treatment. This baseline level can then be compared to a baseline level of another patient at the same time point who is responding to treatment with the same HDACi.

The term "biomarker" or "marker" encompasses a broad range of intra- and extra-cellular events as well as whole-organism physiological changes. Biomarkers may be represent essentially any aspect of cell function, for example, but not limited to, levels or rate of production of signaling molecules, transcription factors, metabolites, gene transcripts as well as post-translational modifications of proteins. Biomarkers may include whole genome analysis of transcript levels or whole proteome analysis of protein levels and/or modifications. Within the context of the present invention, a biomarker may refer to a gene or gene product which is up-regulated in a diseased cell of a subject having the disease compared to a normal or control cell, which is either isolated from a healthy patient or isolated from the subject but is otherwise normal. A difference between the level of at least one biomarker from the patient and the baseline level that is statistically significant can be used in the methods of the invention. A statistically significant difference between the level of at least one biomarker from the patient and the baseline level is readily determined by one of skill in the art and can be, for example, at least a two-fold difference, at least a three fold difference, or at least a four-fold difference in the level of the at least one biomarker. A "Biomarker of the invention" generally refers to the three (3) phosphorylated STAT proteins disclosed herein or may also include the inactive STAT proteins disclosed herein.

As used herein, the term "comprising" and its cognates are used in their inclusive sense; that is, equivalent to the term "including" and its corresponding cognates.

In one embodiment, a biomarker for practicing the methods of predicting a treatment outcome consists essentially of at least 2 or all 3 of the biomarkers of the invention.

A "coding region" refers to a DNA sequence encoding mRNA.

A nucleotide sequence is "complementary" to another nucleotide sequence if each of the bases of the two sequences match, that is, are capable of forming Watson-Crick base pairs. The term "complementary strand" is used herein interchangeably with the term "complement." The complement of a nucleic acid strand may be the complement of a coding strand or the complement of a non-coding strand.

As used herein, the term "derivative" in the context of proteinaceous agent (e.g., proteins, polypeptides, peptides, and antibodies) refers to a proteinaceous agent that comprises an amino acid sequence which has been altered by the introduction of amino acid residue substitutions, deletions, and/or additions. The term "derivative" as used herein also refers to a proteinaceous agent which has been modified, i.e., by the covalent attachment of any type of molecule to the proteinaceous agent. For example, but not by way of limitation, an antibody may be modified, e.g., by glycosylation, acetylation, pegylation, phosphorylation, amidation, derivatization by known protecting/blocking groups, proteolytic cleavage, linkage to a cellular ligand or other protein, etc. A derivative of a proteinaceous agent may be produced by chemical modifications using techniques known to those of skill in the art, including, but not limited to specific chemical cleavage, acetylation, formylation, metabolic synthesis of tunicamycin, etc. Further, a derivative of a proteinaceous agent may contain one or more non-classical amino acids. A derivative of a proteinaceous agent possesses a similar or identical function as the proteinaceous agent from which it was derived.

As used herein, "diagnosis" refers to a process of determining if an individual is afflicted with a disease or ailment. "Diagnosis of cancer" refers to a process of determining if an individual is afflicted with an HDAC mediated cancer.

As used herein, the term "differential expression" refers to a difference in the level of expression of the RNA of one or more biomarkers of the invention, as measured by the amount or level mRNA, and/or one or more spliced variants of mRNA of the biomarker in one sample as compared with the level of expression of the same one or more biomarkers of the invention in a second sample. "Differentially expressed" can also include a measurement of the protein corresponding to one or more, preferably all three biomarker of the invention in a sample or population of samples as compared with the amount or level of protein expression in a second sample or population of samples. Differential expression can be determined as described herein and as would be understood by a person skilled in the art. The term "differentially expressed" or "changes in the level of expression" refers to an increase or decrease in the measurable expression level of a given biomarker as measured by the amount of RNA and/or the amount of protein in a sample as compared with the measurable expression level of a given biomarker a second sample. The term "differentially expressed" or "changes in the level of expression" can also refer to an increase or decrease in the measurable expression level of a given biomarker in a population of samples as compared with the measurable expression level of a biomarker in a second population of samples. As used herein, "differentially expressed" can be measured using the ratio of the level of expression of a given biomarker(s) as compared with the mean expression level of the given biomarker(s) of a control wherein the ratio is not equal to 1. Differentially expressed can also be measured using p-value. When using p-value, a biomarker is identified as being differentially expressed as between a first and second population when the p-value is less than 0.1. More preferably the p-value is less than 0.05. Even more preferably the p-value is less than 0.01. More preferably still the p-value is less than 0.005. Most preferably the p-value is less than 0.001.

"Differentially increased expression" or "up regulation" refers to genes or proteins which demonstrate a statistically significant e.g., 1.1 fold, 1.2 fold, 1.4 fold, 1.6 fold, 1.8 fold, or more increase in gene expression (as measured by RNA expression or protein expression), relative to a control.

"Differentially decreased expression" or "down regulation" refers to genes which demonstrate a statistically significant decrease in gene expression (as measured by RNA expression or protein expression), relative to a control.

As used herein, the term "differential hybridization" refers to a difference in the quantitative level of hybridization of a nucleic acid sample from a first individual or individuals with a trait to a complementary nucleic acid target as compared with the hybridization of a nucleic acid sample from a second individual or individuals not having said trait to the same complementary nucleic acid target. A "differential hybridization" means that the ratio of the level of hybridization of the first sample as compared with the second sample is not equal to 1. For example, the ratio of the level of hybridization of the first sample to the target as compared to the second sample is greater than or less than 1.0, and includes greater than 1.5 and less than 0.7, greater than 2 and less than 0.5. A differential hybridization also exists if the hybridization is detectable in one sample but not another sample.

"A diseased cell" refers to a cell or tissue sample obtained from a patient presenting with cancer. That is, a cell which is a modified form of a normal cell and is not present in a subject not having cancer, or a cell which is present in significantly higher or lower numbers in subjects having cancer relative to subjects not having cancer.

As used herein, the term "drug efficacy" refers to the effectiveness of a drug. "Drug efficacy" is usually measured by the clinical response of the patient who has been or is being treated with a drug. A drug is considered to have a high degree of efficacy, if it achieves desired clinical results, for example, the alteration of gene expression and the gene expression pattern reflective of cancer as described herein. A general rule is that as the dose of a drug is increased, a greater effect is seen in the patient until a maximum desired effect is reached. If more drug is administered after the maximum point is reached, the side effects will normally increase.

As used herein, the term "effective amount" refers to the amount of a therapeutic moiety which is sufficient to reduce or ameliorate the progression, severity and/or duration of a diseased state, or one or more symptoms thereof, prevent the development, recurrence or one or more symptoms thereof, prevent the advancement of cancer or one or more symptoms thereof, or enhance or improve the prophylactic or therapeutic effect(s) of another therapy.

The term "expression profile," which is used interchangeably herein with "gene expression profile" and "fingerprint" of a cell refers to a set of values representing mRNA levels of one or more genes in a cell. An expression profile preferably comprises values representing expression levels of at least 3 genes encoding each of STAT-1, -3 and -5. As used herein, a "gene expression pattern" or "gene expression profile" preferably indicates the combined pattern of the results of the analysis of the level of expression of the three disclosed biomarkers of the invention. For example techniques to measure expression of the RNA products encoding the biomarkers of the invention includes, PCR based methods (including RT-PCR) and non PCR based method as well as microarray analysis. To measure the "protein expression profiles" of the protein biomarkers of the invention, techniques include western blotting and ELISA analysis.

As used herein, the term "fragment" in the context of a proteinaceous agent refers to a peptide or polypeptide that retains at least functional property attributable to the protein it is derived from. Thus, a fragment of STAT-1 would be a polypeptide of sufficient number of amino acids that is functionally equivalent to STAT-1.

As used herein, the term "hybridizing to" or "hybridization" refers to the sequence specific non-covalent binding interactions with a complementary nucleic acid, for example, interactions between a target nucleic acid sequence and a nucleic acid member on an array.

As used herein, "indicative of disease" when referring to an expression pattern indicates an expression pattern which is prognostic of a treatment outcome corresponding to a particular disease such that the expression pattern is found significantly more often in patients with a disease than in patients without the disease. Preferably, an expression pattern which is indicative of disease is found in a statistically significant number of patients who have the disease compared to those that do not have the disease. (Is this fine or do we want to include a percentage of patients. In other words "indicative of disease" reflects at least 70% of a patient population that present with said disease.

As used herein, "isolated" or "purified" when used in reference to a nucleic acid means that a naturally occurring sequence has been removed from its normal cellular (e.g., chromosomal) environment or is synthesized in a non-natural environment (e.g., artificially synthesized). Thus, an "isolated" or "purified" sequence may be in a cell-free solution or placed in a different cellular environment. The term "purified" does not imply that the sequence is the only nucleotide present, but that it is essentially free (about 90-95% pure) of non-nucleotide material naturally associated with it, and thus is distinguished from isolated chromosomes.

The term "label" refers to a composition capable of producing a detectable signal indicative of the presence of the labeled molecule. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

As used herein, the term "level of expression" or "expression" refers to the measurable expression level of a given nucleic acid or protein sequence. The level of expression of a nucleic acid is determined by methods well known in the art. As used herein, the term "level of expression" when referring to RNA refers to the measurable quantity of a given nucleic acid as determined by hybridization or measurements such as real-time RT PCR, which includes use of both SYBR® green and TaqMan® technology and which corresponds in direct proportion with the extent to which the gene is expressed. The level of expression of a nucleic acid is determined by methods well known in the art. For microarray analysis, the level of expression is measured by hybridization analysis using labeled nucleic acids corresponding to RNA isolated from one or more individuals according to methods well known in the art. The label on the nucleic acid used for hybridization can be a lumninescent label, an enzymatic label, a radioactive label, a chemical label or a physical label. Preferably, target nucleic acids are labeled with a fluorescent molecule. Preferred fluorescent labels include, but are not limited to: fluorescein, amino coumarin acetic acid, tetramethylrhodamine isothiocyanate (TRITC), Texas Red, Cyanine 3 (Cy3) and Cyanine 5 (Cy5). The term "significantly higher" indicates that the difference in STAT expression or phosphorylation level is statistically higher or significant. Preferably, the disorder is classified as being unresponsive to treatment with an HDAC inhibitor when the STAT expression level is at least 25% higher than that in the reference sample.

A nucleic acid is also said to be "differentially expressed" in two samples if one of the two samples contains no detectable expression of a given nucleic acid, provided that the detectably expressed nucleic acid is expressed at +/− at least 1.4 fold. Absolute quantification of the level of expression of a nucleic acid may be accomplished by including a known concentration(s) of one or more control nucleic acid species, generating a standard curve based on the amount of the control nucleic acid and extrapolating the expression level of the "unknown" nucleic acid species from the hybridization intensities of the unknown with respect to the standard curve. The same applies to protein or amino acid sequence expression profile. "Expression" and "gene expression" include transcription and/or translation of nucleic acid material.

The "profile" of a cell's biological state refers to the levels of various constituents of a cell which are predictive of the cells or patient's treatment outcome. Constituents of a cell include, for example, levels of RNA, levels of protein abundances, or protein activity levels.

A gene expression "pattern" or "profile" or "signature" refers to the relative expression of genes correlated with responsiveness to SAHA treatment of cancer patients. Responsiveness or lack thereof may be expressed as survival outcomes which are correlated with an expression "pattern" or "profile" or "signature" that is able to distinguish between, and predict, said outcomes.

The terms "correlate" or "correlation" or equivalents thereof refer to an association between expression of one or more genes or proteins and a treatment outcome of a cancer cell and/or a cancer patient in comparison to the lack of the response. The invention provides for the correlation between increases in expression of one or more of the herein disclosed STAT proteins and SAHA responsiveness in cancer presenting patients.

An "mRNA" means an RNA complementary to a gene; an mRNA includes a protein coding region and also may include 5' end and 3' untranslated regions (UTR).

As used herein, the term "majority" refers to a number representing more than 50% (e.g., 51%, 60%, or 70%, or 80% or 90% or up to 100%) of the total members of a composition. The term "majority", when referring to an array, it means more than 50% (e.g., 51%, 60%, or 70%, or 80% or 90% or up to 100%) of the total nucleic acid members that are stably associated with the solid substrate of the array.

Amelioration of cancer is defined herein as providing a clinical or therapeutic relief to individuals and generally includes relief of symptoms.

As used herein, "mRNA integrity" refers to the quality of mRNA extracts from either tissue samples or cell samples. mRNA extracts with good integrity do not appear to be degraded when examined by methods well known in the art, for example, by RNA agarose gel electrophoresis (e.g., Ausubel et al., John Wiley & Sons, Inc., 1997, Current Protocols in Molecular Biology). Preferably, the mRNA samples have good integrity (e.g., less than 10%, preferably less than 5%, and more preferably less than 1% of the mRNA is degraded) to truly represent the gene expression levels of the tissue or blood samples from which they are extracted.

As used herein, the terms "non-responsive" and "refractory" describe patients treated with a currently available therapy (e.g., prophylactic or therapeutic agent) for cancer, which is not clinically adequate to relieve one or more symptoms associated therewith. In other instances, "not responsive" "at risk" or "high risk" and grammatical equivalents thereof refer to patients identified according to the methods of the invention that are not likely to respond therapeutically to an HDACi such as SAHA, e.g., a SAHA based treatment or therapy is not going to be clinically effective in such patients.

As used herein, "normal" in the context of a conventional diagnosis or prognosis refers to an individual or group of individuals who have not shown any symptoms of cancer and are not known to suffer from this disorder. Preferably said normal individual(s) is not on medication for treating cancer. If possible said individual or group of individuals has not been diagnosed with cancer or any other cellular proliferative disorder such as cancer. It is also helpful if the normal individuals have similar sex, and age as compared with the test individuals. "Normal", according to the invention, also refers to a samples isolated from normal individuals and includes blood, total RNA or mRNA isolated from normal individuals. A sample taken from a normal individual can include RNA isolated from a blood sample wherein said blood sample is whole blood, lysed blood, centrifuged lysed blood or peripheral blood leukocytes (PBLs), and wherein the blood is from an individual who has not been diagnosed with cancer and does not show any symptoms of cancer at the time the blood is isolated. At other times, the clinical end point, e.g., mRNA levels may be replaced by "protein levels".

As used herein, "nucleic acid(s)" is interchangeable with the term "polynucleotide(s)" and it generally refers to any polyribonucleotide or poly-deoxyribonucleotide, which may be unmodified RNA or DNA or modified RNA or DNA or any combination thereof. "Nucleic acids" include, without limitation, single- and double-stranded nucleic acids. As used herein, the term "nucleic acid(s)" also includes DNAs or RNAs as described above that contain one or more modified bases. Thus, DNAs or RNAs with backbones modified for stability or for other reasons are "nucleic acids". The term "nucleic acids" as it is used herein embraces such chemically, enzymatically or metabolically modified forms of nucleic acids, as well as the chemical forms of DNA and RNA characteristic of viruses and cells, including for example, simple and complex cells. A "nucleic acid" or "nucleic acid sequence" may also include regions of single- or double-stranded RNA or DNA or any combinations thereof and can include expressed sequence tags (ESTs) according to some embodiments of the invention. An EST is a portion of the expressed sequence of a gene (i.e., the "tag" of a sequence), made by reverse transcribing a region of mRNA so as to make cDNA.

As defined herein, a "nucleic acid array" refers a plurality of nucleic acids (or "nucleic acid members") attached to a support where each of the nucleic acid members is attached to a support in a unique pre-selected region. In one embodiment, the nucleic acid member attached to the surface of the support is DNA. In a preferred embodiment, the nucleic acid member attached to the surface of the support is either cDNA or oligonucleotides. In another preferred embodiment, the nucleic acid member attached to the surface of the support is cDNA synthesized by polymerase chain reaction (PCR). The term "nucleic acid", as used herein, is interchangeable with the term "polynucleotide". In another preferred embodiment, a "nucleic acid array" refers to a plurality of unique nucleic acids attached to nitrocellulose or other membranes used in Southern and/or Northern blotting techniques.

As used herein "nucleic acid sample for hybridization to an array" is defined as a nucleic acid capable of binding to a nucleic acid bound to an array of complementary sequence through sets of non-covalent bonding interactions including complementary base pairing interactions. The nucleic acid sample for hybridization to an array can either be an isolated nucleic acid sequence corresponding to a gene or portion thereof, total RNA or mRNA isolated from a sample. Preferably, the nucleic acid sample for hybridization to an array is derived from human blood (including whole blood, lysed blood, centrifuged lysed blood, or peripheral blood leukocytes (PBLs)). More preferably, the nucleic acid sample is single- or double-stranded DNA, RNA, or DNA-RNA hybrids, from human blood and preferably from RNA or mRNA extracts.

As used herein, a "nucleic acid member on an array" or a "nucleic acid member" includes nucleic acid immobilized on an array and capable of binding to a nucleic acid probes or samples of complementary sequence through sets of non-covalent bonding interactions, including complementary base pairing interactions. As used herein, a nucleic acid member or target may include natural (i.e., A, G, C, or T) or modified bases (7-deazaguanosine, inosine, etc.). In addition, the bases in nucleic acids may be joined by a linkage other than a phosphodiester bond, so long as it does not interfere with hybridization (i.e., the nucleic acid target still specifically binds to its complementary sequence under standard stringent or selective hybridization conditions). Thus, nucleic acid members may be peptide nucleic acids in which the constituent bases are joined by peptide bonds rather than phosphodiester linkages. In one embodiment, a conventional nucleic acid array of 'target' sequences bound to the array can be representative of the entire human genome, e.g. Affymetrix chip, and the biomarker or isolated biomarker consisting of or comprising two or all 3 genes described herein or gene probes is applied to the conventional array. In another embodiment, sequences bound to the array can be the biomarker or isolated biomarker according to the invention and total cellular RNA is applied to the array.

As used herein, "patient" or "individual" refers to a mammal which is diagnosed with or presents with clinical symptoms corresponding to an HDAC mediated disorder such as cancer, e.g. CTCL.

As used herein, "polynucleotide" encompasses double-stranded DNA, single-stranded DNA and double-stranded or single-stranded RNA of more than 8 nucleotides in length. The term "polynucleotide" includes a polymeric form of nucleotides of any length, either ribonucleotides or deoxyribonucleotides, that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components.

As used herein, "polypeptide sequences encoded by" refers to the amino acid sequences obtained after translation of the protein coding region of a gene, as defined herein, corresponding to the sequences of any on or more of STAT-1, STAT-3 and/or STAT-5. The mRNA nucleotide sequence for each of the genes of the invention is identified by its Genbank Accession number (NM) and the corresponding polypeptide sequence is identified by a Protein Accession number (NP). When a protein or fragment of a protein is used to immunize a host animal, numerous regions of the protein may induce the production of antibodies which bind specifically to a given region or three-dimensional structure on the protein; these regions or structures are referred to as epitopes or antigenic determinants. As used herein, "antigenic fragments" refers portions of a polypeptide that contains one or more epitopes. Epitopes can be linear, comprising essentially a linear sequence from the antigen, or conformational, comprising sequences which are genetically separated by other sequences but come together structurally at the binding site for the polypeptide ligand.

Within the context of the present invention, the STAT proteins useful in the methods of the invention are identified as follows, wherein each of the references in incorporated by reference in its entirety:

STAT-1 isoform alpha; NM_007315, NP_009330
STAT-1 isoform beta; NM_1392266, NP_644671
STAT-3 variant 1; NM_139276, NP_644805
STAT-3 variant 2; NM_003150, NP_003141
STAT-3 variant 1; NM_213662, NP_998827
STAT-5 A; NM_003152, NP_003143
STAT-5 B; NM_012448, NP_036580

The term, "primer", as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, depending on the complexity of the target sequence, the oligonucleotide primer typically contains 15-25 or more nucleotides, although it may contain fewer nucleotides. The factors involved in determining the appropriate length of primer are readily known to one of ordinary skill in the art.

As used herein, the term "probe" means oligonucleotides and analogs thereof and refers to a range of chemical species that recognize polynucleotide target sequences through hydrogen bonding interactions with the nucleotide bases of the target sequences. The probe or the target sequences may be single- or double-stranded RNA or single- or double-stranded DNA or a combination of DNA and RNA bases. A probe is at least 8 nucleotides in length and less than the length of a complete gene. A probe may be 10, 20, 30, 50, 75, 100, 150, 200, 250, 400, 500 and up to 2000 nucleotides in length as long as it is less than the full length of the target gene. Probes can include oligonucleotides modified so as to have a tag which is detectable by fluorescence, chemiluminescence and the like. The probe can also be modified so as to have both a detectable tag and a quencher molecule, for example Taqman® and Molecular Beacon® probes.

Probes may also be mixtures of any of the oligonucleotide analog types together or in combination with native DNA or RNA. At the same time, the oligonucleotides and analogs thereof may be used alone or in combination with one or more additional oligonucleotides or analogs thereof.

As used herein the term "product of the biomarker" or "products of the biomarkers of the invention" refers to the RNA and/or the protein expressed by the gene encoding any one or more of the corresponding protein biomarker of the invention. In the case of RNA it refers to the RNA transcripts transcribed from genes corresponding to the biomarker of the invention. In the case of protein it refers to proteins translated from the genes corresponding to the biomarker of the invention. The "RNA product of a biomarker of the invention" includes mRNA transcripts, and/or specific spliced variants of mRNA whose measure of expression can be used as a biomarker in accordance with the teachings disclosed herein. The "protein product of a biomarker of the invention" includes proteins translated from the RNA products of the biomarkers of the invention.

"Prognostic of treatment outcome" refers to a process of predicting /determining if an individual afflicted with a HDAC mediated cancer, e.g., cancer is likely to respond or not respond to treatment with an HDAC inhibitor (HDACi) such as SAHA.

As used herein, the terms "protein" and "polypeptide" are used interchangeably to refer to a chain of amino acids linked together by peptide bonds. In a specific embodiment, a protein is composed of a sequence of amino acids corresponding to one of STAT-1, STAT-3 and/or STAT-5 or functionally equivalent analogs thereof. Within the context of the present invention, it is noted that there are several splice variants of STAT-1 and STAT-3, namely STAT-1 isoform alpha, STAT-1 isoform beta, STAT-3 variant 1, variant 2 and variant 3, all of which are included within the definition of STAT proteins of the invention. As well, STAT-5 includes STAT-5A and STAT-5B, each of which is encoded by a different gene. Consequently, STAT-1, STAT-3 and STAT-5 as used herein include all of the various splice variants and different proteins as indicated above, e.g., STAT-5A and STAT-5B. Functionally equivalent analogs thereof are also included in the definition of a STAT protein of the invention.

The term "sample" "control sample" as used herein designates one or more biological protein or nucleic acid samples isolated from an individual or group of individuals. In one aspect, the control sample is derived from an individual who is not afflicted with an HDAC mediated cellular proliferative disorder such as cancer. The term control or control sample can also refer to the compilation of data derived from samples of one or more individuals whose diagnosis has been confirmed as normal (not having cancer). A "tissue sample affected by a disorder" "clinical sample" or "diseased sample" or grammatical equivalents thereof refer to tissue or cells which differs from the corresponding tissue from a healthy individual or a healthy tissue or cell sample from the same patient. As used herein, the term includes a specimen (e.g., a biopsy or medical specimen, also referred to as a "patient sample" or "clinical sample") or a culture (e.g., microbiological culture). Such samples include, but are not limited to, sputum, blood, blood cells (e.g., white cells), tissue or biopsy samples (e.g., tumor biopsy), urine, peritoneal fluid, and pleural fluid, or cells therefrom. Biological samples may also include sections of tissues such as frozen sections taken for histological purposes. The difference may be a difference in morphology, histology, gene expression, response to treatment, protein composition etc.

In one embodiment of the invention, tissue or cell samples from a single patient determined to have carcinoma, e.g., cancer, can be separated by flow cytometry based on their level of hyper phosphorylated STAT proteins or their higher expression patterns. Cells showing a higher level of phosphorylated STAT proteins, for example, are considered to be cancerous while cells with moderate to low or no levels of phosphorylated STAT proteins (hyper-phosphorylated STAT) are considered to be normal. This type of separation enables a patients cancerous cells to be compared against the patient's own normal cells, thereby providing an ideal "internal" control population. The sample may be tissue material obtained through biopsy e.g. from a solid tumor of an individual. The tissue affected by the disorder includes cell lines which have been established from tumor tissue and transformed cell lines. Preferably, the sample is a composition which has been processed to be in a condition suitable for the method of determining the level of STAT-1, STAT-3 and/or STAT-5 expression or phosphorylation. The processing may include homogenization, extraction, fixation, washing and/or permeabilization. The type of processing largely depends on the technique which is used for determining the level of expression of at least one of the herein disclosed protein biomarkers, preferably all three.

In one embodiment, the "control sample" or "reference sample" is a sample which has been derived from tissue or cells of a healthy individual. The tissue from which this reference sample has been derived corresponds to the tissue affected by the disorder. For example, if the tissue affected by the disorder is tumor tissue from a cancer patient, the tissue from which the "reference sample" "control sample" has been derived is T cells from a healthy individual or normal T cells from the patient. The "reference sample" is usually processed in the same way as the sample derived from tissue affected by the disorder. If the STAT expression level in a certain tissue of a healthy individual is already known it is only required to determine the level of STAT expression in the sample affected by the disorder. For example, it may be envisaged that data on STAT expression in a large number of tissues from healthy individuals are collected. Once these data have been collected, one only has to examine the sample derived from tissue affected by a disorder to determine the treatment outcome with an HDAC inhibitor.

In another embodiment, the reference sample is a sample derived from tissue affected by the disorder. In this embodiment, the reference sample or the cells from which it has been derived have been contacted with an HDAC inhibitor (HDACi). For example, the sample may be derived from cancer tissue of a patient, preferably diseased T cells. Then the patient is treated with an HDAC inhibitor, and the reference sample is obtained from the same patient upon HDACi treatment. The reference sample may also be derived from cancer tissue or T cells of another patient suffering from the same disease who has been treated with HDACi and shown to have responded to such treatment. The sample may also be derived from cell culture cells, and the reference sample from a parallel culture of the same type of cells. The reference sample is subsequently processed in the same way as the first sample derived from tissue affected by the disorder. Usually, parallel samples are prepared which are processed identically. In another embodiment, the control sample may be normal T-cells derived from the diseased patient itself.

Within the context of the present invention, an increased level of STAT expression or phosphorylation (hyperphosphorylated STAT) in the diseased sample which has been treated with HDAC inhibitor (HDACi) compared to a reference sample obtained from the same patient or one obtained from another cancer patient who has responded favorably to the SAHA treatment indicates that the cells of the tissue affected by the disorder are not likely to respond to HDAC inhibitor treatment. The disorder may thus be classified as to be treated with an alternative HDAC inhibitor.

As used herein, the term "selectively binds" in the context of proteins encompassed by the invention refers to the specific interaction of a any two of a peptide, a protein, a polypeptide an antibody, wherein the interaction preferentially occurs as between any two of a peptide, protein, polypeptide and antibody preferentially as compared with any other peptide, protein, polypeptide and antibody. For example, when the two molecules are protein molecules, a structure on the first molecule recognizes and binds to a structure on the second molecule, rather than to other proteins. "Selective binding" as the term is used herein, means that a molecule binds its specific binding partner with at least 2-fold greater affinity. As used herein "selective hybridization" in the context of this invention refers to a hybridization which occurs as between a polynucleotide encompassed by the invention and an RNA or protein product of the biomarker of the invention wherein the hybridization is such that the polynucleotide binds to the RNA products of the biomarker of the invention preferentially to the RNA products of other genes in the genome in question. In a preferred embodiment a polynucleotide which "selectively hybridizes" is one which hybridizes with a selectivity of greater than 70%, greater than 80%, greater than 90% and most preferably on 100% (i.e., cross hybridization with other RNA species preferably occurs at less than 30%, less than 20%, less than 10%). As would be understood to a person skilled in the art, a polynucleotide which "selectively hybridizes" to the RNA product of a biomarker of the invention can be determined taking into account the length and composition.

As used herein, "spotting" or "attaching" refers to a process of depositing a nucleic acid member onto a solid substrate to form a nucleic acid array such that the nucleic acid is stably bound to the solid substrate via covalent bonds, hydrogen bonds or ionic interactions.

As used herein, "substrate" or "support" when referring to an array refers to a material having a rigid or semi-rigid surface. The support may be biological, non-biological, organic, inorganic, or a combination of any of these, existing as particles, strands, precipitates, gels, sheets, tubing, spheres, beads, containers, capillaries, pads, slices, films, plates, slides, chips, etc. Often, the substrate is a silicon or glass surface, (poly)tetrafluoroethylene, (poly)vinylidendifluoride, polystyrene, polycarbonate, a charged membrane, such as nylon 66 or nitrocellulose, or combinations thereof. In a preferred embodiment, the support is glass. Preferably, at least one surface of the substrate will be substantially flat. Preferably, the support will contain reactive groups, including, but not limited to, carboxyl, amino, hydroxyl, thiol, and the like. In one embodiment, the support is optically transparent.

The terms "STAT inhibitor", "JAK inhibitor", and "JAK/STAT inhibitor" are used interchangeably herein to refer to any agent capable of down-regulating or otherwise decreasing or suppressing the amount and/or activity of JAK-STAT interactions. JAK inhibitors down-regulate the quantity or activity of JAK molecules. STAT inhibitors down-regulate the quantity or activity of STAT molecules. Inhibition of these cellular components can be achieved by a variety of mechanisms known in the art, including, but not limited to binding directly to JAK (e.g., a JAK-inhibitor compound binding complex, or substrate mimetic), binding directly to STAT, or inhibiting the expression of the gene, which encodes the cellular components. JAK/STAT inhibitors are disclosed in U.S. patent publication 2004/0209799 (Vasios, G.).

Examples of JAK/STAT inhibitors which may be useful in the methods of this invention include, but are not limited to: PIAS proteins, which bind and inhibit at the level of the STAT proteins (Chung et al. Science, 1997, 278: 1803-1805); members of an SH2 containing family of proteins, which are able to bind to JAKs and/or receptors and block signaling (see, for example, Aman and Leonard Current Biology, 1997, 7:R784-788; Nicholson and Hilton J. Leukocyte Biol., 1998, 63: 665-668); cytokine-inducible Src homology 2-containing (CIS) protein, an inhibitor of STAT signaling (Yoshimura et al. EMBO J., 1995, 14: 2816-2826). Modulating STAT activity may be accomplished by targeting any number of STAT properties, including (a) recruitment to the receptor, (b) phosphorylation of SH2 domains, (c) STAT dephosphorylation (d) STAT dimerization, (e) nuclear translocation, ((DNA binding and transcriptional activation, (g) STAT protein expression, and (h) intracellular half-life of STAT.

A number of STAT modulators are described in the art. Peptide agents affecting recruitment are described in U.S. Pat. No. 5,731,155. As herein used, the term "standard stringent conditions" means hybridization will occur only if there is at least 95% and preferably, at least 97% identity between the sequences, wherein the region of identity comprises at least 10 nucleotides. In one embodiment, the sequences hybridize under stringent conditions following incubation of the sequences overnight at 42° C., followed by stringent washes (0.2×SSC at 65° C.). The degree of stringency of washing can be varied by changing the temperature, pH, ionic strength, divalent cation concentration, volume and duration of the washing. For example, the stringency of hybridization may be varied by conducting the hybridization at varying temperatures below the melting temperatures of the probes. The melting temperature of the probe may be calculated using the following formulas:

For oligonucleotide probes, between 14 and 70 nucleotides in length, the melting temperature (Tm) in degrees Celsius may be calculated using the formula: $Tm=81.5+16.6(\log [Na+])+0.41(\text{fraction } G+C)-(600/N)$ where N is the length of the oligonucleotide.

For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate stringency" conditions above 50° C. and "low stringency" conditions below 50° C. A specific example of "moderate stringency" hybridization conditions is when the above hybridization is conducted at 55° C. A specific example of "low stringency" hybridization conditions is when the above hybridization is conducted at 45° C.

If the hybridization is carried out in a solution containing formamide, the melting temperature may be calculated using the equation $Tm=81.5+16.6(\log [Na+])+0.41 (\text{fraction } G+C)-(0.63\% \text{ formamide})-(600/N)$, where N is the length of the probe.

For example, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate stringency" conditions above 25% formamide and "low stringency" conditions below 25% formamide. A specific example of "moderate stringency" hybridization conditions is when the above hybridization is conducted at 30% formamide. A specific example of "low stringency" hybridization conditions is when the above hybridization is conducted at 10% formamide.

As used herein, the term "significant match", when referring to nucleic acid sequences, means that two nucleic acid sequences exhibit at least 65% identity, at least 70%, at least 75%, at least 80%, at least 85%, and preferably, at least 90% identity, using comparison methods well known in the art (i.e., Altschul, S. F. et al., 1997, Nucl. Acids Res., 25:3389-3402; Schäffer, A. A. et al., 1999, Bioinformatics 15: 1000-1011).

As used herein, the term "therapeutically effective amount" refers to that amount of a therapy (e.g., a therapeutic agent) sufficient to result in the amelioration of cancer, for example, or one or more symptoms, prevent disease progression, or to enhance or improve the therapeutic effect(s) of another therapy (e.g., therapeutic agent). In a specific embodiment, a therapeutically effective amount refers to the amount of a therapeutic agent that modulates HDAC activity.

EMBODIMENTS OF THE INVENTION

In its broadest aspect, the invention provides polypeptide-based biomarkers that are differentially expressed in subjects presenting with cancer. The invention relies, in part, on the discovery, that differential expression of at least one or preferably all three of the polypeptide biomarkers of the invention in a diseased sample obtained from a cancer patient is predictive of the patient's treatment outcome with an HDACi.

Thus, in one embodiment, a method for gene expression profiling comprises measuring cDNA levels for one or more of the 3 polypeptide biomarkers detailed herein and measuring the expression profile wherein an increase in expression correlated to the ultimate treatment outcome.

Another broad embodiment proposes a method for protein expression profiling comprises using an antibody panel specific to the panel of biomarkers, e.g., one or more of STAT-1, STAT-3 or STAT-5 for measuring targeted polypeptide levels from a biological sample. In one embodiment contemplated for the method, the antibodies for the panel are bound to a solid support. The method for protein expression profiling may use a second antibody having specificity to some portion of the bound polypeptide. Such a second antibody may be labeled with molecules useful for detection and quantitation of the bound polypeptides, and therefore in binding to the polypeptide label it for detection and quantitation. Additionally, other reagents are contemplated for labeling the bound polypeptides for detection and quantitation. Such reagents may either directly label the bound polypeptide or, analogous to a second antibody, may be a moiety with specificity for the bound polypeptide having labels. Examples of such moieties include but are not limited to small molecules such as cofactors, substrates, complexing agents, and the like, or large molecules, such as lectins, peptides, olionucleotides, and the like. Such moieties may be either naturally occurring or synthetic.

In another aspect, invention relies on predicting the treatment outcome of a cancer patient by analyzing a diseases cell or tissue sample for the phosphorylation status of at least one or more of the biomarkers disclosed herein. An increased level of hyper-phosphorylated STAT protein, preferably one or more of STAT-1, STAT-3, and STAT-5 is indicative that the patient is at risk of non responding favorably to treatment with an HDACi such as SAHA or is SAHA-resistant.

In another aspect, the invention provides novel compositions and methods for their use in classifying cancer tumors. As used herein, the term "classifying" means to determine one or more features of the tumor or the prognosis of a patient from whom a tissue sample is taken, including the following: (a) Prognosis of patient response to treatment (SAHA-based chemotherapy, or alternative therapy-radiation etc and/or surgery); (b) Predicted optimal course of treatment for the patient, assuming the patient was initially enrolled in a SAHA-based therapy and is subsequently identified as being at-risk of not responding to SAHA, based upon the expression profiles detailed herein; and (c) Patient life expectancy.

"SAHA" refers to suberoylanilide hydroxamic acid (vorinostat), which is a member of the hybrid polar compounds (HPCs) and induces cell growth arrest, terminal differentiation and/or apoptosis in various transformed cell lines. It is a histone deacetylase (HDAC) inhibitor, and is reported to cause accumulation of hyperacetylated histone H4 in murine erythroleukemia. Richon et al., "A class of hybrid polar inducers of transformed cell differentiation inhibits histone deacetylases", Proc Natl. Acad. Sci. USA, 95:3003-3007 (1998). See also Marks et al., "Histone deacetylase inhibitors: inducers of differentiation or apoptosis of transformed cells," J. Natl. Cancer Inst., 92(15):1210-1216, (2000); Desai, D. et al., "Chemopreventive efficacy of suberanilohydroxamic acid (SAHA), a cytodifferentiating agent, against tobacco-specific nitrosamine 4-(-methylnitros-amino)-1-(3-pyridyl)-1-butanone (NNK)-induced lung tuinorigenesis in female A/J mice," Proc. AACR, vol. 40, abstract #2396 (1999). See also US RE 38, 506. Each reference is incorporated by reference herein in its entirety.

STAT Proteins—a Brief Overview

It has been established for more than a decade that gene transcription can be initiated within minutes after the activation of cell surface receptors by polypeptide ligands (reviewed in [Levy, D. E. and Darnell, J. E., New Biologist 2: 923-928 (1990)] and Darnell, J. E., Proc. Natl. Acad. Sci. (USA), 94:11767-11769 (1997)]. One of the most direct pathways of polypeptide stimulated gene activity is the so-called Jak-STAT pathway[Briscoe et al., Phil Trans. Royal Soc. (London) B351: 167-171 (1996); [Darnell, 1997; Ihle et al., Annu. Rev. Immunol., 13:369-398 (1995); Leaman et al., FASEB J., 10:1578-1588 (1996)].

The STATs (Signal Transducer and Activator of Transcription) constitute a family of latent transcription factors necessary to activate distinct sets of target genes in response to cytokines and growth factors [Darnell et al. WO 95/08629, (1995)]. To function as specific transcriptional activators, STAT proteins by themselves or in combination with other proteins must have the ability to recognize specific DNA sequence elements in the promoters of their target genes.

STAT proteins display a number of conserved features. The amino terminal part of the protein participates in cooperative interactions involved in DNA binding. An adjacent coiled-coil domain functions as an interaction region for a number of regulatory modifiers, including interferon regulatory factor IRF-9 and STAT-interacting protein StIPI (Colium, R. G. et al., Proc. Natl. Acad. Sci. USA 97(18):10120-10125 (2000)). The DIVA binding domain at the carboxy terminal half of STAT recognizes GAS type enhancer sequences on target genes while transcriptional activation occurs through the transcriptional activation domain (TAD) localized toward the carboxy terminus. The length and sequence of the TAD vary substantially between STATs. Src homology 2 domain (SH2) is the most conserved region of STATs and mediates recruitment of STAT to receptors and STAT dimerization. A linker region separating the SH2 domain from the DNA binding region appears to function as a buffer to limit perturbations to DNA binding interactions. Upon receptor activation by ligand binding, the receptor tyrosine kinase or receptor associated family of cytoplasmic kineses, such as Janus kinase (JAK), Tyk2, and src kinases, phosphorylates the receptor to generate docking sites for the SH2 domains of STAT. Following recruitment, the receptor bound STATs become phosphorylated at the SH2 domains at specific tyrosine residues, dimerize. The phosphorylated dimer is then actively transported in the nucleus via importing a/b and Ran GDP complex. Once inside the nucleus the activated STAT dimers then bind to specific DNA-response elements in promoters and induce expression of target genes thereby regulating their transcription. The STAT protein can be dephosphorylated by nuclear phosphatases which lead to inactivation of STAT and the transcription factor becomes transported out of the nucleus by exporting crm1/RanGTP. (Darnell, et al., Science, 1994, 264: 1415-1421; Ihle, Nature, 1995, Nature, 377: 591-594; Ihle, TIBS, 1994, 19: 222-227; Darnell, Science, 1997, 277: 1630-1635). One distinctive characteristic of the STAT proteins are their apparent lack of requirement for changes in second passenger, e.g., cAMP or Ca.sup.++, concentrations.

Seven STATs have been identified in mammalian cells and are implicated in controlling cell growth, cell differentiation, organogenesis, embryonic development, and host responses to cancer and infection. STAT proteins have the dual purpose of, first, signal transduction from ligand-activated receptor kinase complexes followed by nuclear translocation and DNA binding to activate transcription (Darnell et al., 1994, Science 264:1415-1421).

Of the known mammalian STAT proteins, STAT-1, STAT-2, and STAT-3 display the broadest expression profiles and regulate cellular responses to extracellular ligands in most cell types (Zhong, Y. et al., Oncogene 21:217-226 (2002); Zhong, Z. et al., Proc. Natl. Acad. Sci. USA 91:4806-4810 (1994)). Confirming the physiological role of STAT-1, inactivation of the STAT-1 gene in mice results in animals with defective immune responses as a result of disruptions to IFN signaling. STAT-3 is activated by a variety of cytokines including, among others, interleukin-6 (IL6), leukemia inhibitory factor (LIF), ciliary neurotrophic factor (CNTF), oncostatin M, and leptin (Hirano, T. et al., Oncogene 19:2548-2556 (2000)). STAT-3 is also activated by growth factor receptors with intrinsic protein tyrosine kinase activity, including, among others, PDGF, EGF, G-CSF, and Neuregulin-1 (NRG-1) receptors (Sadowski, H B. et al., Science 261: 1739-1744 (1993); Vignais, M. L. et al., Mol. Cell. Biol. 16:1759-1769 (1996); Liu, J. and Kern, J. A., Am. J. Respir. Cell Mol. Biol. 27(3):306-313 (2002)) as well as cellular and viral cytoplasmic tyrosine kineses, such as c-Src and v-Src (Bromberg, J. et al., Mol. Cell. Biol. 18:2553-2558 (1998), Yu, C. L., et al., Science 269:81-83 (1995)).

STAT-3 plays a role in cellular growth and differentiation of mammary gland, liver, keratinocytes, thymus, blood, and neurons, and its activation is associated with the inflammatory process, liver regeneration, acute phase responses, and other physiological responses (Akira, S., Oncogene 19:2607-2611 (2000); Levy, D. E. and Lee, C., J. Clin. Invest. 109: 1143-1148 (2002)). STAT-3 is frequently found hyper-activated in human cancers and cancer cell lines, and studies implicate STAT-3 as an Oncogene involved in malignant transformation (Darrell, J. E., Natl. Rev. Cancer 2:740-749 (2002), Bromberg, J. et al., supra; Yoshida, T. et al., J. Exp. Med. 196:641-653 (2002); and Yu, C. et al., supra) and tumor maintenance, as suggested by spontaneous: programmed cell death following STAT-3 inhibition in cancer cells (Catlet-Falcone, R. et al., Immunity 10: 105-115 (1999), Grandis, J. R. et al., Proc. Natl. Acad. Sci. USA 97:42274232 (2000); Niu, G. et al., Cancer Res. 61:3276-3280 (2001); Niu, G. et al., Oncogene 21:2000-2008 (2002)).

Prognostic Detection of STAT Expression Using Antibody Based Methodologies

Detection of cellular STAT expression levels can provide an important tool in monitoring the cellular response to specific anticancer treatments.

Towards this end, an embodiment of the invention provides for determining expression levels of proteins corresponding to the sequences of one or STAT -1, -3, or -5 for the purposes of predicting a patients response to an HDACi such as SAHA. The term "polypeptide" or "polypeptides" is used interchangeably with the term "protein" or "proteins" herein. Proteins have been long investigated for their potential as biomarkers. There is value in protein biomarkers as complementary to polynucleotide biomarkers. Reasons for having the information provided by both types of biomarker expression levels include the current observations that mRNA expression levels alone are not good predictors of protein expression levels, and that mRNA expression levels tell nothing of the post-translational modifications of proteins that are key to their biological activity. Therefore, in order to understand the expression levels of proteins, and their complete structure, the direct analysis of proteins is required.

In furtherance of the above method, one analyzes the protein levels corresponding to the biomarker panel of the invention, which incidentally comprises the sequences for one or more of STAT-1, STAT-3 and STAT-5. After quantifying the protein levels, one then determines whether there is an increase in the expression levels relative to normal. Alternatively, one may analyze the phosphorylation status of any one or more of the biomarkers of the biomarker panel of the invention. An increase in expression levels of one of the protein biomarker of the invention or an increase in the levels of a hyper-phosphorylated protein biomarker of the invention is suggestive of a poor prognosis of treatment with an HDACi such as SAHA with respect to the particular patient from whom the same was obtained.

Standard techniques can also be utilized for determining the amount of the protein or proteins of interest present in a sample. For example, standard techniques can be employed using, e.g., immunoassays such as, for example, Western blot, immunoprecipitation followed by sodium dodecyl sulfate polyacrylamide gel electrophoresis (SDS-PAGE), immunocytochemistry, and the like to determine the amount of the protein or proteins of interest present in a sample. A preferred agent for detecting a protein of interest is an antibody capable of binding to a protein of interest, preferably an antibody with a detectable label.

For such detection methods, protein from the sample to be analyzed can easily be isolated using techniques which are well known to those of skill in the art. Protein isolation methods can, for example, be such as those described in Harlow and Lane (Harlow, E. and Lane, D., Antibodies: A Laboratory Manual, Cold Spring Harbor Laboratory Press, Cold Spring Harbor, N.Y. (1988)).

Preferred methods for the detection of the protein or proteins of interest involve their detection via interaction with a protein-specific antibody. For example, antibodies directed a protein of interest can be utilized as described herein. Antibodies can be generated utilizing standard techniques well known to those of skill in the art. Antibodies for use in such methods of detection include polyclonal antibodies, optionally isolated from naturally occurring sources where available, and monoclonal antibodies, including those prepared by use of one of STAT-1, STAT-3 or STAT-5 or functionally effective fragments thereof as antigens. Such antibodies, as well as fragments thereof (including but not limited to Fab fragments) function to detect or diagnose non-normal or cancerous diseased tissue or cells by virtue of their ability to specifically bind the antigen used to prepare the antibody to the exclusion of other polypeptides to produce a detectable signal. Recombinant, synthetic, and hybrid antibodies with the same ability may also be used in the practice of the invention. Antibodies may be readily generated by immunization with a phosphorylated STAT-1, STAT-3 polypeptide, and polyclonal sera may also be used in the practice of the invention.

Briefly, such antibodies can be polyclonal, or more preferably, monoclonal. An intact antibody, or an antibody fragment (e.g., Fab or $F(ab^1)_2$) can, for example, be used. The antibody or the derivative thereof may be of natural origin or may be (semi)synthetically produced. Such synthetic products also comprises non-proteinaceous or semi-proteinaceous material that has the same or essentially the same binding specificity as the antibody of the invention. Preferably, the antibody is a human or humanized antibody.

For example, antibodies, or fragments of antibodies, specific for a protein of interest can be used to quantitatively or qualitatively detect the presence of the protein. This can be accomplished, for example, by immunofluorescence techniques. Antibodies (or fragments thereof) can, additionally, be employed histologically, as in immunofluorescence or immunoelectron microscopy, for in situ detection of a protein of interest. In situ detection can be accomplished by removing a histological specimen (e.g., a biopsy specimen) from a patient, and applying thereto a labeled antibody thereto that is directed to a protein. The antibody (or fragment) is preferably applied by overlaying the labeled antibody (or fragment) onto a biological sample. Through the use of such a procedure, it is possible to determine not only the presence of the protein of interest, but also its distribution, its presence in cells (e.g., brain cells and lymphocytes) within the sample. A wide variety of well-known histological methods (such as staining procedures) can be utilized in order to achieve such in situ detection.

Immunoassays for a protein of interest typically comprise incubating a biological sample of a detectably labeled antibody capable of identifying a protein of interest, and detecting the bound antibody by any of a number of techniques well-known in the art. As discussed in more detail, below, the term "labeled" can refer to direct labeling of the antibody via, e.g., coupling (i.e., physically linking) a detectable substance to the antibody, and can also refer to indirect labeling of the antibody by reactivity with another reagent that is directly labeled. Examples of indirect labeling include detection of a primary antibody using a fluorescently labeled secondary antibody.

For example, the biological sample can be brought in contact with and immobilized onto a solid phase support or carrier such as nitrocellulose, or other support which is capable of immobilizing cells, cell particles or soluble proteins. The support can then be washed with suitable buffers followed by treatment with the detectably labeled fingerprint gene-specific antibody. The solid phase support can then be washed with the buffer a second time to remove unbound antibody. The amount of bound label on support can then be detected by conventional means.

By "solid phase support or carrier" in the context of proteinaceous agents is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention.

The support material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, etc. Preferred supports include polystyrene beads. Those skilled in the art will know many other suitable carriers for binding antibody or antigen, or will be able to ascertain the same by use of routine experimentation.

One of the ways in which a specific antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1-7, Microbiological Associates Quarterly Publication, Walkersville, Md.); Voller, A. et al., 1978, J. Clin. Pathol. 31:507-520; Butler, J. E., 1981, Meth. Enzymol. 73:482-523; Maggio, E. (ed.), 1980, *Enzyme Immunoassay*, CRC Press, Boca Raton, Fla.; Ishikawa, E. et al., (eds.), 1981, *Enzyme Immunoassay*, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibodies or antibody fragments, it is possible to detect a protein of interest through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope (e.g., $^{125}$I, $^{131}$I, $^{35}$S or $^{3}$H) can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound can be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Thus, in one aspect, the methods of the invention allow the clinician to predict or determine the clinical treatment outcome with respect to a patient presenting with cancer. More specifically, this aspect of the invention allows the skilled artisan to isolate and identify patients with cancer who are at risk of not-responding to or susceptible to becoming SAHA-resistant based, principally, on the expression or phosphorylation status of at least one or more of the disclosed STAT proteins in a diseased tissue or cell sample (clinical sample) relative to a normal or control sample (reference sample). An important aspect of the method of the present invention is therefore the use of these antibody tools to identify patients and tumor entities that may be unresponsive or resistant to treatment with an HDACi exemplified by SAHA.

The antibody to detect STAT expression or phosphorylation status in accordance with the invention is capable of binding to a specific activated STAT protein, preferably to one of STAT -1, -3 or -5. In another embodiment, the antibody binds to phosphorylated STAT proteins, e.g., one of STAT-1, STAT -3 or STAT-5 but not to corresponding unphosphorylated STAT-1, STAT-3 or STAT-5. Preferably, the antibody does not cross react, e.g., one that binds phosphorylated STAT-1 does not cross-react with phosphorylated STAT-3 or -5 etc. "Antibody binding composition" means a molecule or a complex of molecules that comprises one or more antibodies, or fragments thereof, and derives its binding specificity from such antibody or antibody fragment.

In one aspect, the invention provides a method of determining whether a patient receiving a treatment that comprises a HDAC modulating agent has received sufficient treatment to inhibit HDAC in the patient's tumors. In accordance with the invention, tumor or surrogate biopsies are obtained from a patient before and after treatment with the HDAC modulating agent (HDACi). The surrogate biopsies can be, for example, skin or peripheral blood. The cells are then assayed to determine the changes in the expression pattern of one or more biomarkers of the invention upon treatment with the HDAC modulating agent, to determine not only whether HDAC inhibition has been achieved by the treatment but also whether the patient is at risk of failing said treatment. Success or failure of the treatment can be determined based on the expression pattern of the test cells from the test tissue, e.g., tumor or cancer biopsy, as being relatively the same as or different from the expression pattern of one or more biomarkers. If the test cells show an expression profile that corresponds to either no change or an increase in the expression levels of one or more of the biomarkers of the invention, it is predicted that the individual's cancer or tumor is likely not to respond to further treatment as the patient may either be SAHA-resistant or susceptible to becoming SAHA resistant.

Monitoring of the efficacy of HDACi treatment in patients, e.g., determining whether a patient currently undergoing treatment with an HDACi should continue treatment with the HDACi is as important as the underlying therapy.

Consequently, an embodiment of the invention provides a method of monitoring the treatment of a patient having a disease treatable by a HDAC modulating agent by comparing the expression profile of cells from a patient tissue sample, e.g., a tumor or cancer biopsy. The isolated cells from the patient are assayed to determine their expression pattern, to determine either the expression levels of one of the STAT biomarkers of the invention or alternatively the phosphorylation status relative to normal or non-cancerous cells. A change, such as an increase in the expression levels of the STAT protein disclosed herein warrants a different treatment, such as treatment with a different HDAC modulating agent, or to discontinue current treatment. With respect to this particular embodiment, various reference samples may be taken at different time points from the patient who is undergoing treatment with an HDACi. Here, the level of STAT expression is determined over various time points. Such a monitoring process can indicate success or failure of a patient's treatment with a HDAC modulating agent (HDACi) based on the expression pattern of the cells isolated from the patient's sample. Thus, if, after treatment continued treatment with the HDAC modulating agent, the test cells show a change in their expression profile of any one or more of the biomarkers of the invention, it can serve as an indicator that the current treatment should be modified, changed, or even discontinued. Such monitoring processes can be repeated as necessary or desired. The monitoring of a patient's response to a given treatment can also involve testing the patient's cells in the assay as described only after treatment with a HDAC modulating agent, rather than before and after treatment with a HDAC modulating agent. As well, when the level of STAT expression in spite of continued HDACi treatment remains high or after an initial decrease increases again and approaches the level in the sample, the treatment may be inefficient.

This prognostic monitoring aspect of the invention is suitable for disorders or diseases in which the induction of STAT activation, e.g., be it an increased in expression at the mRNA or protein level or hyper-phosphorylation of particular amino acid residue in response to an external stimuli has a beneficial effect of earlier clinical intervention with alternative therapies that may ultimately benefit the patient instead of prolonging therapy with an anti-cancer agent that is likely to not be therapeutically effective.

Antibody binding compositions include, but are not limited to, (i) antibody pairs in which a first antibody binds specifically to a target molecule and a second antibody binds specifically to a constant region of the first antibody; a biotinylated antibody that binds specifically to a target molecule and a streptavidin protein, which protein is derivatized with moieties such as molecular tags or photosensitizers, or the like, via a biotin moiety; (ii) antibodies specific for a target molecule and conjugated to a polymer, such as dextran, which, in turn, is derivatized with moieties such as molecular tags or photosensitizers, either directly by covalent bonds or indirectly via streptavidin-biotin linkages; (iii) antibodies specific for a target molecule and conjugated to a bead, or microbead, or other solid phase support, which, in turn, is derivatized either directly or indirectly with moieties such as molecular tags or photosensitizers, or polymers containing the latter.

"Specific" or "specificity" in reference to the binding of one molecule to another molecule, such as a binding compound, or probe, for a target analyte or complex, means the recognition, contact, and formation of a stable complex between the probe and target, together with substantially less recognition, contact, or complex formation of the probe with other molecules. In one aspect, "specific" in reference to the binding of a first molecule to a second molecule means that to the extent the first molecule recognizes and forms a complex with another molecule in a reaction, or sample, it forms the largest number of the complexes with the second molecule. In one aspect, this largest number is at least fifty percent of all such complexes form by the first molecule. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like.

Detection of sequences, e.g., increase in the level of phosphorylated STAT-1 for example, may be performed by any immunohistochemistry (IHC) based, bodily fluid based (where a STAT protein is found in a bodily fluid, such as but not limited to blood), antibody (including autoantibodies against the protein where present) based, ex foliate cell (from the cancer) based, mass spectroscopy based, and image (including used of labeled ligand where available) based method known in the art and recognized as appropriate for the detection of the protein. Antibody and image based methods are additionally useful for the localization of tumors after determination of cancer by use of cells obtained by a non-invasive procedure (such as ductal lavage or fine needle aspiration), where the source of the cancerous cells is not known. A labeled antibody or ligand may be used to localize the carcinoma(s) within a patient. The level of STAT expression can be determined by a variety of methods. Western Blotting may be used, which is a method known in the art. The tissue material may be treated with denaturing and/or reducing agents to obtain the sample. The sample may be loaded on a polyacrylamide gel to separate the proteins followed by transfer to a membrane or directly be spotted on a solid phase. The antibody is then contacted with the sample. After one or more washing steps the bound antibody is detected using techniques which are known in the art. Gel electrophoresis of proteins and Western Blotting is described in Golemis, "Protein-Protein Interactions: A Laboratory Manual", CSH Press 2002, Cold Spring Harbor N.Y.

Immunohistochemistry may be used after fixation and permeabilisation of tissue material, e.g. slices of solid tumors. The antibody is then incubated with the sample, and following one or more washing steps the bound antibody is detected. The techniques are outlined in Harlow and Lane, "Antibodies, A Laboratory Manual" CSH Press 1988, Cold Spring Harbor FLY. In a preferred embodiment, the level of STAT expression is determined by way of an ELISA. A variety of formats of the ELISA can be envisaged. In one format, the antibody is immobilized on a solid phase such as a microtiter plate, followed by blocking of unspecific binding sites and incubation with the sample. In another format, the sample is first contacted with the solid phase to immobilize the histones contained in the sample. After blocking and optionally washing, the antibody is contacted with the immobilized sample. ELISA techniques are described in Harlow and Lane, "Antibodies, A Laboratory Manual" CSH Press 1988, Cold Spring Harbor N.Y.

Alternatively, the level of STAT expression is determined by flow cytometry. Cells obtained from the tissue affected by the disorder, e.g. blood cells or cells from bone marrow, are fixed and permeabilized to allow the antibody to reach nuclear proteins. After optional washing and blocking steps the antibody is contacted with the cells. Flow cytometry is then performed in accordance with procedures known in the art in order to determine cells having antibody bound to their histones. Various flow cytometry methods are described in Robinson "Current Protocols in Cytometry" John Wiley & Sons Inc., New York. A method of quantitatively determining the level of STAT expression is shown in Example 3. As used herein, the term "kit" refers to any delivery system for delivering materials. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.
Protein-Antibody Arrays:

Polypeptides which specifically and/or selectively bind to the protein biomarkers of the invention can be immobilized on a protein array. The protein array can be used as a diagnostic tool, e.g., to screen individual samples (such as isolated cells, blood, synovial fluid, sera, biopsies, and the like) for the presence of the protein biomarkers of the invention in order to predict whether said patient is at risk of not responding to SAHA based therapy. The protein array can also include antibodies as well as other ligands, e.g., that bind to the protein biomarkers of the invention. Methods of producing polypeptide arrays are described, e.g., in De Wildt et al., 2000, Nature Biotech. 18:989-994; Lueking et al., 1999, Anal. Biochem. 270:103-111; Ge, 2000, Nuc. Acids Res. 28:e3; MacBeath and Schreiber, 2000, Science 289:1760-1763; International Publication Nos. WO 01/40803 and WO 99/51773A1; and U.S. Pat. No. 6,406,921. Polypeptides for the array can be spotted at high speed, e.g., using commercially available robotic apparatus, e.g., from Genetic Micro-Systems and Affymetrix (Santa Clara, Calif., USA) or BioRobotics (Cambridge, UK). The array substrate can be, for example, nitrocellulose, plastic, glass, e.g., surface-modified glass. The array can also include a porous matrix, e.g., acrylamide, agarose, or another polymer.

Preferably, the array is an array of antibodies, e.g., as described in De Wildt, supra. For example, the array can be an array of antibodies, e.g., as described in De Wildt, supra. Cells that produce the polypeptide ligands that bind the protein biomarkers of the invention can be grown on a filter in an arrayed format. Polypeptide production is induced, and the expressed antibodies are immobilized to the filter at the location of the cell. Information about the extent of binding at each address of the array can be stored as a profile, e.g., in a computer database.

In one embodiment the array is an array of protein biomarkers of the invention. In one aspect, the invention provides for antibodies that are bound to an array which selectively bind to the protein biomarkers of the invention.
Protein Production Standard recombinant nucleic acid methods can be used to express a polypeptide or an antibody for use in the methods of the invention. Generally, a nucleic acid sequence encoding, for example, STAT-1 protein is cloned into a nucleic acid expression vector. Of course, if the protein includes multiple polypeptide chains, each chain must be cloned into an expression vector, e.g., the same or different vectors, that are expressed in the same or different cells. If the protein is sufficiently small, i.e., the protein is a peptide of less than 50 amino acids, the protein can be synthesized using automated organic synthetic methods. Methods for producing antibodies directed to a protein biomarker of the invention are well known to one skilled in the art.

The expression vector for expressing the target polypeptide can include, in addition to the segment encoding the polypeptide or fragment thereof, regulatory sequences, including for example, a promoter, operably linked to the nucleic acid(s) of interest. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXTI, pSG (Stratagene) pSVK3, pBPV, pMSG, and pSVL (Pharmacia).

Methods well known to those skilled in the art can be used to construct vectors containing a polynucleotide of the invention and appropriate transcriptional/translational control signals. These methods include in vitro recombinant DNA techniques, synthetic techniques and in vivo recombination/genetic recombination. See, for example, the techniques described in Sambrook & Russell, Molecular Cloning: A Laboratory Manual, 3.sup.rd Edition, Cold Spring Harbor Laboratory, N.Y. (2001) and Ausubel et al., Current Protocols in Molecular Biology (Greene Publishing Associates and Wiley Interscience, N.Y. (1989). Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda P, and trc. Eukaryotic promoters include CMV immediate early, HSV thymidine kinase, early and late SV40, LTRs from retrovirus, mouse metallothionein-I, and various art-known tissue specific promoters. The promoter may be one of an inducible promoter, a constitutive promoter or a tissue-specific promoter.

Generally, recombinant expression vectors will include origins of replication and selectable markers permitting transformation of the host cell, e.g., the ampicillin resistance gene of $E.$ $coli$ and $S.$ $cerevisiae$ auxotrophic markers (such as URA3, LEU2, HIS3, and TRP1 genes), and a promoter derived from a highly expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The polynucleotide of the invention is assembled in appropriate phase with translation initiation and termination sequences, and preferably, a leader sequence capable of directing secretion of translated protein into the periplasmic space or extracellular medium. Optionally, a nucleic acid of the invention can encode a fusion protein including an N-terminal identification peptide imparting desired characteristics, e.g., stabilization or simplified purification of expressed recombinant product. Useful expression-vectors for bacteria are constructed by inserting a polynucleotide of the invention together with suitable translation initiation and termination signals, optionally in operable reading phase with a functional promoter. The vector will comprise one or more phenotypic selectable markers and an origin of replication to ensure maintenance of the vector and to, if desirable, provide amplification within the host. Suitable prokaryotic hosts for transformation include $E.$ $coli,$ $Bacillus$ $subtilis,$ $Salmonella$ $typhimurium$ and various species within the genera $Pseudomonas,$ $Streptomyces$, and $Staphylococcus$, although others may also be employed as a matter of choice.

As a representative but nonlimiting example, useful expression vectors for bacteria can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega, Madison, Wis., USA).

Suitable host cells genetically engineered to contain the polynucleotides of the invention are also known. For example, such host cells contain nucleic acids encoding, for example a protein biomarker of the invention, introduced into the host cell using known transformation, transfection or infection methods, which have been genetically engineered to express the polynucleotides of the invention, wherein such polynucleotides are in operative association with a regulatory sequence heterologous to the host cell which drives expression of the polynucleotides in the cell. The host cell can be a eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected, for example, by calcium phosphate transfection, DEAE, dextran mediated transfection, or electroporation (Davis, L. et al., Basic Methods in Molecular Biology (1986)). Cell-free translation systems can also be employed to produce such proteins using RNAs derived from the DNA constructs of the present invention.

Any host/vector system can be used to express one or more of the protein biomarkers of the invention for use in arrays etc. Appropriate cloning and expression vectors for use with prokaryotic and eukaryotic hosts are described by Sambrook et al., in Molecular Cloning: A Laboratory Manual, Second Edition, Cold Spring Harbor, N.Y. (1989), the disclosure of which is incorporated herein by reference in its entirety. The most preferred host cells are those which do not normally express the particular polypeptide or which expresses the polypeptide at low natural level.

Various mammalian cell culture systems can also be employed to express a recombinant protein. Examples of mammalian expression systems include the monkey COS cells such as COS-7 lines of monkey kidney fibroblasts, described by Gluzman, 1981, Cell 23:175 (1981), Chinese Hamster Ovary (CHO) cells, human kidney 293 cells, human epidermal A431 cells, human Colo205 cells, 3T3 cells, CV-1 cells, normal diploid cells, cell strains derived from in vitro culture of primary tissue, primary explants, HeLa cells, mouse L cells, BHK, HL-60, U937, HaK, C127, 3T3, or Jurkat cells, and other cell lines capable of expressing a compatible vector. Mammalian expression vectors will comprise an origin of replication, a suitable promoter and also any necessary ribosome-binding sites, polyadenylation site, splice donor and acceptor sites, transcriptional termination sequences, and 5' flanking nontranscribed sequences.

Microbial cells employed in expression of proteins can be disrupted by any convenient method, including freeze-thaw cycling, sonication, mechanical disruption, or use of cell lysing agents. Recombinant polypeptides produced in bacterial culture are usually isolated by initial extraction from cell pellets, followed by one or more salting-out, aqueous ion exchange or size exclusion chromatography steps.

Recombinant proteins can be isolated using techniques well-known in the art. Scopes (Protein Purification: Principles and Practice, Springer-Verlag, New York (1994)), for example, provides a number of general methods for purifying recombinant (and non-recombinant) proteins. The methods include, e.g., ion-exchange chromatography, size-exclusion chromatography, affinity chromatography, selective precipitation, dialysis, and hydrophobic interaction chromatography.

Antibodies that specifically bind one or more protein biomarkers of the invention can be obtained from any known source. Most of such antibodies are commercially available. Alternatively, antibodies that specifically bind to one or more protein products of one or more biomarkers of the invention can be produced by any method known in the art for the synthesis of antibodies, in particular, by chemical synthesis or preferably, by recombinant expression techniques.

Antibodies include, but are not limited to, polyclonal antibodies, monoclonal antibodies, bispecific antibodies, multi-specific antibodies, human antibodies, humanized antibodies, camelized antibodies, chimeric antibodies, single-chain Fvs (scFv) (see e.g., Bird et al. (1988) Science 242:423-426; and Huston et al. (1988) Proc. Natl. Acad. Sci. USA 85:5879-5883), single chain antibodies, single domain antibodies, Fab fragments, F(ab') fragments, disulfide-linked Fvs (sdFv), and anti-idiotypic (anti-Id) antibodies (including, e.g., anti-Id antibodies to antibodies of the invention), and epitope-binding fragments of any of the above.

Polyclonal antibodies that specifically bind to an antigen, e.g., one or more of STAT-1, STAT-3 and/or STAT-5 including functionally effective fragments thereof can be produced by various procedures well-known in the art. For example, a human antigen can be administered to various host animals including, but not limited to, rabbits, mice, rats, etc. to induce the production of sera containing polyclonal antibodies specific for the human antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *corynebacterium parvum*. Such adjuvants are also well known in the art.

The term "monospecific antibody" refers to an antibody that displays a single binding specificity and affinity for a particular target, e.g., epitope. This term includes monoclonal antibodies, specific, for example, STAT-1. Such monoclonal antibodies can be prepared using a wide variety of techniques known in the art including the use of hybridoma, recombinant, and phage display technologies, or a combination thereof. See, e.g., U.S. Pat. Nos. RE 32,011; 4,902,614; 4,543,439; 4,411,993 and 4,196,265; Kennett et al (eds.), Monoclonal Antibodies, Hybridomas: A New Dimension in Biological Analyses, Plenum Press (1980); and Harlow and Lane (eds.), Antibodies: A Laboratory Manual, Cold Spring Harbor Laboratory Press (1988), which are incorporated herein by reference. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). Other techniques that enable the production of antibodies through recombinant techniques (e.g., techniques described by William D. Huse et al., 1989, Science, 246: 1275-1281; L. Sastry et al., 1989, Proc. Natl. Acad. Sci. USA, 86: 5728-5732; and Michelle Alting-Mees et al., Strategies in Molecular Biology, 3: 1-9 (1990) involving a commercial system available from Stratacyte, La Jolla, Calif.) may also be utilized to construct monoclonal antibodies. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with a protein product of a biomarker of the invention, and once an immune response is detected, e.g., antibodies specific for the protein are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. Additionally, a RIMMS (repetitive immunization multiple sites) technique can be used to immunize an animal (Kilpatrick et al., 1997, Hybridoma 16:381-9, incorporated by reference in its entirety). The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones. Antibody fragments which recognize specific epitopes of a protein biomarker of the invention may be generated by any technique known to those of skill in the art.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lamba constant regions. Preferably, the vectors for expressing the VH or VL domains comprise an EF-1.alpha promoter, a secretion signal, a cloning site for the variable domain, constant domains, and a selection marker such as neomycin. The VH and VL domains may also cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art. For some uses, including in vivo use of antibodies in humans and in vitro detection assays, it may be preferable to use human or chimeric antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and Intentional Publication Nos. WO 98/46645, WO 98/50433, WO 98/24893, WO 98/16654, WO 96/34096, WO 96/33735, and WO 91/10741; each of which is incorporated herein by reference in its entirety. Antibodies can also be produced by a transgenic animal. U.S. Pat. No. 5,849,992, for example, describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

Once an antibody molecule has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies or fragments thereof may be fused to heterologous polypeptide sequences known in the art to facilitate purification.

Variations, modifications, and other implementations of what is described herein will occur to those of ordinary skill in the art without departing from the spirit and scope of the invention.

Polynucleotides Used to Measure the Products of the Biomarkers of the Invention

Polynucleotides capable of specifically or selectively binding to the mRNA transcripts encoding the polypeptide biomarkers of the invention are also contemplated. For example: oligonucleotides, cDNA, DNA, RNA, PCR products, synthetic DNA, synthetic RNA, or other combinations of naturally occurring or modified nucleotides which specifically and/or selectively hybridize to one or more of the RNA products of the biomarker of the invention are useful in accordance with the invention. "RNA products of the invention" and "genes of the invention" refer to the nucleic acid molecules encoding any one or more of the disclosed polypeptide biomarkers of the invention.

In a preferred embodiment, the oligonucleotides, cDNA, DNA, RNA, PCR products, synthetic DNA, synthetic RNA, or other combinations of naturally occurring or modified nucleotides oligonucleotides which both specifically and selectively hybridize to one or more of the RNA products of the biomarker of the invention are used.

To determine the (increased or decreased) expression levels of genes in the practice of the present invention, any method known in the art may be utilized. In one preferred embodiment of the invention, expression based on detection of RNA which hybridizes to the genes identified and disclosed herein is used. This is readily performed by any RNA detection or amplification method known or recognized as equivalent in the art such as, but not limited to, reverse transcription-PCR, the methods disclosed in U.S. patent application Ser. No. 10/062,857 (filed on Oct. 25, 2001) as well as U.S. Provisional Patent Application 60/298,847 (filed Jun. 15, 2001) and 60/257,801 (filed Dec. 22, 2000), and methods to detect the presence, or absence, of RNA stabilizing or destabilizing sequences.

Alternatively, expression based on detection of DNA status may be used. Detection of the DNA of an identified gene as may be used for genes that have increased expression in correlation with a particular cancer outcome. This may be readily performed by PCR based methods known in the art, including, but not limited to, Q-PCR. Conversely, detection of the DNA of an identified gene as amplified may be used for genes that have increased expression in correlation with a particular treatment outcome. This may be readily performed by PCR based, fluorescent in situ hybridization (FISH) and chromosome in situ hybridization (CISH) methods known in the art.

A. Techniques to Measure the RNA Products of the Biomarkers of the Invention

1. Array Hybridization

In one embodiment of the invention, the polynucleotide used to measure the RNA products of the invention can be used as nucleic acid members stably associated with a support to comprise an array according to one aspect of the invention. The length of a nucleic acid member can range from 8 to 1000 nucleotides in length and are chosen so as to be specific for the RNA products of the biomarkers of the invention. In one embodiment, these members are selective for the RNA products of the invention. The nucleic acid members may be single or double stranded, and/or may be oligonucleotides or PCR fragments amplified from cDNA. Preferably oligonucleotides are approximately 20-30 nucleotides in length. ESTs are preferably 100 to 600 nucleotides in length. It will be understood to a person skilled in the art that one can utilize portions of the expressed regions of the biomarkers of the invention as a probe on the array. More particularly oligonucleotides complementary to the genes of the invention and or cDNA or ESTs derived from the genes of the invention are useful. For oligonucleotide based arrays, the selection of oligonucleotides corresponding to the gene of interest which are useful as probes is well understood in the art. More particularly it is important to choose regions which will permit hybridization to the target nucleic acids. Factors such as the Tm of the oligonucleotide, the percent GC content, the degree of secondary structure and the length of nucleic acid are important factors. See for example U.S. Pat. No. 6,551,784.

B Construction of a Nucleic Acid Array

In the proposed methods, an array of nucleic acid members stably associated with the surface of a substantially support is contacted with a sample comprising target nucleic acids under hybridization conditions sufficient to produce a hybridization pattern of complementary nucleic acid members/target complexes in which one or more complementary nucleic acid members at unique positions on the array specifically hybridize to target nucleic acids. The identity of target nucleic acids which hybridize can be determined with reference to location of nucleic acid members on the array.

The nucleic acid members may be produced using established techniques such as polymerase chain reaction (PCR) and reverse transcription (RT). These methods are similar to those currently known in the art (see e.g., *PCR Strategies*, Michael A. Innis (Editor), et al. (1995) and *PCR: Introduction to Biotechniques Series*, C. R. Newton, A. Graham (1997)). Amplified nucleic acids are purified by methods well known in the art (e.g., column purification or alcohol precipitation). A nucleic acid is considered pure when it has been isolated so as to be substantially free of primers and incomplete products produced during the synthesis of the desired nucleic acid. Preferably, a purified nucleic acid will also be substantially free of contaminants which may hinder or otherwise mask the specific binding activity of the molecule.

An array, according to one aspect of the invention, comprises a plurality of nucleic acids attached to one surface of a support at a density exceeding 20 different nucleic acids/cm2, wherein each of the nucleic acids is attached to the surface of the support in a non-identical pre-selected region (e.g. a microarray). Each associated sample on the array comprises a nucleic acid composition, of known identity, usually of known sequence, as described in greater detail below. Any conceivable substrate may be employed in the invention.

In one embodiment, the nucleic acid attached to the surface of the support is DNA. In a preferred embodiment, the nucleic acid attached to the surface of the support is cDNA or RNA. In another preferred embodiment, the nucleic acid attached to the surface of the support is cDNA synthesized by polymerase chain reaction (PCR). Preferably, a nucleic acid member in the array, according to the invention, is at least 10, 25 or 50 nucleotides in length. In one embodiment, a nucleic acid member is at least 150 nucleotides in length. Preferably, a nucleic acid member is less than 1000 nucleotides in length. More preferably, a nucleic acid member is less than 500 nucleotides in length.

In the arrays of the invention, the nucleic acid compositions are stably associated with the surface of a support, where the support may be a flexible or rigid support. By "stably associated" is meant that each nucleic acid member maintains a unique position relative to the support under hybridization and washing conditions. As such, the samples are non-covalently or covalently stably associated with the support surface. Examples of non-covalent association include non-specific adsorption, binding based on electrostatic interactions (e.g., ion pair interactions), hydrophobic interactions, hydrogen bonding interactions, specific binding through a specific binding pair member covalently attached to the support surface, and the like. Examples of covalent binding include covalent bonds formed between the nucleic acids and a functional group present on the surface of the rigid support (e.g., —OH), where the functional group may be naturally occurring or present as a member of an introduced linking group, as described in greater detail below.

The amount of nucleic acid present in each composition will be sufficient to provide for adequate hybridization and detection of target nucleic acid sequences during the assay in which the array is employed. Generally, the amount of each nucleic acid member stably associated with the support of the array is at least about 0.001 ng, preferably at least about 0.02 ng and more preferably at least about 0.05 ng, where the amount may be as high as 1000 ng or higher, but will usually not exceed about 20 ng. Where the nucleic acid member is "spotted" onto the support in a spot comprising an overall circular dimension, the diameter of the "spot" will generally range from about 10 to 5,000 μm, usually from about 20 to 2,000 μm and more usually from about 100 to 200 μm.

Control nucleic acid members may be present on the array including nucleic acid members comprising oligonucleotides or nucleic acids corresponding to genomic DNA, housekeeping genes, vector sequences, plant nucleic acid sequence, negative and positive control genes, and the like. Control nucleic acid members are calibrating or control genes whose function is not to tell whether a particular "key" gene of interest is expressed, but rather to provide other useful information, such as background or basal level of expression.

Other control nucleic acids are spotted on the array and used as target expression control nucleic acids and mismatch control nucleotides to monitor non-specific binding or cross-hybridization to a nucleic acid in the sample other than the target to which the probe is directed. Mismatch probes thus indicate whether a hybridization is specific or not. For example, if the target is present, the perfectly matched probes should be consistently brighter than the mismatched probes. In addition, if all control mismatches are present, the mismatch probes are used to detect a mutation.

Spotting Method

In one aspect, the invention provides for arrays where each nucleic acid member comprising the array is spotted onto a support.

Preferably, spotting is carried out as follows. PCR products (Ã40 ul) biomarkers of the invention, in the same 96-well tubes used for amplification, are precipitated with 4 ul (1/10 volume) of 3M sodium acetate (pH 5.2) and 100 ul (2.5 volumes) of ethanol and stored overnight at −20° C. They are then centrifuged at 3,300 rpm at 4° C. for 1 hour. The obtained pellets are washed with 50 ul ice-cold 70% ethanol and centrifuged again for 30 minutes. The pellets are then air-dried and resuspended well in 20 ul 3×SSC or in 50% dimethylsulfoxide (DMSO) overnight. The samples are then spotted, either singly or in duplicate, onto slides using a robotic GMS 417 or 427 arrayer (Affymetrix, Ca).

The boundaries of the spots on the microarray may be marked with a diamond scriber (as the spots become invisible after post-processing). The arrays are rehydrated by suspending the slides over a dish of warm particle free ddH$_2$O for approximately one minute (the spots will swell slightly but will not run into each other) and snap-dried on a 70-80° C. inverted heating block for 3 seconds. Nucleic acid is then UV crosslinked to the slide (Stratagene, Stratalinker, 65 mj—set display to "650" which is 650×100 uJ) or the array is baked at 80° C. for two to four hours prior to hybridization. The arrays are placed in a slide rack. An empty slide chamber is prepared and filled with the following solution: 3.0 grams of succinic anhydride (Aldrich) was dissolved in 189 ml of 1-methyl-2-pyrrolidinone (rapid addition of reagent is crucial); immediately after the last flake of succinic anhydride is dissolved, -21.0 ml of 0.2 M sodium borate is mixed in and the solution is poured into the slide chamber. The slide rack is plunged rapidly and evenly in the slide chamber and vigorously shaken up and down for a few seconds, making sure the slides never leave the solution, and then mixed on an orbital shaker for 15-20 minutes. The slide rack is then gently plunged in 95° C. ddH$_2$O for 2 minutes, followed by plunging five times in 95% ethanol. The slides are then air dried by allowing excess ethanol to drip onto paper towels. The arrays are stored in the slide box at room temperature until use.

Numerous methods may be used for attachment of the nucleic acid members of the invention to the substrate (a process referred to as "spotting"). For example, nucleic acids are attached using the techniques of, for example U.S. Pat. No. 5,807,522, which is incorporated herein by reference, for teaching methods of polymer attachment. Alternatively, spotting may be carried out using contact printing technology as is known in the art.

The measuring of the expression of the RNA product of the invention can be done by using those polynucleotides which are specific and/or selective for the RNA products of the invention to quantitate the expression of the RNA product. In a specific embodiment of the invention, the polynucleotides which are specific and/or selective for the RNA products are probes or primers. In one embodiment, these polynucleotides are in the form of nucleic acid probes which can be spotted onto an array to measure RNA from the blood of an individual to be diagnosed. In another embodiment, commercial arrays can be used to measure the expression of the RNA product. In yet another embodiment, the polynucleotides which are specific and/or selective for the RNA products of the invention are used in the form of probes and primers in techniques such as quantitative real-time RT PCR, using for example SYBR®Green, or using TaqMan® or Molecular Beacon techniques, where the polynucleotides used are used in the form of a forward primer, a reverse primer, a TaqMan® labeled probe or a Molecular Beacon labeled probe.

In embodiments where only one or a two genes are to be analyzed, the nucleic acid derived from the sample cancer cell(s) may be preferentially amplified by use of appropriate primers such that only the genes to be analyzed are amplified to reduce background signals from other genes expressed in the breast cell. Alternatively, and where multiple genes are to be analyzed or where very few cells (or one cell) is used, the nucleic acid from the sample may be globally amplified before hybridization to the immobilized polynucleotides. Of course RNA, or the cDNA counterpart thereof, may be directly labeled and used, without amplification, by methods known in the art.

Use of a Microarray

A "microarray" is a linear or two-dimensional array of preferably discrete regions, each having a defined area, formed on the surface of a solid support such as, but not limited to, glass, plastic, or synthetic membrane. The density of the discrete regions on a microarray is determined by the total numbers of immobilized polynucleotides to be detected on the surface of a single solid phase support, preferably at least about 50/cm$^2$, more preferably at least about 100/cm$^2$, even more preferably at least about 500/cm$^2$, but preferably below about 1,000/cm$^2$. Preferably, the arrays contain less than about 500, about 1000, about 1500, about 2000, about 2500, or about 3000 immobilized polynucleotides in total. As used herein, a DNA microarray is an array of oligonucleotides or polynucleotides placed on a chip or other surfaces used to hybridize to amplified or cloned polynucleotides from a sample. Since the position of each particular group of primers in the array is known, the identities of a sample polynucleotides can be determined based on their binding to a particular position in the microarray.

Determining gene expression levels may be accomplished utilizing microarrays. Generally, the following steps may be involved: (a) obtaining an mRNA sample from a subject and preparing labeled nucleic acids therefrom (the "target nucleic acids" or "targets"); (b) contacting the target nucleic acids with an array under conditions sufficient for the target nucleic acids to bind to the corresponding probes on the array, for example, by hybridization or specific binding; (c) optional removal of unbound targets from the array; (d) detecting the bound targets, and (e) analyzing the results, for example, using computer based analysis methods. As used herein, "nucleic acid probes" or "probes" are nucleic acids attached to the array, whereas "target nucleic acids" are nucleic acids that are hybridized to the array.

Nucleic acid specimens may be obtained from a subject to be tested using either "invasive" or "non-invasive" sampling means. A sampling means is said to be "invasive" if it involves the collection of nucleic acids from within the skin or organs of an animal (including murine, human, ovine, equine, bovine, porcine, canine, or feline animal). Examples of invasive methods include, for example, blood collection, semen collection, needle biopsy, pleural aspiration, umbilical cord biopsy. Examples of such methods are discussed by Kim, et al., (J. Virol. 66:3879-3882, 1992); Biswas, et al., (Ann. NY Acad. Sci. 590:582-583, 1990); and Biswas, et al., (J. Clin. Microbiol. 29:2228-2233, 1991).

In contrast, a "non-invasive" sampling means is one in which the nucleic acid molecules are recovered from an internal or external surface of the animal. Examples of such "non-invasive" sampling means include, for example, "swabbing," collection of tears, saliva, urine, fecal material etc.

In one embodiment of the present invention, one or more cells from the subject to be tested are obtained and RNA is isolated from the cells. In a preferred embodiment, a sample of T cells is obtained from the subject. It is also possible to obtain a cell sample from a subject, and then to enrich the sample for a desired cell type. For example, cells may be isolated from other cells using a variety of techniques, such as isolation with an antibody binding to an epitope on the cell surface of the desired cell type. Where the desired cells are in a solid tissue, particular cells may be dissected, for example, by microdissection or by laser capture microdissection (LCM) (see, e.g., Bonner, et al., Science 278:1481, 1997; Emmert-Buck, et al., Science 274:998, 1996; Fend, et al., Am. J. Path. 154:61, 1999; and Murakami, et al., Kidney hit. 58:1346, 2000).

RNA may be extracted from tissue or cell samples by a variety of methods, for example, guanidium thiocyanate lysis followed by CsCl centrifugation (Chirgwin, et al., Biochemistry 18:5294-5299, 1979). RNA from single cells may be obtained as described in methods for preparing cDNA libraries from single cells (see, e.g., Dulac, Curr. Top. Dev. Biol. 36:245, 1998; Jena, et al., J. Immunol. Methods 190:199, 1996).

The RNA sample can be further enriched for a particular species. In one embodiment, for example, poly(A)+RNA may be isolated from an RNA sample. In another embodiment, the RNA population may be enriched for sequences of interest by primer-specific cDNA synthesis, or multiple rounds of linear amplification based on cDNA synthesis and template-directed in vitro transcription (see, e.g., Wang, et al., Proc. Natl. Acad. Sci. USA 86:9717, 1989; Dulac, et al., supra; Jena, et al., supra). In addition, the population of RNA, enriched or not in particular species or sequences, may be further amplified by a variety of amplification methods including, for example, PCR; ligase chain reaction (LCR) (see, e.g., Wu and Wallace, Genomics 4:560, 1989; Lande-gren, et al., Science 241:1077, 1988); self-sustained sequence replication (SSR) (see, e.g., Guatelli, et al., Proc. Natl. Acad. Sci. USA 87:1874, 1990); nucleic acid based sequence amplification (NASBA) and transcription amplification (see, e.g., Kwoh, et al., Proc. Natl. Acad. Sci. USA 86:1173, 1989). Methods for PCR technology are well known in the art (see, e.g., PCR Technology: Principles and Applications for DNA Amplification (ed. H. A. Erlich, Freeman Press, N.Y., N.Y., 1992); PCR Protocols: A Guide to Methods and Applications (eds. Innis, et al., Academic Press, San Diego, Calif., 1990); Mattila, et al., Nucleic Acids Res. 19:4967, 1991; Eckert, et al., PCR Methods and Applications 1: 17, 1991; PCR (eds. McPherson et al., IRL Press, Oxford); and U.S. Pat. No. 4,683,202). Methods of amplification are described, for example, by Ohyama, et al., (BioTechniques 29:530, 2000); Luo, et al., (Nat. Med. 5:117, 1999); Hegde, et al., (BioTechniques 29:548, 2000); Kacharmina, et al., (Meth. Enzymol. 303:3, 1999); Livesey, et al., Curr. Biol. 10:301, 2000); Spirin, et al., (Invest. Ophtalmol. Vis. Sci. 40:3108, 1999); and Sakai, et al., (Anal. Biochem. 287:32, 2000). RNA amplification and cDNA synthesis may also be conducted in cells in situ (see, e.g., Eberwine, et al. Proc. Natl. Acad. Sci. USA 89:3010, 1992).

In yet another embodiment of the invention proposes all or part of a disclosed sequence may be amplified and detected by methods such as the polymerase chain reaction (PCR) and variations thereof, such as, but not limited to, quantitative PCR (Q-PCR), reverse transcription PCR(RT-PCR), and real-time PCR, optionally real-time RT-PCR. Such methods would utilize one or two primers that are complementary to portions of a disclosed sequence, where the primers are used to prime nucleic acid synthesis.

The newly synthesized nucleic acids are optionally labeled and may be detected directly or by hybridization to a polynucleotide of the invention.

The nucleic acid molecules may be labeled to permit detection of hybridization of the nucleic acid molecules to a microarray. That is, the probe may comprise a member of a signal producing system and thus, is detectable, either directly or through combined action with one or more additional members of a signal producing system. For example, the nucleic acids may be labeled with a fluorescently labeled dNTP (see, e.g., Kricka, 1992, Nonisotopic DNA Probe Techniques, Academic Press San Diego, Calif.), biotinylated dNTPs or rNTP followed by addition of labeled streptavidin, chemiluminescent labels, or isotopes. Another example of labels include "molecular beacons" as described in Tyagi and Kramer (Nature Biotech. 14:303, 1996). The newly synthesized nucleic acids may be contacted with polynucleotides (containing sequences) of the invention under conditions which allow for their hybridization. Hybridization may also be determined, for example, by plasmon resonance (see, e.g., Thiel, et al. Anal. Chem. 69:4948, 1997).)

In one embodiment, a plurality e.g., 3 sets of target nucleic acids are labeled and used in one hybridization reaction ("multiplex" analysis). For example, one set of nucleic acids may correspond to RNA from one cell and another set of nucleic acids may correspond to RNA from another cell. The plurality of sets of nucleic acids may be labeled with different labels, for example, different fluorescent labels (e.g., fluorescine and rhodamine) which have distinct emission spectra so that they can be distinguished. The sets may then be mixed and hybridized simultaneously to one microarray (see, e.g., Shena, et al., Science 270:467-470, 1995).

A number of different microarray configurations and methods for their production are known to those of skill in the art and are disclosed in U.S. Pat. Nos. 5,242,974; 5,384,261;

5,405,783; 5,412,087; 5,424,186; 5,429,807; 5,436,327; 5,445,934; 5,556,752; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,624,711; 5,700,637; 5,744,305; 5,770,456; 5,770,722; 5,837,832; 5,856,101; 5,874,219; 5,885,837; 5,919,523; 6,022,963; 6,077,674; and 6,156,501; Shena, et al., Tibtech 16:301, 1998; Duggan, et al., Nat. Genet. 21:10, 1999; Bowtell, et al., Nat. Genet. 21:25, 1999; Lipshutz, et al., 21 Nature Genet. 20-24, 1999; Blanchard, et al., 11 Biosensors and Bioelectronics, 687-90, 1996; Maskos, et al., 21 Nucleic Acids Res. 4663-69, 1993; Hughes, et al., Nat. Biotechol. (2001) 19:342; the disclosures of which are herein incorporated by reference. Patents describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,848,659; and 5,874,219; the disclosures of which are herein incorporated by reference.

Arrays preferably include control and reference nucleic acids. Control nucleic acids include, for example, prokaryotic genes such as bioB, bioC and bioD, cre from P1 bacteriophage or polyA controls, such as dap, lys, phe, thr, and trp. Reference nucleic acids allow the normalization of results from one experiment to another and the comparison of multiple experiments on a quantitative level. Exemplary reference nucleic acids include housekeeping genes of known expression levels, for example, GAPDH, hexokinase, and actin.

In one embodiment, an array of oligonucleotides may be synthesized on a solid support. Exemplary solid supports include glass, plastics, polymers, metals, metalloids, ceramics, organics, etc. Using chip masking technologies and photoprotective chemistry, it is possible to generate ordered arrays of nucleic acid probes. These arrays, which are known, for example, as "DNA chips" or very large scale immobilized polymer arrays ("VLSIPS®" arrays), may include millions of defined probe regions on a substrate having an area of about 1 $cm^2$ to several $cm^2$, thereby incorporating from a few to millions of probes (see, e.g., U.S. Pat. No. 5,631,734).

To compare expression levels, labeled nucleic acids may be contacted with the array under conditions sufficient for binding between the target nucleic acid and the probe on the array. In a preferred embodiment, the hybridization conditions may be selected to provide for the desired level of hybridization specificity; that is, conditions sufficient for hybridization to occur between the labeled nucleic acids and probes on the microarray.

Hybridization may be carried out in conditions permitting essentially specific hybridization. The length and GC content of the nucleic acid will determine the thermal melting point and thus, the hyridization conditions necessary for obtaining specific hybridization of the probe to the target nucleic acid. These factors are well known to a person of skill in the art, and may also be tested in assays. An extensive guide to nucleic acid hybridization may be found in Tijssen, et al. (Laboratory Techniques in Biochemistry and Molecular Biology, Vol. 24: Hybridization With Nucleic Acid Probes, P. Tijssen, ed. Elsevier, N.Y., (1993)).

The methods described above will result in the production of hybridization patterns of labeled target nucleic acids on the array surface. The resultant hybridization patterns of labeled nucleic acids may be visualized or detected in a variety of ways, with the particular manner of detection selected based on the particular label of the target nucleic acid. Representative detection means include scintillation counting, autoradiography, fluorescence measurement, calorimetric measurement, light emission measurement, light scattering, and the like.

One such method of detection utilizes an array scanner that is commercially available (Affymetrix, Santa Clara, Calif.), for example, the 417® Arrayer, the 418(Array Scanner, or the Agilent GeneArray® Scanner. This scanner is controlled from a system computer with an interface and easy-to-use software tools. The output may be directly imported into or directly read by a variety of software applications. Preferred scanning devices are described in, for example, U.S. Pat. Nos. 5,143,854 and 5,424,186.

For fluorescent labeled probes, the fluorescence emissions at each site of a transcript array may be, preferably, detected by scanning confocal laser microscopy. Alternatively, a laser may be used that allows simultaneous specimen illumination at wavelengths specific to the two fluorophores and emissions from the two fluorophores may be analyzed simultaneously (see, e.g., Shalon, et al., Genome Res. 6:639-645, 1996). In a preferred embodiment, the arrays may be scanned with a laser fluorescent scanner with a computer controlled X-Y stage and a microscope objective. Fluorescence laser scanning devices are described in Shalon, et al., supra.

Various algorithms are available for analyzing gene expression data, for example, the type of comparisons to perform. In certain embodiments, it is desirable to group genes that are co-regulated. This allows for the comparison of large numbers of profiles. An embodiment thus provides for identifying such groups of genes involves clustering algorithms (for reviews of clustering algorithms, see, e.g., Fukunaga, 1990, Statistical Pattern Recognition, 2nd Ed., Academic Press, San Diego; Everitt, 1974, Cluster Analysis, London: Heinemann Educ. Books; Hartigan, 1975, Clustering Algorithms, New York: Wiley; Sneath and Sokal, 1973, Numerical Taxonomy, Freeman; Anderberg, 1973, Cluster Analysis for Applications, Academic Press: New York).

Articles of Manufacture

The materials and methods of the present invention are ideally suited for preparation of kits produced in accordance with well known procedures. The invention thus provides kits comprising agents (like the polynucleotides and/or antibodies described herein as non-limiting examples) for the detection of expression of the disclosed sequences. Such kits, optionally comprising the agent with an identifying description or label or instructions relating to their use in the methods of the present invention, are provided. Such a kit may comprise containers, each with one or more of the various reagents (typically in concentrated form) utilized in the methods, including, for example, pre-fabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more primer complexes of the present invention (e.g., appropriate length poly(T) or random primers linked to a promoter reactive with the RNA polymerase). A set of instructions will also typically be included.

Thus, a kit for gene expression profiling comprises the reagents and instructions necessary for the gene expression profiling of the claimed biomarker panel. Thus, for example, the reagents may include primers, enzymes, and other reagents for the preparation, detection, and quantitation of cDNAs for the claimed panel of biomarkers. As discussed above, the method of creating cDNA from mRNA in a sample is referred to as the reverse transcriptase polymer chain reaction (RT-PCR). Primers particularly suited for use in gene expression profiling using RT-PCR based on the claimed panel can be easily generated. In addition to the primers, reagents such as one including a dinucleotide triphosphate mixture having all four dinucleotide triphosphates (e.g. dATP, dGTP, dCTP, and dTTP), one having the reverse transcriptase enzyme, and one having a thermostable DNA polymerase are required for RT-PCR. Additionally buffers, inhibitors and activators used for the RT-PCR process are suitable reagents for inclusion in the kit embodiment. Once the cDNA has been sufficiently amplified to a specified end point, the cDNA sample must be prepared for detection and quantitation. One method contemplated for detection of polynucleotides is fluorescence spectroscopy, and therefore chromophores that are suited to fluorescence spectroscopy are desirable for labeling polynucleotides and may also be included in reagents of the kit embodiment. Instructions included with the kit embodiment for gene expression profiling preferably teach the user the following steps: to obtain a biological sample; to isolate cellular RNA from the sample; to amplify copies of cDNA from the sample for each biomarker in the panel, and the panel for which the reagents are provided; and to quantify levels of cDNA amplified from the sample. Though tissue samples from a variety of procedures may be used, the instructions for obtaining a biological sample are preferably whereby the user obtains a sample of colorectal cells in a minimally invasive manner, such as by use of a swab or collection of a stool sample. The instructions may also preferably include the step of comparing the cDNA levels quantified to a control.

An alternative embodiment provides a kit for protein expression profiling which comprises the reagents and instructions necessary for protein expression profiling of the claimed panel. Thus, in this embodiment, the kit for protein expression profiling includes supplying an antibody panel based on the claimed panel of biomarkers for measuring targeted polypeptide levels from a biological sample. One embodiment contemplated for such a panel includes the antibody panel bound to a solid support. Additionally, the reagents included with the kit for protein expression profiling may use a second antibody having specificity to some portion of the bound polypeptide. Such a second antibody may be labeled with molecules useful for detection and quantitation of the bound polypeptides, and therefore in binding to the polypeptide label it for detection and quantitation. Additionally, other reagents are contemplated for labeling the bound polypeptides for detection and quantitation. Such reagents may either directly label the bound polypeptide or, analogous to a second antibody, may be a moiety with specificity for the bound polypeptide having labels. Examples of such moieties include but are not limited to small molecules such as cofactors, substrates, complexing agents, and the like, or large molecules, such as lectins, peptides, olionucleotides, and the like. Such moieties may be either naturally occurring or synthetic. Instructions for the protein expression profiling kit preferably teach the user: to obtain a biological sample; to use the antibody panel supplied with the kit for each biomarker in the panel to bind the polypeptides from the sample; and to quantify levels of polypeptides bound from the sample to the antibody panel. Preferably, the kit instructions also include a step of comparing the polypeptide levels to a control. Preferably the biological sample is obtained by a minimally invasive procedure such as use of a swab to through a stool sample.

In accordance with the above, an embodiment of the invention provides a prognostic protein kit for determining the level of STAT expression containing (i) an antibody capable of binding to phosphorylated STAT protein, e.g., one of STAT-1, -3 or -5 but not to the corresponding unphosphorylated STAT protein; and optionally (ii) a secondary antibody directed against the antibody of step (i) and optionally; (iii) reagents for the measurement of a signal derived from an antibody binding to one of the phosphorylated STAT proteins of the invention.

Examples of reagents referred to under (iii) above can be commonly used enzyme/substrate combinations for detection such as: a) Alkaline Phosphatase as enzyme together with the following substrates: 1. 5-bromo-4-chloro-3-indolyl phosphate (BCIP) and nitroblue tetrazolium(NBT)$_2$. naphtol-AS-MX-phosphate and fast red TR, or fast blue BN, or fast green (BN)3. Vector Red 4. Vector Black 5. Vector Blue 6. Horseradish Peroxidase as enzyme and 3,3-diaminobenzidine tetrahydrochloride (DAB) as substrate WO 2004/029622 PCT/EP2003/010842. Other reagents used may be detected by immunofluorescence such as Fluorescein Isothiocyanate, Phycoerythrin, Green Fluorescent Protein, Red Fluorescent Protein, Yellow Fluorescent Protein, Texas Red, TRIC, Cy3, or Cy5. Other staining techniques can employ e.g. gold, rhodamine.

Having now generally described the invention, the same will be more readily understood through reference to the following examples which are provided by way of illustration, and are not intended to be limiting of the present invention, unless specified.

EXAMPLE 1

Materials and Methods

Cell Lines: Refer to Table 1 for a list of cell lines used in this experiment.

The cell lines used by CMTI (Cell & Molecular Technologies, Inc) for this study were cells identified by Merck & Co, Inc. The cell lines were grown in RPMI 1640/7.5-20% fetal bovine serum/L-Glutamine (Invitrogen) and maintained in a Heraeus HeraCell 240 humidified 5.0% $CO_2$, 37° C. incubator. For in-house studies, cell lines were obtained from the American Type Tissue Culture collection, and maintained in RPMI 1640/10% fetal bovine serum, 1% Glutamax and 1% penicillin-streptomycin (Gibco).

Drug Source Vorinostat was prepared as described in U.S. Pat. Publ. 2004/0122101A1. The compound was provided as a powder and prepared as a 30 mM stock solution in DMSO. Inhibitors of JAk kinases 2-(2-chlorophenyl)-9-fluoro-3,6-dihydro-7H-benzo[h]imidazo[4,5-f]isoquinolin-7-one (Compound A) and JAK 1 inhibitor-2-tert-butyl-9-fluoro-1,6-dihydro-7H-benzo[h]imidazo[4,5-f]isoquinolin-7-one (Compound B) were used in combination studies. Each of Compound A and B is disclosed in US Patent No. U.S. Pat. No. 6,852,727, which issued on Feb. 8, 2005, and details methods of making and using each of Compound A and B. The contents of U.S. Pat. No. 6,852,727 is incorporated by reference herein in its entirety.

Proliferation Assay CellTiter-Blue™ Cell Viability Assay (Promega) was performed on every cell line in this study according to manufacturer's suggested protocol (Promega). For the proliferation assay, cell lines were seeded on 96-well plates (Corning). After 24 hours of plating, the 96-well plates were treated with vorinostat (SAHA) (0, 0.004-30 uM). The CellTiter-Blue Reagent™ was added to each of the wells. Experiments were performed in triplicate. The plates were then placed at 37° C. for two hours, and subsequently read on the Flex Station II 1384 from Molecular Devices. The IC50 values were calculated using the Sigma Plot software. Combination index for the studies to test efficacy of Vorinostat and JAK inhibitors was calculated with CalcuSyn software (is there a web site for this or a reference that describes the software)

Apoptosis assay: ApoONE® Homogeneous Caspase-3/7 Assay (Promega) was performed according to standard protocol (Promega). For the caspase assay cell lines were seeded and treated with vorinostat as previously indicated. After 24 hours of treatment, a volume equal to the media volume in each well of Apo-One Caspase 3/7 lysis was added to each well with cells. The apoptosis assay was then performed according to the manufacturer's instructions. The plates were read on the Flex Station II 384 from Molecular Devices. Where indicated, DNA fragmentation in response to vorinostat was also assessed in some cell lines by TUNEL assay (BD-PharMingen). Briefly, cells were left untreated or treated with vorinostat, JAK inhibitors or combinations at the concentration indicated for 48 h, fixed in 1% paraformaldhyde and processed according to standard procedure. Samples were analyzed by flow cytometry (FACSCalibur).

Cell lysate preparation and Western Blot: Western blot analysis was performed using standard techniques. Exponentially growing cells were collected by centrifugation and washed with PBS. Cells were lysed in Laemmli Sample Buffer (Bio-Rad) with Complete Mini protease inhibitors (Roche) and sonicated twice for 5 seconds at maximum setting with a probe Sonicator (Fisher) on ice. Protein concentration was determined by the Dc Protein Assay (Bio-Rad). Equal amounts (60 ug) were added to each well of a Criterion Tris-HCl gel (Bio-Rad). Electrophoresis was carried out at 100V for 2.5 hours in Novex Tris-glycine SDS Running Buffer (Invitrogen) with Kaleidoscope-Precision Plus Protein Standards (Bio-Rad). Gels were transferred onto Nitrocellulose membranes (Invitrogen) in Novex Tris-glycine Transfer buffer (Invitrogen) with 20% methanol and 0.01% SDS (Fisher) for 1 hour at 100V. The membranes were blocked with 5% Bovine serum albumin (BSA; Sigma) in Tris Buffered Saline (Bio-Rad) Tween 20 (Fisher) (TBS-T) for 30 minutes. The membranes were probed with anti-STAT-1, anti-phosphoserine STAT-1, anti-STAT-3, anti-phosphoserine STAT-3, anti-STAT-5 and with antibodies against the tyrosine-phosphorylated form of these three isoforms (all from Cell Signaling Technology) at a 1:1,000 dilution. Anti-beta actin and anti-total actin (Sigma) were used as loading controls at a 1:5,000 dilution overnight in 5% BSA TBS-T. The next day the membranes were washed with TBS-T and were incubated with secondary antibody, Zymax goat anti-rabbit Cy5 and goat anti-mouse Cy5 (Zymed) at a 1:7,000 dilution for 1 hour in the dark. The blots were washed with TBS-T and fluorescence emission was read on the Typhoon 9410 (Amersham Biosciences). The photomultiplier tubes were adjusted for maximum exposure. Signals were quantified using ImageQuant software and normalized to the loading control total actin. For each of the STAT family members analyzed, protein and phosphorylation levels were expressed as fold over signal for SUPT1 cells, which appeared to be the most sensitive cell line of the lymphoma cell liens tested.

STAT localization by immunofluorescence microscopy: Lymphoma cell lines were spun onto coated slides using Shandon EZ Double Cytofunnels in a Cytospin (Thermo Electron Corp) at either $6.25 \times 10^4$ or $12.5 \times 10^4$ cells in 250 µl at 1000 rpm for 5 minutes. Cells were immediately fixed with 4% paraformaldehyde (Fisher Biotech) for 30 minutes, washed five times with Dulbecco's PBS (Invitrogen) and were permeabilized with ice-cold 0.2% Triton X-100 for 30 minutes. Samples were blocked with 5% Bovine Serum Albumin (BSA) (Sigma) in TBS-Tween 20 for 30 minutes. Primary antibodies: anti-STAT-1, anti-STAT-3 and anti-PSTAT-3 Serine (Cell Signaling Technology) were added at a 1:100 dilution in 2.5% BSA TBS-T and incubated overnight at 4° C. The next day the slides were washed with PBS and the secondary antibody, donkey anti-rabbit IgG (H+L) FITC (Jackson ImmunoResearch Labs) was added at a 1:100 dilution in 0.25% BSA TBS-T for 30 minutes. After 30 minutes the secondary was removed and re-added at a 1:50 dilution with the DNA stain Hoechst 33342 (Molecular Probes) at a 1:1,000 dilution in 0.25% BSA TBS-T for another 30 minutes. The slides were washed and allowed to dry slightly. Prolong Gold Anti-Fade (Molecular Probes) was added prior to mounting the coverslips. Samples were analyzed under a Nikon Eclipse TE2000-U microscope.

Immunohistochemical analysis of STAT1, STAT3 and STAT5 in skin biopsies: Paraffin-embedded tissues were sectioned at 5 µm and stored under nitrogen until immunostained. Sections were dewaxed in xylenes and rehydrated through graded alcohols, and then incubated in 0.3% $H_2O_2$ in methanol for 20 min at room temperature to block endogenous peroxidase activity. Antigen retrieval was performed using a commercially available citrate-based solution (Vector Laboratories, Burlingame, Calif.) according to the manufacturer's instructions. Non-specific binding was blocked by incubation in 10% normal goat serum for 1 h at room temperature. Sections were incubated with polyclonal antibodies directed against Stat1 (Cell Signaling Technology, Danvers, MA, #9175, 1:200 dilution) or Stat5 (Cell Signaling Technology, #9352, 1:1000 dilution), followed by a biotinylated secondary antibody (0.5 µg/ml, Jackson ImmunoResearch, West Grove, Pa.) and ABC/DAB (Vector Laboratories), then hematoxylin counterstaining.

Results and Discussion

Figure 1B:
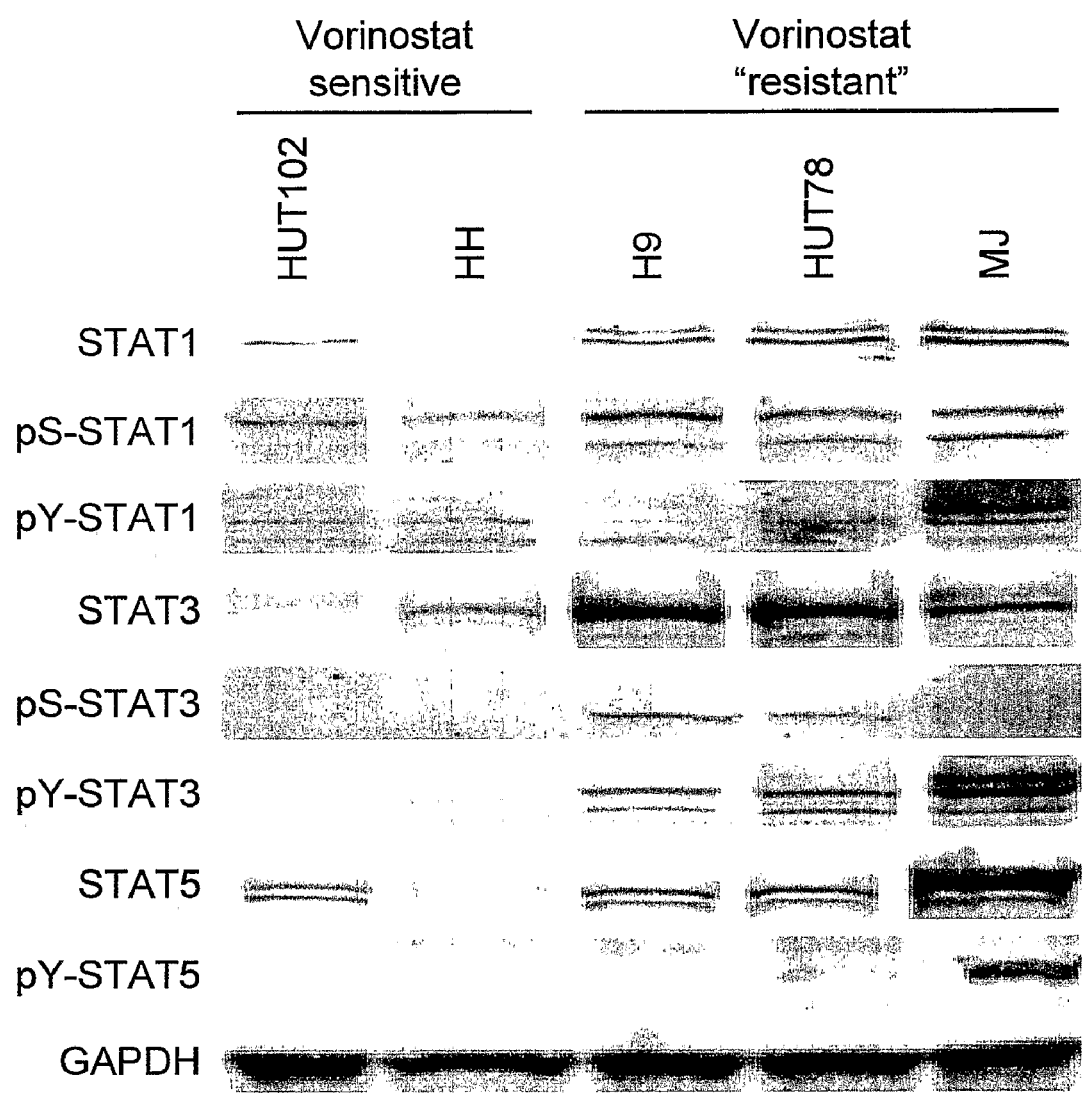
FIG. 1B. Similar analysis was performed across commercially available CTCL lines FIG. 2. Localization of STAT-1 protein by immunofluorescence microscopy. Cells were fixed and stained as indicated in the examples detailed elsewhere in the application. Nuclei were counterstained with Hoechst dye.

The effect of vorinostat on proliferation and apoptosis was assessed in a panel of lymphoma cell lines (Table 1). Cells were ranked according to their response to vorinostat. Lymphoma cell lines in which vorinostat inhibited proliferation with a half-maximal inhibitory concentration (IC50) value below <1 µM and induced apoptosis, as assessed by activation of caspase-3,7 or DNA fragmentation, were classified as sensitive. The expression as well as phosphorylation of STAT-1, STAT-3 and STAT-5 was examined by Western blot performed on whole cell extracts Refer to FIG. 1A. Signals were quantified and normalized to those of SUPT1 cells, the most sensitive cell line to vorinostat treatment among the lymphoma panel (Table 2). The results from this analysis showed subtle differences in STAT3 expression levels, with more profound differences in the expression patterns of STAT1 and STAT5 proteins were markedly higher in the group less responsive to vorinostat. In addition, tyrosine and serine phosphorylation levels of STAT 1, STAT3, and STAT5 were generally elevated in this cell line subset. Because the different cell lines express various combinations of STAT-1, 3 and 5, resistance to vorinostat was better predicted by the examination of the pattern of expression and/or phosphorylation of the STAT proteins. Referring to Table 3, with the exception of STAT3, expression and phosphorylation of the STAT proteins studies was in general at least 2 fold higher in lymphoma cell lines less sensitive to Vorinostat compared to the more sensitive cells line(s). In the clinic, vorinostat has demonstrated efficacy against CTCL. Referring to FIG. 1B, STAT activation was compared specifically in CTCL lines. Western blot analysis performed on whole cell lysates prepared from this focused panel showed a similar correlation between STAT activation and low vorinostat sensitivity as previously observed across the broad lymphoma cell line panel of both B and T cell origin.

The differential expression as well as phosphorylation of STAT proteins in the lymphoma lines observed by Western blot prompted the examination of the localization of STAT-1 and STAT-3 proteins by immunofluorescence microscopy in cells that display high and low sensitivity to vorinostat. Because phosphorylated STAT proteins form dimers that translocate into the nucleus to initiate transcription, the investigation looked to detect differences in the subcellular localization of STAT proteins in the cell lines under investigation.

Figure 2:
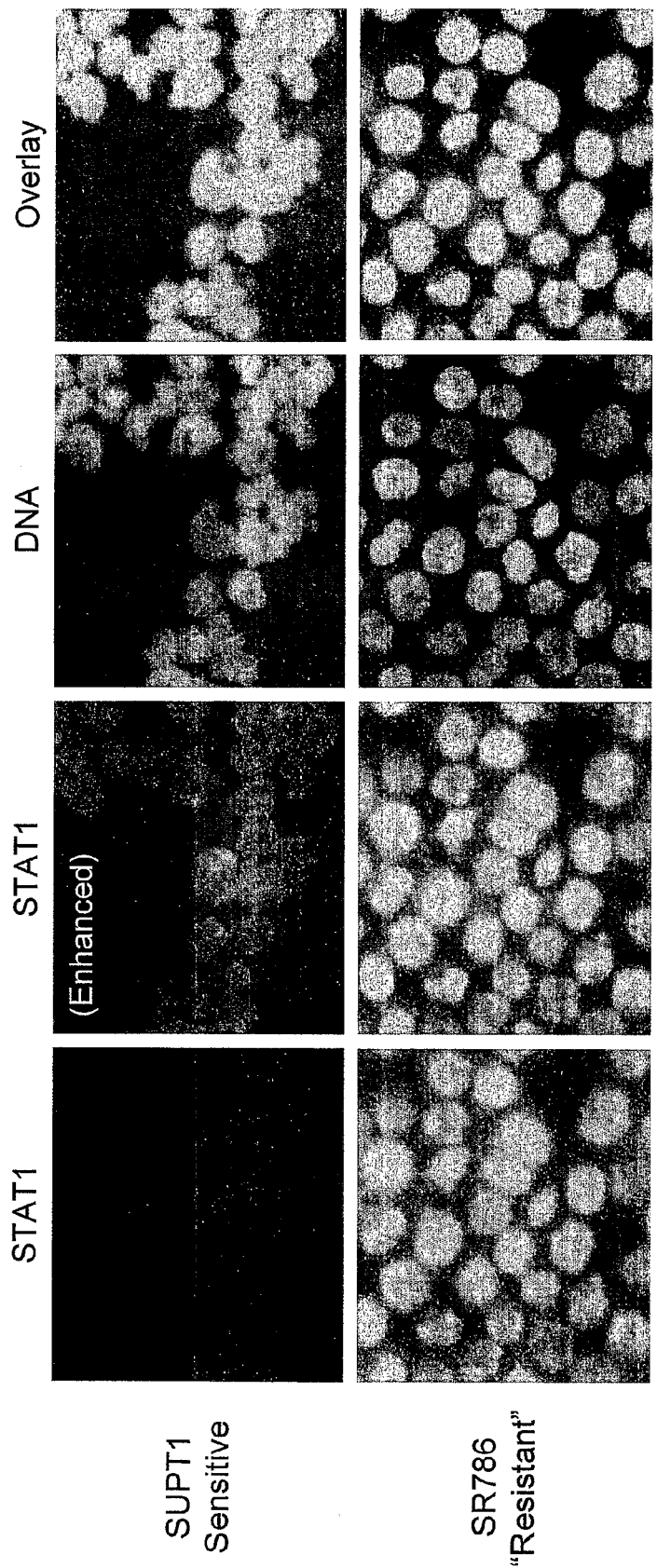

Staining of vorinostat-sensitive SUPT-1 cells with antibodies directed against STAT-1 generated a weak signal which was scattered throughout the cell. Refer to FIG. 2. In contrast, in vorinostat-resistant SR786 cells the intense STAT-1 signal was mainly concentrated to the nuclear compartment. Similar results were obtained with antibodies directed against STAT-3 and serine-phosphorylated STAT-3 (data not shown). Thus, the differences in intensity and localization of the signal observed in the STAT immunostaining experiments are consistent with the results obtained from STAT immunoblotting analysis.

Figure 3A:
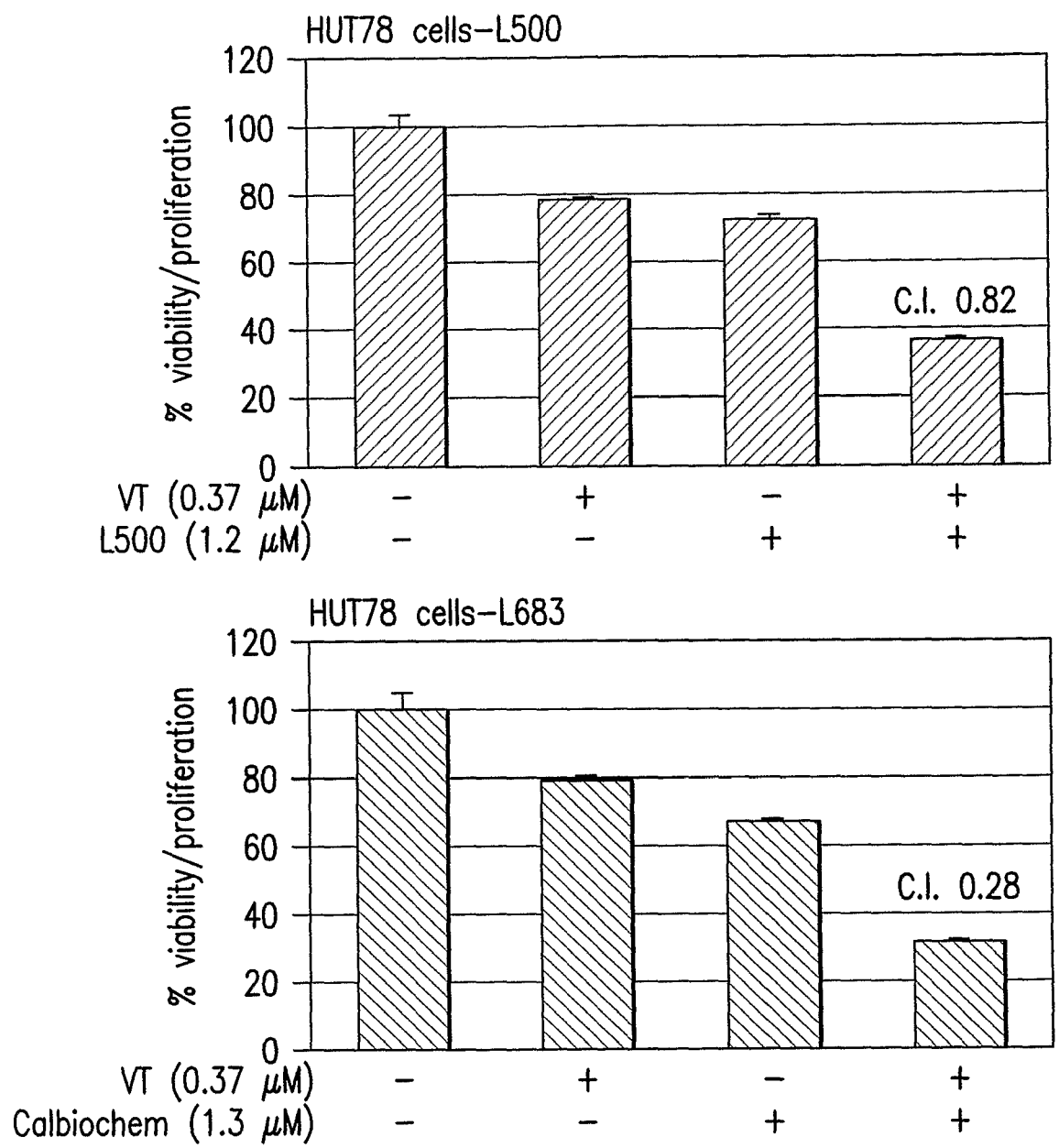
FIG. 3A. Effect of vorinostat in combination with JAK inhibitors. A HUT78 cells were left untreated or treated with the indicated concentrations of vorinostat (VT), JAK inhibitor L500 or JAK inhibitor I (L683) and the combinations for 48 h. Viability was determined as described under "Material and Methods", and expressed as percent of untreated control.
Figure 3B:
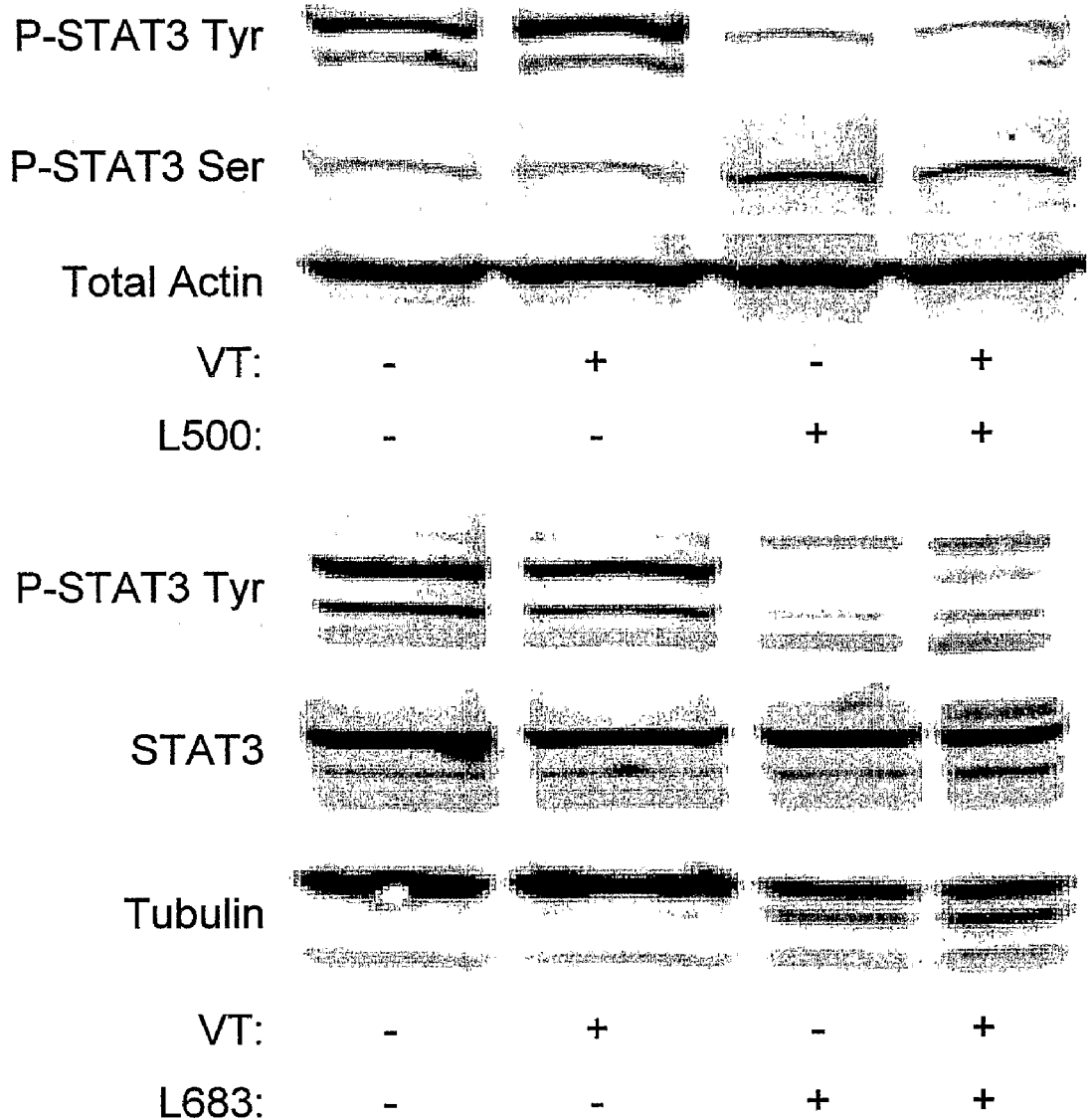
FIG. 3B. Western blot analysis to determine tyrosine phosphorylation status of STAT3 performed on whole cell lysates prepared from cells treated with single agents and combination as indicated. As a control, lysates were probed with anti-pSer-STAT3 and anti-actin or anti-tubulin antibodies.

In order to determine whether elevated STAT activity was functionally linked to resistance to Vorinostat, the effect of vorinostat on cell proliferation was evaluated in combination with compounds that inhibit the JAK family of tyrosine kinases, upstream activators of STAT proteins. Co-incubation of the HUT78 CTCL cells with vorinostat (0.37 μM) and the JAK inhibitor 2-(2-chlorophenyl)-9-fluoro-3,6-dihydro-7H-benzo[h]imidazo[4,5-f]isoquinolin-7-one (Compound A) or JAK inhibitor I: 2-tert-butyl-9-fluoro-1,6-dihydro-7H-benzo[h]imidazo[4,5-f]isoquinolin-7-one (Compound B) resulted in a synergistic anti-proliferative effect as assessed by standard proliferation/viability assay (FIG. 3A). Furthermore, synergistic induction of apoptosis was also observed by TUNEL assay as detailed in Table 4. Referring to FIG. 3B, a decrease in tyrosine phosphorylation of STAT3 was observed by immunoblot analysis, showing that treatment with the JAK inhibitors effectively block activation of STAT proteins. Similar results were obtained in the CTCL line MJ, where dephosphorylation of STAT5, the most predominantly STAT member expressed in these cells, was noticeable (data not shown). The results gathered from studies in human lymphoma cell lines clearly corroborate the hypothesis that evaluation of the expression and phosphorylation of STAT1, 3 and 5 proteins can provide the skilled clinician with the tools necessary to predict vorinostat response from samples isolated from CTCL patients.

Figure 4A:
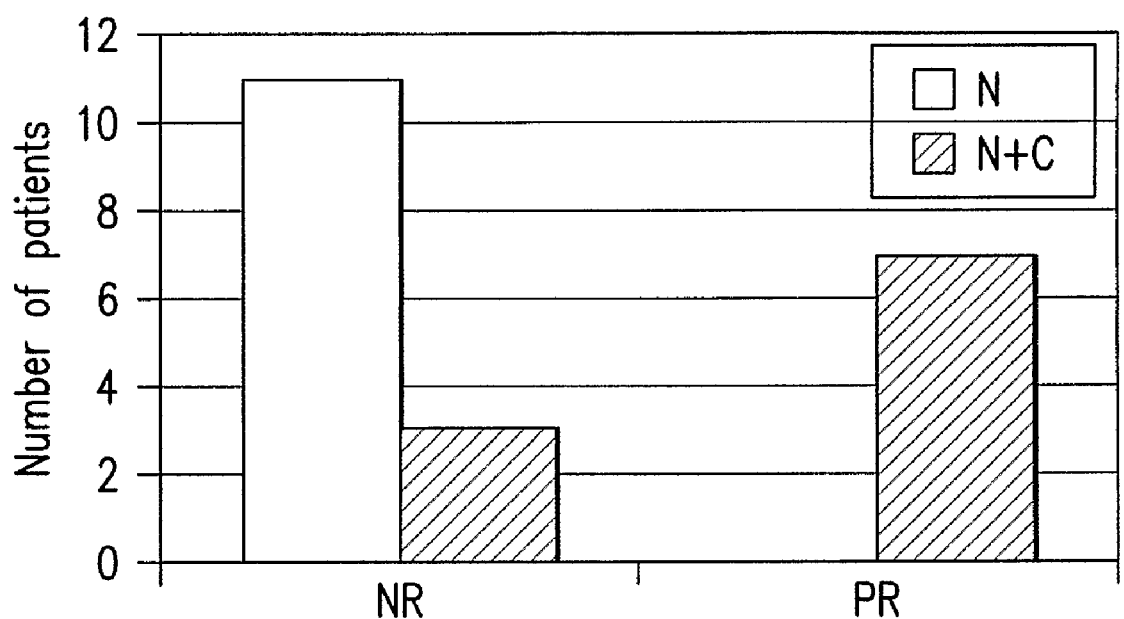
FIG. 4A. Immunohistochemical analysis if STAT1 in clinical samples. A Correlation between subcellular localization of STAT1 and vorinostat response across 21 positive baseline samples.
Figure 4B:
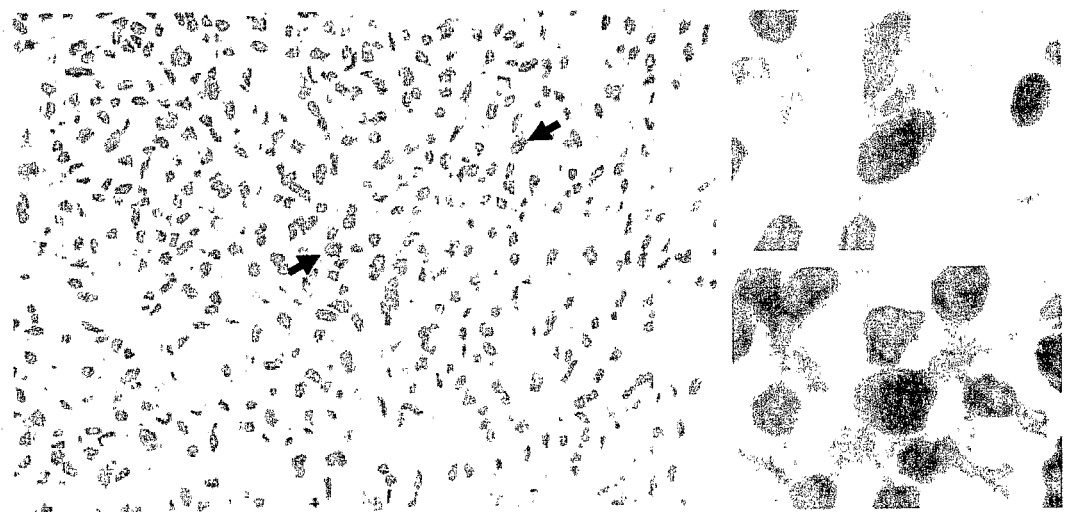
FIG. 4B Immunohistochemical analysis of STAT1 in skin biopsies from patient samples obtained in Phase II b CTCL trial. Representative examples of STAT1 nuclear localization in non-responder (NR) patients, and cytoplasmic staining in partial-responder (PR) patients are shown. N: nuclear; N+C: nuclear-cytoplasmic
Figure 4B:
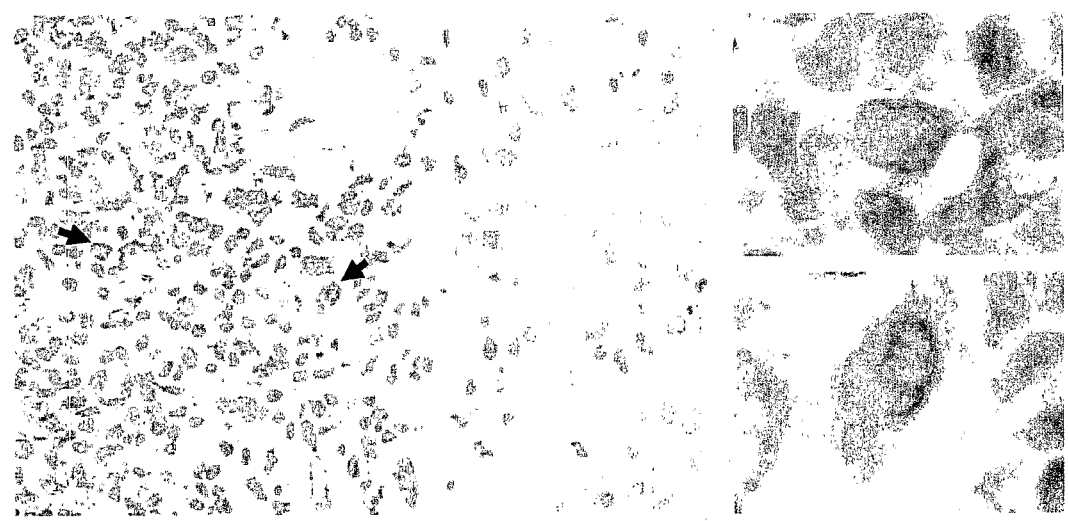

More, immunohistochemical examination of STAT1, 3, and 5 was performed across skin biopsies isolated from CTCL patients (N=48) in the vorinostat Phase II b clinical trial. The analysis showed that STAT1 expression was detectable in malignant T cells in approximately half of the samples (21 positively stained; 22 negatively stained; 5 poor quality specimens, or no malignant cells observed), and in those cases a relationship between nuclear accumulation of STAT1 response to treatment existed. The data clearly suggested that patients with STAT1 nuclear localization had a significant higher chance of not responding to vorinostat treatment ($p<0.01$; Fisher's exact test; FIG. 4A). Representative examples of STAT1 staining in partial responders and non-responders are shown (FIG. 4B). STAT3 expression levels appeared not to correlate with vorinostat sensitivity. In the case of STAT5, staining was detectable in malignant T cells from 41 samples. A trend was observed between high levels of expression and lack of clinical response ($p=0.08>0.05$; Fisher's exact test).

The data from studies in human lymphoma cell lines suggest that expression and phosphorylation of STAT-1,3 and 5 proteins can be used to predict vorinostat response from samples isolated from lymphoma patients.

On the basis of the assays used to monitor STAT proteins in cells with diverse response to vorinostat described herein, it appears that differential expression of the panel of protein biomarkers under investigation is predictive of the treatment outcome for patients presenting with cancer, thereby allowing for risk assessment and earlier clinical intervention especially in those patients at risk of failing treatment with SAHA or susceptible of becoming SAHA-resistant, e.g. those expressing increased levels of expression of STAS 1, 3 and 5 or increased levels of hyper-phosphorylated Stat proteins relative to normal or control samples.

TABLE 1

Response of lymphomas cell lines to vorinostat

| Subtype | Cell line | IC$_{50}$ (μM) (Cell Titre-Blue assay) | Caspase 3,7 activation- 24 h (1 μM vorinostat)* | TUNEL-48 h (3 μM vorinostat) |
|---|---|---|---|---|
| Lymphoma - T cell | SUPT1 | 0.32 | + | + |
| Lymphoma - Pre B | JM1 | 0.49 | + | + |
| Lymphoma - Burkitts | CA46 | 0.54 | − | + |
| Lymphoma DLBCL | Toledo (1) | 0.66 | + | + |
| Lymphoma- cancer | HUT102 | 0.83 | − | + |
| Lymphoma- cancer | HH | 0.89 | + | + |
| Lymphoma - ALCL | KARPAS-299 | 1.73 | − | − |
| Lymphoma - Burkitts | Jiyoye | 3.70 | − | − |
| Lymphoma - DLBCL | RCK8 | 4.55 | − | − |
| Lymphoma - Burkitts | EB1 | 6.40 | − | − |
| Lymphoma - ALCL | SR786 | 14.40 | − | − |
| Lymphoma - ALCL | SUPM2 | 14.52 | − | − |

N.D.: Not determined
*Caspase 3,7 activation > 2 fold over untreated control.

TABLE 2

Quantification of STAT expression and phosphorylation in lymphoma cell lines

| | STAT1 | p Ser-STAT1 | pTyr-STAT1 | STAT3 | p Ser-STAT3 | pTyr-STAT3 | STAT5 | pTyr-STAT5 |
|---|---|---|---|---|---|---|---|---|
| HH | 17.0 | 0.1 | 0.3 | 0.6 | 1.3 | 0.7 | 0.7 | 1.0 |
| SUPT1 | 1.0 | 1.0 | 1.0 | 1.0 | 1.0 | 1.0 | 1.0 | 1.0 |

TABLE 2-continued

Quantification of STAT expression and phosphorylation in lymphoma cell lines

|  | STAT1 | p Ser-STAT1 | pTyr-STAT1 | STAT3 | p Ser-STAT3 | pTyr-STAT3 | STAT5 | pTyr-STAT5 |
|---|---|---|---|---|---|---|---|---|
| Toledo | 5.6 | 1.2 | 1.7 | 0.6 | 1.0 | 1.4 | 1.0 | 1.0 |
| JM1 | 8.9 | 1.0 | 2.5 | 0.5 | 2.4 | 1.7 | 1.0 | 1.0 |
| CA46 | 5.3 | 1.5 | 3.1 | 0.7 | 0.0 | 0.8 | 0.5 | 1.0 |
| HUT102 | 104.3 | 1.8 | 1.1 | 0.4 | 0.0 | 0.6 | 0.5 | 1.0 |
| KARPAS | 532.6 | 3.7 | 13.7 | 0.9 | 5.5 | 7.7 | 8.1 | 8.5 |
| Jiyoye | 307.2 | 2.2 | 2.0 | 0.7 | 3.4 | 1.5 | 1.2 | 1.0 |
| RCK8 | 61.0 | 3.3 | 0.0 | 0.9 | 3.5 | 0.5 | 3.2 | 1.0 |
| EB1 | 186.0 | 2.2 | 1.4 | 0.7 | 3.1 | 1.1 | 1.6 | 1.0 |
| SUDHL1 | 48.6 | 1.6 | 1.3 | 1.5 | 27.5 | 14.3 | 2.5 | 15.7 |
| SUPM2 | 487.4 | 2.0 | 7.9 | 0.9 | 9.0 | 9.9 | 5.1 | 11.2 |
| SR786 | 648.0 | 4.0 | 11.7 | 1.1 | 16.9 | 14.2 | 15.6 | 18.3 |

* Values represent fold difference relative to STAT expression/phosphorylation in SUPT1 cells.

TABLE 3

Comparison of fold range of STAT expression and phosphorylation between vorinostat sensitive and less sensitive lymphoma cell lines

| Protein | Cell lines sensitive to vorinostat * | Cell lines less sensitive to vorinostat * |
|---|---|---|
| STAT1 | 1-17 | 41-648 |
| pSer-STAT1 | 0.1-1 | 2-4 |
| pTyr-STAT1 | 0.3-3 | 7-14 |
| STAT3 | 0.4-1 | 0.7-1.5 |
| pSer-STAT3 | 1-2.4 | 3.5-28 |
| pTyr-STAT3 | 0.7-1.7 | 8-14 |
| STAT5 | 0.5-1 | 2-16 |

* Values represent fold difference relative to STAT expression/phosphorylation in SUPT1 cells.

TABLE 4

Effect of vorinostat, JAK inhibitor I (L683) and the combination on induction of apoptosis

|  | % TUNEL positive cells |
|---|---|
| HUT78-vehicle | 3 |
| HUT78-VT | 11 |

TABLE 4-continued

Effect of vorinostat, JAK inhibitor I (L683) and the combination on induction of apoptosis

|  | % TUNEL positive cells |
|---|---|
| HUT78-L683 | 37 |
| HUT78- VT/L683 | 71 |
| HUT78- ST | 40 |

VT: vorinostat; L683: JAK inhibitor I, ST: staurosporine

EXAMPLE 2

Materials and Methods

An expanded set of 50 human cell lines, including the twelve cell lines listed in Table 1, were assembled (Table 2), that represent a range of lymphoid tumor types (including 10 diffuse large B cell lymphoma, 10 Burkitt lymphoma, 8 multiple myeloma and 5 CTCL). As detailed in Example 1, each of these cell lines was cultured in vitro and response to vorinostat was assessed at 8 different concentrations (0 and 0.04 to 30 micromolar) at 24 hr using the ApoONE™ Homogeneous Caspase-3/7 Assay (Promega) and at 24, 48 and 72 h using the CellTiter-Blue™ Cell Viability Assay (Promega). The CellTiter Blue assay was used to determine the vorinostat IC50 for each cell line. A representative subset of the data obtained are presented in Table 2.

TABLE 2

Response of various cancer cell lines to vorinostat

| Subtype | Catalog Reference Number | Cell line | IC$_{50}$(μM) (Cell Titre-Blue assay) | Caspase 3,7 activation- 24 h (1 μM vorinostat)* |
|---|---|---|---|---|
| Lymphoma -T cell | CRL-1942 | SUP_T1 | 0.32 | + |
| Lymphoma - Pre B lymphoblast | CRL-10423 | JM1 | 0.49 | + |
| Lymphoma - Burkitts | CRL-1648 | CA46 | 0.54 | − |
| Lymphoma- B Cell | CRL-2277 | BC_3 | 0.63 | + |
| Lymphoma DLBCL | CRL-2631 | Toledo (1) | 0.66 | + |
| Lymphoma Follicular | ACC 47 | DOHH_2 | 0.71 | − |
| Lymphoma DLBCL | CRL-2631 | Toledo (avg) | 0.72 | + |
| Multiple Myeloma | ACC 50 | OPM_2 | 0.76 | − |
| Lymphoma - Burkitts | CRL-1647 | ST486 | 0.78 | + |
| Lymphoma - Mantle cell | ACC 553 | JEKO_1 | 0.812 | − |
| Lymphoma - CTCL | TIB-162 | HUT_102 | 0.83 | − |
| Lymphoma - Burkitts | CRL-1432 | NAMALWA | 0.84 | − |
| Lymphoma- CTCL | CRL-2105 | HH | 0.8903 | + |
| Lymphoma - undifferentiated | CRL-1649 | MC116 | 0.9 | − |
| Lymphoma - Follicular | ACC 558 | SC_1 | 0.93 | − |

TABLE 2-continued

Response of various cancer cell lines to vorinostat

| Subtype | Catalog Reference Number | Cell line | $IC_{50}(\mu M)$ (Cell Titre-Blue assay) | Caspase 3,7 activation- 24 h (1 $\mu$M vorinostat)* |
|---|---|---|---|---|
| Multiple Myeloma | ACC 41 | LP-1 | 0.97 | – |
| Multiple Myeloma | ACC 569 | MOLP__8 | 1.13 | – |
| Lymphoma - Burkitts | CRL-1596 | Ramos__RA__1 | 1.24 | – |
| Lymphoma - B cell PEL | CRL-2230 | BC__1 | 1.27 | – |
| Lymphoma - CTCL | HTB-176 | H9 | 1.28 | – |
| Multiple Myeloma | CCL-155 | RPMI8226 | 1.29 | – |
| Lymphoma - Burkitts | CCL-86 | Raji | 1.36 | – |
| Multiple Myeloma | CRL-9068 | NCI__H929 | 1.4 | – |
| Lymphoma - histiocytic | CRL-1593.2 | U__937 | 1.44 | – |
| Multiple Myeloma | CCL159 | IM__9 | 1.57 | – |
| Lymphoma DLBCL | ACC 528 | OCI__LY__19 | 1.58 | – |
| Lymphoma - ALCL | ACC-31 | KARPAS__299 | 1.73 | – |
| Lymphoma DLBCL | CRL-2289 | DB | 1.87 | – |
| Lymphoma DLBCL | ACC 495 | SU__DHL__4 | 1.88 | – |
| Lymphoma DLBCL | CRL-2260 | HT (1) | 2.05 | – |
| Lymphoma- CTCL | TIB-161 | HuT__78 | 2.13 | – |
| Lymphoma - DLBCL | CCL-2261 | RL | 2.23 | – |
| Lymphoma - Burkitts | CCL-214 | NC__37 | 2.36 | – |
| Multiple Myeloma | TIB-196 | U266 | 2.47 | – |
| Lymphoma DLBCL | CRL2632 | Pfeiffer (1) | 2.57 | – |
| Lymphoma- non Hodgkins B cell | CRL-2630 | Farage | 2.59 | – |
| Lymphoma- CTCL | CRL-8294 | MJ | 2.78 | – |
| Multiple Myeloma | ACC 560 | EJM | 3.24 | – |
| Lymphoma - Burkitts | CCL-85 | EB__3 | 3.36 | – |
| Lymphoma - Mantle cell | ACC 342 | GRANTA__519 | 3.4 | – |
| Lymphoma - Hodgkins | HTB-146 | Hs__445 | 3.69 | – |
| Lymphoma - Burkitts | CCL-87 | Jiyoye | 3.7 | – |
| Lymphoma - Burkitts | CCL-213 | Daudi | 4.1 | – |
| Lymphoma - DLBCL | ACC 561 | RC__K8 | 4.55 | – |
| Lymphoma - Burkitts | HTB-60 | EB__1 | 6.4 | – |
| Lymphoma - ALCL | ACC 356 | SU__DHL__1 | 9.07 | – |
| Lymphoma - Burkitts | HTB-61 | EB__2 | 9.96 | – |
| Lymphoma - ALCL | ACC 369 | SR__786 | 14.4 | – |
| Lymphoma - ALCL | ACC 509 | SUP__M2 | 14.52 | – |
| Lymphoma - Hodgkins | CCL-113 | RPMI6666 | >30 | – |

Microarray gene expression profiling: Total RNA was isolated from each of the cell lines and expression of ~25,000 human genes was determined by hybridization to 60-mer oligonucleotide arrays (Agilent Technologies, Palo Alto, Calif.). Microarray gene expression experiments were performed using methods as described by Hughes et al., (Nature Biotechnology, 2001 19:342-7). Stratagene Universal Human Reference was used as the reference RNA in all hybridizations experiments. The expression level of each of the ~25,000 human genes was determined as compared to the level of expression of each corresponding gene in a Universal Human Reference RNA sample purchased from Stratagene (La Jolla, Calif.).

Results and Discussion

Gene expression data for all cell lines were analyzed using Rosetta Resolver (t gene expression data analysis software (Rosetta Biosoftware, Seattle, Wash.) to identify all genes that were differentially regulated with a p-value of <0.01 between cell lines whose cell viability was sensitive to treatment with vorinostat, IC50 less than 1 $\mu$M and caspase activation more than 2-fold, and cell lines whose viability was not sensitive to treatment with vorinostat, IC50 above 3 $\mu$M and caspase activation less than 2-fold. Using these criteria 313 genes were identified as significantly differentially regulated between cell lines Analysis of the gene sets that are enriched for the 313 genes, whose expression is associated with vorinostat response, identified JAK-STAT pathway as the most significantly enriched for differentially expressed genes. As shown in Table 3, genes in the JAK-STAT cascade were the most significantly enriched (P-value 5. 10E-06, Exact Fisher test) in the 313 vorinostat response associated genes (Foreground genes, column 4 in Table 3), as compared to the number of genes represented on the array within each biological pathway group (Background genes, column 3 in Table 3).

TABLE 3

Biological pathway enrichment of genes whose expression is associated with vorinostat exposure.

| Biological Pathway | P-value | Number Background Genes/23924 | Number Foreground Genes/313 |
|---|---|---|---|
| JAK-STAT cascade | 5.10E–06 | 151 (0.6%) | 11 (3.5%) |
| Tyrosine phosphorylation of STAT protein | 5.65E–06 | 53 (0.2%) | 7 (2.2%) |

TABLE 3-continued

Biological pathway enrichment of genes whose expression is associated with vorinostat exposure.

| Biological Pathway | P-value | Number Background Genes/23924 | Number Foreground Genes/313 |
|---|---|---|---|
| Cytokine and chemokine mediated signaling pathway | 8.14E–05 | 169 (0.7%) | 10 (3.2%) |
| Peptidyl-tyrosine phosphorylation | 0.0002886 | 128 (0.5%) | 8 (2.6%) |
| Peptidyl-tyrosine modification | 0.0003932 | 134 (0.6%) | 8 (2.6%) |
| Water homeostasis | 0.0010946 | 16 (0.1%) | 3 (1.0%) |
| Regulation of cyclin dependent protein kinase activity | 0.0026976 | 73 (0.3%) | 5 (1.6%) |
| Carbohydrate biosynthesis | 0.0034144 | 148 (0.6%) | 7 (2.2%) |
| Plasma membrane organization and biogenesis | 0.0046143 | 26 (0.1%) | 3 (1.0%) |
| Negative regulation of biosynthesis | 0.0047501 | 52 (0.2%) | 4 (1.3%) |
| Chaperone cofactor dependent protein folding | 0.0090534 | 33 (0.1%) | 3 (1.0%) |
| posttranslational protein folding | 0.0093472 | 63 (0.3%) | 4 (1.3%) |

Table 4 shows the gene expression values across the 50 cancer cell lines, listed in Table 2, for eleven genes in the JAK-STAT pathway. The cell line expression data are arranged based upon hierarchically cluster analysis. Agglomerative clustering was performed using 'correlation' distance metrics and 'avaerage' linkage. The cell lines are sorted by their vorinostat IC50 values, from the highest IC50 at the top to the lowest at the bottom.

TABLE 4

Gene expression values for JAK-STAT Pathway Genes.

| Cell Line | MYC | PIAS3 | JAK1 | STAT1 | STAT3 | SOCS1 | SOCS3 | STAT5B | STAT5A | JAK3 | STAT2 |
|---|---|---|---|---|---|---|---|---|---|---|---|
| SUP-T1 | 0.36308255 | −0.17389 | 0.020168463 | −0.45923 | 0.090762 | −0.16 | −0.07313 | 0.14136 | 0.132279 | −0.00868 | −0.03174 |
| JM1 | 0.0869305 | −0.22487 | −0.036006024 | −0.37414 | −0.17801 | 0.03 | −0.01614 | 0.048068 | −0.12212 | 0.067294 | 0.057679 |
| CA46 | 0.37247845 | 0.143727 | −0.077814853 | −0.55112 | −0.20811 | −0.04 | −0.04846 | −0.12499 | −0.18544 | 0.018194 | −0.00586 |
| BC-3 | −0.1966742 | 0.030358 | −0.079100271 | 0.379452 | −0.23629 | −0.43 | −0.06737 | −0.27335 | −0.50809 | −0.05443 | −0.00428 |
| Toledo (1) | −0.035172 | 0.082285 | 0.057316462 | −0.5726 | −0.09644 | 0.19 | −0.02899 | 0.082494 | −0.14111 | 0.021385 | −0.01171 |
| DOHH-2 | 0.00528318 | −0.16612 | −0.17021154 | −0.99849 | −0.16248 | −0.15 | −0.03641 | 0.165177 | 0.044058 | 0.016473 | −0.0039 |
| Toledo (ave) | 0.08591413 | −0.11613 | 0.092249075 | 0.416007 | 0.050084 | 0.17 | −0.0443 | −0.11619 | 0.505011 | −0.00295 | −0.0154 |
| OPM-2 | 0.39401465 | 0.240842 | −0.167558113 | −0.24159 | 0.000289 | −0.37 | −0.05459 | −0.2512 | −0.432 | −0.01442 | −0.01131 |
| ST486 | 0.16478961 | 0.33232 | 0.063400576 | −0.27547 | −0.19272 | −0.11 | −0.03229 | 0.024259 | −0.07574 | −0.01826 | −0.00802 |
| JEKO 1 | 0.17850413 | −0.06716 | −0.253946053 | −0.34505 | −0.33518 | −0.2 | −0.05605 | −0.4087 | −0.51918 | −0.00661 | 0.025056 |
| HUT-102 | −0.228879 | −0.15302 | 0.265704701 | 0.451309 | 0.271227 | 0.5 | 0.060981 | 0.227632 | 0.772719 | 0.054751 | 0.098523 |
| NAMALWA | 0.38411406 | 0.077282 | −0.081201782 | −0.19042 | −0.124 | 0.02 | −0.0006 | −0.05465 | −0.23894 | −0.03435 | −0.02736 |
| HH | 0.20482009 | 0.107724 | 0.09448571 | 0.022988 | −0.44128 | 0.08 | 0.027506 | 0.163087 | 0.132916 | 0.005039 | 0.016457 |
| MC116 | 0.49137857 | −0.00049 | 0.185913304 | −0.31566 | −0.04925 | 0.1 | 0.019371 | −0.04811 | −0.2809 | −0.04308 | −0.00135 |
| SC-1 | 0.15225348 | −0.12255 | −0.283098167 | −0.65442 | −0.28732 | −0.33 | −0.00988 | −0.23087 | −0.44309 | 0.029462 | 0.014981 |
| LP-1 | 0.61423778 | 0.228623 | −0.211237591 | −0.38835 | −0.05442 | −0.33 | −0.09412 | −0.24281 | −0.48924 | −0.00928 | −0.01007 |
| MOLP-8 | 0.39557776 | 0.194932 | −0.0909183 | −0.1693 | −0.07169 | −0.32 | −0.08909 | −0.31079 | −0.51142 | −0.03266 | −0.01307 |
| Ramos | 0.07295238 | 0.067358 | −0.101866795 | −0.93032 | −0.07749 | 0.23 | 0.104815 | −0.02199 | −0.21164 | 0.084284 | 0.084978 |
| BC-1 | 0.01676247 | 0.150599 | 0.034500519 | 0.190657 | −0.13304 | −0.34 | −0.052 | −0.35719 | −0.49309 | −0.02971 | −0.01103 |
| H9 | −1.6527088 | −0.32892 | 0.151520798 | 0.078066 | 0.293677 | −0.39 | 0.034856 | 0.217641 | 0.328515 | −0.00847 | −0.02507 |
| RPMI | 0.51385735 | −0.12893 | −0.166273953 | −0.19868 | −0.19453 | −0.34 | −0.04771 | −0.5156 | −0.31847 | −0.03929 | −0.02243 |
| Raji | 0.32682209 | 0.163807 | 0.036727408 | −0.76152 | −0.15367 | 0.05 | 0.018276 | −0.03628 | −0.44095 | −0.03012 | 0.004325 |
| NCI-H929 | −1.8220409 | 0.356309 | −0.179968295 | −0.08101 | −0.06221 | −0.24 | 0.016522 | −0.20969 | −0.49506 | 0.039583 | 0.027871 |
| U-937 | 0.43995737 | 0.036491 | 0.026594216 | 0.048662 | −0.13987 | −0.37 | −0.10912 | −0.13857 | 0.320456 | −0.04824 | −0.04195 |
| IM-9 | 0.24933957 | −0.13572 | −0.01790077 | 0.352289 | −0.09729 | −0.04 | −0.05129 | −0.08668 | 0.352404 | −0.03864 | −0.05947 |
| OCI-LY-19 | 0.52756463 | −0.25468 | 0.079417536 | −0.13244 | −0.13116 | −0.31 | −0.05102 | 0.021269 | 0.329011 | −0.00631 | 0.00098 |
| KARPAS-299 | −0.1809038 | 0.0757 | 0.345002154 | 0.901992 | 0.3677 | 0.62 | 0.072669 | 0.271041 | 0.153872 | −0.0152 | −0.01057 |
| DB | 0.46996813 | −0.06842 | −0.434752887 | −0.48767 | −0.24721 | −0.21 | 0.053253 | 0.575763 | 0.546597 | 0.015826 | −0.00012 |
| SUDHL4 | 0.40439237 | −0.12468 | −0.278616858 | −0.57213 | −0.21013 | −0.05 | −0.00802 | 0.294667 | −0.00852 | −0.01988 | −0.08591 |
| HT | −0.1659906 | 0.079831 | −0.245738653 | −0.35673 | 0.096112 | 0.41 | 0.099101 | 0.592941 | 0.52974 | 0.06654 | 0.066602 |
| HuT-78 | −1.8220409 | −0.44289 | 0.163464377 | 0.380966 | 0.208921 | −0.41 | −0.09433 | 0.166781 | 0.292559 | 0.011306 | −0.04599 |
| RL | 0.23005374 | −0.11093 | −0.116432896 | −0.40609 | −0.18768 | −0.17 | 0.018011 | 0.086301 | 0.118531 | −0.01888 | 0.008946 |
| NC-37 | 0.21548801 | −0.02213 | 0.12202693 | 0.098419 | −0.09275 | 0.06 | −0.10442 | −0.02279 | 0.329797 | −0.04408 | −0.05589 |
| U266 | −1.4380137 | 0.072474 | −0.172938635 | 0.455205 | 0.176338 | −0.37 | −0.0437 | −0.4531 | −0.40244 | −0.01157 | 0.030912 |

TABLE 4-continued

Gene expression values for JAK-STAT Pathway Genes.

| Cell Line | MYC | PIAS3 | JAK1 | STAT1 | STAT3 | SOCS1 | SOCS3 | STAT5B | STAT5A | JAK3 | STAT2 |
|---|---|---|---|---|---|---|---|---|---|---|---|
| Pfeiffer | 0.12218399 | −0.11767 | 0.376929144 | −0.1419 | 0.413881 | −0.02 | 0.02563 | −0.31677 | −0.2613 | −0.01506 | −0.01389 |
| Farge | −0.1412651 | 0.011882 | 0.295520643 | −0.12835 | 0.048113 | 0.02 | −0.06024 | 0.024339 | 0.172659 | 0.023424 | 0.052824 |
| MJ | 0.08219 | 0.050354 | 0.148405472 | 0.353624 | 0.365842 | 0.51 | 0.043458 | 0.873894 | 1.124623 | 0.007073 | −0.04478 |
| EJM | 0.10947633 | −0.00762 | 0.011139089 | 1.022487 | 0.190628 | −0.26 | 0.007042 | −0.42707 | −0.49548 | −0.00754 | 0.074724 |
| EB-3 | 0.19501971 | −0.05019 | −0.053358456 | −0.39751 | −0.18126 | −0.02 | 0.025112 | −0.09061 | −0.30809 | 0.038585 | −0.01215 |
| GRANTA-519 | −0.5267562 | −0.22397 | −0.597706308 | 0.049864 | −0.15903 | 0.13 | −0.05076 | −0.17255 | 0.173718 | −0.03213 | −0.00882 |
| Hs-445 | −0.1254411 | −0.21173 | −0.261583788 | 0.768879 | 0.136053 | 0.24 | −0.04886 | −0.10979 | 0.510454 | 0.027229 | −0.0038 |
| Jiyoye | 0.05887212 | 0.088061 | 0.175947139 | 0.659647 | 0.267599 | 0.14 | 0.010768 | −0.17445 | 0.09922 | −0.05468 | −0.0154 |
| Daudi | 0.38922938 | 0.039386 | 0.083670089 | 0.07131 | −0.24647 | 0.1 | 0.072714 | 0.058758 | −0.45629 | −0.0192 | 0.033954 |
| RC-K8 | 0.20682912 | −0.319 | −0.024984618 | 0.243913 | 0.080018 | 0.14 | 0.047704 | 0.298057 | 0.856107 | 0.040432 | 0.009386 |
| EB-1 | −0.2186405 | 0.192484 | 0.216975013 | 0.735532 | 0.212 | 0.38 | −0.02266 | 0.154453 | 0.485842 | 0.006996 | −0.01273 |
| SU-DHL-1 | 0.08722616 | 0.163129 | 0.039769927 | −0.05916 | 0.808912 | 0.43 | 0.260042 | 0.389628 | −0.5561 | 0.062091 | −0.00228 |
| EB-2 | −0.1080726 | 0.140035 | 0.359152356 | 0.780339 | 0.300205 | 0.27 | 0.014654 | 0.269246 | 0.39368 | 0.028742 | 0.031193 |
| SR-786 | −0.1368868 | 0.26241 | 0.310416797 | 1.145063 | 0.394914 | 0.68 | 0.171414 | 0.218883 | 0.377623 | −0.02338 | −0.01615 |
| SUP-M2 | −0.2037075 | −0.04316 | 0.407029251 | 1.040683 | 0.214184 | 0.5 | 0.207129 | −0.09943 | −0.4991 | −0.01171 | −0.01801 |
| RPMI 6666 | 0.39163007 | 0.226454 | −0.060231542 | −0.45802 | −0.23646 | −0.01 | −0.01549 | −0.07155 | −0.1886 | 0.034093 | 0.011133 |

The data in Table 4 show that measurement of the gene expression level of one or more of the listed JAK-STAT genes can be used to predict the sensitivity and/or resistance of a cell sample to vorinostat treatment. In particular, increased expression of one or more of the JAK1, STAT1, STAT3, STAT5b, SOCS1, SOCS3 and STAT5a transcripts is associated with increased resistance of a cell sample to treatment with vorinosat, while conversely, when expression of one or more of these genes is decreased relative to the Stratagene control sample, than a cell sample is more likely to exhibit sensitivity to vorinostat treatment.

Table 5 lists the public database accession numbers, transcript SEQ ID NOs, protein SEQ ID NOs and microarray probe SEQ ID NOs for each of the JAK-STAT pathway genes listed in Table 4.

TABLE 5

Gene IDs for the JAK-STAT genes.

| Gene | Reference Number | Transcript SEQ ID NO: | Protein SEQ ID NO: | Probe SEQ ID NO: |
|---|---|---|---|---|
| MYC | NM_002467 | SEQ ID NO: 1 | SEQ ID NO: 2 | SEQ ID NO: 3 |
| PIAS3 | NM_006099 | SEQ ID NO: 4 | SEQ ID NO: 5 | SEQ ID NO: 6 |
| JAK1 | NM_002227 | SEQ ID NO: 7 | SEQ ID NO: 8 | SEQ ID NO: 9 |
| STAT1 | NM_007315 | SEQ ID NO: 10 | SEQ ID NO: 11 | SEQ ID NO: 12 |
| STAT3 | NM_003150 | SEQ ID NO: 13 | SEQ ID NO: 14 | SEQ ID NO: 15 |
| STAT5B | AL080218 | SEQ ID NO: 16 | | SEQ ID NO: 17 |
| SOCS1 | NM_003745 | SEQ ID NO: 18 | SEQ ID NO: 19 | SEQ ID NO: 20 |
| SOCS3 | NM_003955 | SEQ ID NO: 21 | SEQ ID NO: 22 | SEQ ID NO: 23 |
| STAT5A | NM_003152 | SEQ ID NO: 24 | SEQ ID NO: 25 | SEQ ID NO: 26 |
| JAK3 | NM_000215 | SEQ ID NO: 27 | SEQ ID NO: 28 | SEQ ID NO: 29 |
| STAT2 | NM_005419 | SEQ ID NO: 30 | SEQ ID NO: 31 | SEQ ID NO: 32 |

REFERENCES

Alas, S., and Bonavida, B. (2003). Inhibition of constitutive STAT-3 activity sensitizes resistant non-Hodgkin's lymphoma and multiple myeloma to chemotherapeutic drug-mediated apoptosis. Clin Cancer Res9, 316-326.

Frank, D. A. (2002). STAT signaling in cancer: insights into pathogenesis and treatment strategies. In Signal transduction in cancer (Secaucus, Kluwer Academic Publishers), pp. 267-291.

Ikuta, K., Takemura, K., Kihara, M., Nishimura, M., Ueda, N., Naito, S., Lee, E., Shimizu, E., and Yamauchi, A. (2005). Overexpression of constitutive signal transducer and activator of transcription 3 mRNA in cisplatin-resistant human non-small cell lung cancer cells. Oncol Rep 13, 217-222.

Khoury, J. D., Medeiros, L. J., Rassidakis, G. Z., Yared, M. A., Tsioli, P., Leventaki, V., Schmitt-Graeff, A., Herling, M., Amin, H. M., and Lai, R. (2003). Differential expression and clinical significance of tyrosine-phosphorylated STAT-3 in ALK+ and ALK− anaplastic large cell lymphoma. Clin Cancer Res 9, 3692-3699.

Mitchell, T. J., and John, S. (2005). Signal transducer and activator of transcription (STAT) signalling and T-cell lymphomas. Immunology 114, 301-312.

Roberts, D., Schick, J., Conway, S., Biade, S., Laub, P. B., Stevenson, J. P., Hamilton, T. C., O'Dwyer, P. J., and Johnson, S. W. (2005). Identification of genes associated with platinum drug sensitivity and resistance in human ovarian cancer cells. Br J Cancer 92, 1149-1158.

Yu, H., and Jove, R. (2004). The STATs of cancer—new molecular targets come of age. Nat Rev Cancer 4, 97-105.

What is claimed:

1. A method of predicting whether a patient presenting with an HDAC mediated cutaneous T-cell lymphoma is at risk of non-responsiveness to treatment with SAHA, comprising: detecting in malignant T cells from the patient the phosphorylation status of STAT-1 protein relative to the phosphorylation status of SAT-1 protein in malignant T cell from a subject presenting with an HDAC mediated cutaneous T-cell lymphoma that is responsive to treatment with SAHA, wherein higher levels of phosphorylation of STAT-1 protein in the patient sample as compared to the level of phosphorylation of STAT-1 protein in the subject presenting with HDAC mediated cutaneous T-cell lymphoma that is responsive to treatment with SAHA indicates the patient is non-responsive to treatment with SAHA.

* * * * *

SEQUENCE LISTING

<160> NUMBER OF SEQ ID NOS: 32

<210> SEQ ID NO 1
<211> LENGTH: 2377
<212> TYPE: DNA
<213> ORGANISM: Homo sapiens

<400> SEQUENCE: 1

| | | | | | | |
|---|---|---|---|---|---|---|
| acccccgagc | tgtgctgctc | gcggccgcca | ccgccgggcc | ccggccgtcc | ctggctcccc | 60 |
| tcctgcctcg | agaagggcag | ggcttctcag | aggcttggcg | ggaaaaagaa | cggagggagg | 120 |
| gatcgcgctg | agtataaaag | ccggttttcg | gggctttatc | taactcgctg | tagtaattcc | 180 |
| agcgagaggc | agagggagcg | agcgggcggc | cggctagggt | ggaagagccg | ggcgagcaga | 240 |
| gctgcgctgc | gggcgtcctg | ggaagggaga | tccggagcga | ataggggget | tcgcctctgg | 300 |
| cccagccctc | ccgctgatcc | cccagccagc | ggtccgcaac | ccttgccgca | tccacgaaac | 360 |
| tttgcccata | gcagcgggcg | ggcactttgc | actggaactt | acaacacccg | agcaaggacg | 420 |
| cgactctccc | gacgcgggga | ggctattctg | cccatttggg | gacacttccc | cgccgctgcc | 480 |
| aggacccgct | tctctgaaag | gctctccttg | cagctgctta | gacgctggat | tttttttcggg | 540 |
| tagtggaaaa | ccagcagcct | cccgcgacga | tgcccctcaa | cgttagcttc | accaacagga | 600 |
| actatgacct | cgactacgac | tcggtgcagc | cgtatttcta | ctgcgacgag | gaggagaact | 660 |
| tctaccagca | gcagcagcag | agcgagctgc | agccccggc | gcccagcgag | gatatctgga | 720 |
| agaaattcga | gctgctgccc | accccgcccc | tgtcccctag | ccgccgctcc | gggctctgct | 780 |
| cgcccctccta | cgttgcggtc | acacccttct | cccttcgggg | agacaacgac | ggcggtggcg | 840 |
| ggagcttctc | cacggccgac | cagctggaga | tggtgaccga | gctgctggga | ggagacatgg | 900 |
| tgaaccagag | tttcatctgc | gacccggacg | acgagacctt | catcaaaaac | atcatcatcc | 960 |
| aggactgtat | gtggagcggc | ttctcggccg | ccgccaagct | cgtctcagag | aagctggcct | 1020 |
| cctaccaggc | tgcgcgcaaa | gacagcggca | gcccgaaccc | cgccgcggc | cacagcgtct | 1080 |
| gctccacctc | cagcttgtac | ctgcaggatc | tgagcgccgc | cgcctcagag | tgcatcgacc | 1140 |
| cctcggtggt | cttcccctac | cctctcaacg | acagcagctc | gcccaagtcc | tgcgcctcgc | 1200 |
| aagactccag | cgccttctct | ccgtcctcgg | attctctgct | ctcctcgacg | gagtcctccc | 1260 |
| cgcagggcag | ccccgagccc | ctggtgctcc | atgaggagac | accgcccacc | accagcagcg | 1320 |
| actctgagga | ggaacaagaa | gatgaggaag | aaatcgatgt | tgtttctgtg | gaaaagaggc | 1380 |
| aggctcctgg | caaaaggtca | gagtctggat | caccttctgc | tggaggccac | agcaaacctc | 1440 |
| ctcacagccc | actggtcctc | aagaggtgcc | acgtctccac | acatcagcac | aactacgcag | 1500 |
| cgcctcccctc | cactcggaag | gactatcctg | ctgccaagag | ggtcaagttg | gacagtgtca | 1560 |
| gagtcctgag | acagatcagc | aacaaccgaa | aatgcaccag | ccccaggtcc | tcggacaccg | 1620 |
| aggagaatgt | caagaggcga | acacacaacg | tcttggagcg | ccagaggagg | aacgagctaa | 1680 |
| aacgagcttt | ttttgccctg | cgtgaccaga | tcccggagtt | ggaaaacaat | gaaaaggccc | 1740 |
| ccaaggtagt | tatccttaaa | aaagccacag | catacatcct | gtccgtccaa | gcagaggagc | 1800 |
| aaaagctcat | ttctgaagag | gacttgttgc | ggaaacgacg | agaacagttg | aaacacaaac | 1860 |
| ttgaacagct | acggaactct | tgtgcgtaag | gaaaagtaag | gaaaacgatt | ccttctaaca | 1920 |
| gaaatgtcct | gagcaatcac | ctatgaactt | gtttcaaatg | catgatcaaa | tgcaacctca | 1980 |
| caaccttggc | tgagtcttga | gactgaaaga | tttagccata | atgtaaactg | cctcaaattg | 2040 |

-continued

```
gactttgggc ataaaagaac ttttttatgc ttaccatctt ttttttttct ttaacagatt    2100
tgtatttaag aattgttttt aaaaaatttt aagatttaca caatgtttct ctgtaaatat    2160
tgccattaaa tgtaaataac tttaataaaa cgtttatagc agttacacag aatttcaatc    2220
ctagtatata gtacctagta ttataggtac tataaacect aattttttt atttaagtac     2280 attttgcttt ttaaagttga ttttttttcta ttgtttttag aaaaaataaa ataactggca   2340
aatatatcat tgagccaaaa aaaaaaaaaa aaaaaa                              2377
```

<210> SEQ ID NO 2
<211> LENGTH: 454
<212> TYPE: PRT
<213> ORGANISM: Homo sapiens

<400> SEQUENCE: 2

```
Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
                20                  25                  30

Ser Val Gln Pro Tyr Phe Tyr Cys Asp Glu Glu Glu Asn Phe Tyr Gln
            35                  40                  45

Gln Gln Gln Gln Ser Glu Leu Gln Pro Pro Ala Pro Ser Glu Asp Ile
        50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
                100                 105                 110

Gln Leu Glu Met Val Thr Glu Leu Leu Gly Gly Asp Met Val Asn Gln
            115                 120                 125

Ser Phe Ile Cys Asp Pro Asp Asp Glu Thr Phe Ile Lys Asn Ile Ile
        130                 135                 140

Ile Gln Asp Cys Met Trp Ser Gly Phe Ser Ala Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
                180                 185                 190

Leu Gln Asp Leu Ser Ala Ala Ala Ser Glu Cys Ile Asp Pro Ser Val
            195                 200                 205

Val Phe Pro Tyr Pro Leu Asn Asp Ser Ser Ser Pro Lys Ser Cys Ala
        210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
                260                 265                 270

Asp Glu Glu Glu Ile Asp Val Val Ser Val Glu Lys Arg Gln Ala Pro
            275                 280                 285

Gly Lys Arg Ser Glu Ser Gly Ser Pro Ser Ala Gly Gly His Ser Lys
        290                 295                 300

Pro Pro His Ser Pro Leu Val Leu Lys Arg Cys His Val Ser Thr His
305                 310                 315                 320
```

| | | | | | | | | | | | |
|---|---|---|---|---|---|---|---|---|---|---|---|
|Gln|His|Asn|Tyr|Ala|Ala|Pro|Pro|Ser|Thr|Arg|Lys|Asp|Tyr|Pro|Ala|
| | | |325| | | |330| | | |335|

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
            355                 360                 365

Val Lys Arg Arg Thr His Asn Val Leu Glu Arg Gln Arg Arg Asn Glu
        370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
        435                 440                 445

Leu Arg Asn Ser Cys Ala
    450

<210> SEQ ID NO 3
<211> LENGTH: 60
<212> TYPE: DNA
<213> ORGANISM: Homo sapiens

<400> SEQUENCE: 3
gttacacaga atttcaatcc tagtatatag tacctagtat tataggtact ataaacccta    60

<210> SEQ ID NO 4
<211> LENGTH: 2991
<212> TYPE: DNA
<213> ORGANISM: Homo sapiens

<400> SEQUENCE: 4
ctgggcctga gctccggctc cggctggggc gcctgcgatg tctcaagatg gcggagctgg    60
gcgaattaaa gcacatggtg atgagtttcc gggtgtctga gctccaggtg cttcttggct    120 tgctggccg gaacaagagt ggacggaagc acgagctcct ggccaaggct ctgcacctcc    180
tgaagtccag ctgtgcccct agtgtccaga tgaagatcaa agagctttac cgacgacgct    240
ttccccggaa gaccctgggg ccctctgatc tctcccttct ctctttgccc cctggcacct    300
ctcctgtagg ctccctggt cctctagctc ccattccccc aacgctgttg gcccctggca    360
ccctgctggg ccccaagcgt gaggtggaca tgcaccccc tctgccccag cctgtgcacc    420
ctgatgtcac catgaaacca ttgcccttct atgaagtcta tggggagctc atccggccca    480
ccacccttgc atccacttct agccagcggt ttgaggaagc gcactttacc tttgccctca    540
caccccagca agtgcagcag attcttacat ccagagaggt tctgccagga gccaaatgtg    600
attataccat acaggtgcag ctaaggttct gtctctgtga gaccagctgc ccccaggaag    660
attattttcc ccccaacctc tttgtcaagg tcaatgggaa actgtgcccc ctgccgggtt    720
accttccccc aaccaagaat ggggccgagc caagagggcc cagccgcccc atcaacatca    780 caccctggc tcgactctca gccactgttc ccaacaccat tgtggtcaat tggtcatctg    840
agttcggacg gaattactcc ttgtctgtgt acctggtgag gcagttgact gcaggaaccc    900
ttctacaaaa actcagagca aagggtatcc ggaacccaga ccactcgcgg gcactgatca    960
aggagaaatt gactgctgac cctgacagtg aggtggccac tacaagtctc cgggtgtcac    1020
tcatgtgccc gctagggaag atgcgcctga ctgtcccttg tcgtgccctc acctgcgccc    1080

```
acctgcagag cttcgatgct gcccttatc tacagatgaa tgagaagaag cctacatgga    1140
catgtcctgt gtgtgacaag aaggctccct atgaatctct tatcattgat ggtttattta    1200
tggagattct tagttcctgt tcagattgtg atgagatcca attcatggaa gatggatcct    1260
ggtgcccaat gaaacccaag aaggaggcat ctgaggtttg ccccccgcca gggtatgggc    1320
tggatggcct ccagtacagc ccagtccagg ggggagatcc atcagagaat aagaagaagg    1380
tcgaagttat tgacttgaca atagaaagct catcagatga ggaggatctg cccctacca     1440 agaagcactg ttctgtcacc tcagctgcca tcccggccct acctggaagc aaaggagtcc    1500
tgacatctgg ccaccagcca tcctcggtgc taaggagccc tgctatgggc acgttgggtg    1560
gggatttcct gtccagtctc ccactacatg agtacccacc tgccttccca ctggagccg     1620 acatccaagg tttagattta ttttcatttc ttcagacaga gagtcagcac tatgcccct     1680 ctgtcatcac ctcactagat gaacaggatg cccttggcca cttcttccag taccgaggga    1740 cccccttctca ctttctgggc ccactggccc ccacgctggg gagctccac tgcagcgcca    1800 ctccggcgcc ccctcctggc cgtgtcagca gcattgtggc cctgggggg gccttgaggg    1860 aggggcatgg aggaccctg ccctcaggtc cctctttgac tggctgtcgg tcagacatca    1920
tttccctgga ctgagttccc tggattatgg aaacttcgct gtcccccaac actgagcaag    1980
tatgctgtgg agtcccaacc ccagctactc tgatccctct gggggctctg gccaggggcc    2040
agacagacct tcacagatgc ctacttttgg cctcatctct gcctgacaag gccagcaccc    2100
aaagggttaa tatttaacct ctttttaagg acactgggt ctgtttctgg aaatgttctt     2160
tagatggtgg cacattcctt tgggtatgtt aacctaggca gtgggaggca aatgggatgg    2220
tatgtgagct aggagaaggg ctgaaccctc agccttgact atgtctagag cctcttgggg    2280
aaggggcacc tctcttgaac cccaaatgct ctctcttctt attacccaaa cccatggctc    2340
tatttcttct tcacatccat tgtctcttca tgtctattcc attcccttcg gccaaacaga    2400
caggtggaaa aactgagaca ggcagtttca gagatggaca gagaactta ttttggattg     2460 tggatgtgga cttttttgta cataaataag aaaaaccaaa atactccaaa gatgacttcc    2520
cctgcctcct actccagtat gacagaggag gatgtaaggc cttagccatg atctgcaggg    2580
gtctgggagt caggcccggc ctattgcttg ggtctctctc tatttatata tctaagttca    2640
cagtgtttct tattcccccc taagcttcta gaggctcatg gccctgtagt taggcctggc    2700
tcattctgca cctttccagg gaggtggaag gaccctgtgc cctccttccc aatcttcttt    2760
ttcaggctcg ccaaggccta ggacctatgt tgtaatttta ctttttattt ctaaagttgt    2820
agtgaagctc tcacccataa taaggttgt gaatgttcaa aaaaaaaaa aaaaaaaaa       2880 aaaaaaaaa aaaaaaaaa aaaaaaaaa aaaaaaaaa aaaaaaaaa aaaaaaaaa          2940 aaaaaaaaa aaaaaaaaa aaaaaaaaa aaaaaaaaa aaaaaaaaa a                  2991
```

<210> SEQ ID NO 5
<211> LENGTH: 619
<212> TYPE: PRT
<213> ORGANISM: Homo sapiens

<400> SEQUENCE: 5

```
Met Val Met Ser Phe Arg Val Ser Glu Leu Gln Val Leu Leu Gly Phe
1               5                   10                  15

Ala Gly Arg Asn Lys Ser Gly Arg Lys His Glu Leu Leu Ala Lys Ala
            20                  25                  30

Leu His Leu Leu Lys Ser Ser Cys Ala Pro Ser Val Gln Met Lys Ile
```

```
              35                  40                  45
Lys Glu Leu Tyr Arg Arg Arg Phe Pro Arg Lys Thr Leu Gly Pro Ser
             50                  55                  60
Asp Leu Ser Leu Leu Ser Leu Pro Pro Gly Thr Ser Pro Val Gly Ser
 65                  70                  75                  80
Pro Gly Pro Leu Ala Pro Ile Pro Pro Thr Leu Leu Ala Pro Gly Thr
                 85                  90                  95
Leu Leu Gly Pro Lys Arg Glu Val Asp Met His Pro Pro Leu Pro Gln
                100                 105                 110
Pro Val His Pro Asp Val Thr Met Lys Pro Leu Pro Phe Tyr Glu Val
            115                 120                 125
Tyr Gly Glu Leu Ile Arg Pro Thr Thr Leu Ala Ser Thr Ser Ser Gln
            130                 135                 140
Arg Phe Glu Glu Ala His Phe Thr Phe Ala Leu Thr Pro Gln Gln Val
145                 150                 155                 160
Gln Gln Ile Leu Thr Ser Arg Glu Val Leu Pro Gly Ala Lys Cys Asp
                165                 170                 175
Tyr Thr Ile Gln Val Gln Leu Arg Phe Cys Leu Cys Glu Thr Ser Cys
                180                 185                 190
Pro Gln Glu Asp Tyr Phe Pro Pro Asn Leu Phe Val Lys Val Asn Gly
            195                 200                 205
Lys Leu Cys Pro Leu Pro Gly Tyr Leu Pro Pro Thr Lys Asn Gly Ala
            210                 215                 220
Glu Pro Lys Arg Pro Ser Arg Pro Ile Asn Ile Thr Pro Leu Ala Arg
225                 230                 235                 240
Leu Ser Ala Thr Val Pro Asn Thr Ile Val Asn Trp Ser Ser Glu
                245                 250                 255
Phe Gly Arg Asn Tyr Ser Leu Ser Val Tyr Leu Val Arg Gln Leu Thr
                260                 265                 270
Ala Gly Thr Leu Leu Gln Lys Leu Arg Ala Lys Gly Ile Arg Asn Pro
            275                 280                 285
Asp His Ser Arg Ala Leu Ile Lys Glu Lys Leu Thr Ala Asp Pro Asp
            290                 295                 300
Ser Glu Val Ala Thr Thr Ser Leu Arg Val Ser Leu Met Cys Pro Leu
305                 310                 315                 320
Gly Lys Met Arg Leu Thr Val Pro Cys Arg Ala Leu Thr Cys Ala His
                325                 330                 335
Leu Gln Ser Phe Asp Ala Ala Leu Tyr Leu Gln Met Asn Glu Lys Lys
                340                 345                 350
Pro Thr Trp Thr Cys Pro Val Cys Asp Lys Lys Ala Pro Tyr Glu Ser
            355                 360                 365
Leu Ile Ile Asp Gly Leu Phe Met Glu Ile Leu Ser Ser Cys Ser Asp
            370                 375                 380
Cys Asp Glu Ile Gln Phe Met Glu Asp Gly Ser Trp Cys Pro Met Lys
385                 390                 395                 400
Pro Lys Lys Glu Ala Ser Glu Val Cys Pro Pro Gly Tyr Gly Leu
                405                 410                 415
Asp Gly Leu Gln Tyr Ser Pro Val Gln Gly Gly Asp Pro Ser Glu Asn
            420                 425                 430
Lys Lys Lys Val Glu Val Ile Asp Leu Thr Ile Glu Ser Ser Ser Asp
            435                 440                 445
Glu Glu Asp Leu Pro Pro Thr Lys Lys His Cys Ser Val Thr Ser Ala
450                 455                 460
```

```
Ala Ile Pro Ala Leu Pro Gly Ser Lys Gly Val Leu Thr Ser Gly His
465                 470                 475                 480

Gln Pro Ser Ser Val Leu Arg Ser Pro Ala Met Gly Thr Leu Gly Gly
                485                 490                 495

Asp Phe Leu Ser Ser Leu Pro Leu His Glu Tyr Pro Pro Ala Phe Pro
            500                 505                 510

Leu Gly Ala Asp Ile Gln Gly Leu Asp Leu Phe Ser Phe Leu Gln Thr
        515                 520                 525

Glu Ser Gln His Tyr Gly Pro Ser Val Ile Thr Ser Leu Asp Glu Gln
    530                 535                 540

Asp Ala Leu Gly His Phe Phe Gln Tyr Arg Gly Thr Pro Ser His Phe
545                 550                 555                 560

Leu Gly Pro Leu Ala Pro Thr Leu Gly Ser Ser His Cys Ser Ala Thr
                565                 570                 575

Pro Ala Pro Pro Pro Gly Arg Val Ser Ser Ile Val Ala Pro Gly Gly
            580                 585                 590

Ala Leu Arg Glu Gly His Gly Gly Pro Leu Pro Ser Gly Pro Ser Leu
        595                 600                 605

Thr Gly Cys Arg Ser Asp Ile Ile Ser Leu Asp
    610                 615

<210> SEQ ID NO 6
<211> LENGTH: 60
<212> TYPE: DNA
<213> ORGANISM: Homo sapiens

<400> SEQUENCE: 6
cctaggacct atgttgtaat tttactttt atttctaaag ttgtagtgaa gctctcaccc      60

<210> SEQ ID NO 7
<211> LENGTH: 3541
<212> TYPE: DNA
<213> ORGANISM: Homo sapiens

<400> SEQUENCE: 7
tccagtttgc ttcttggaga acactggaca gctgaataaa tgcagtatct aaatataaaa      60
gaggactgca atgccatggc tttctgtgct aaaatgagga gctccaagaa gactgaggtg     120 aacctgagg ccccctgagcc aggggtggaa gtgatcttct atctgtcgga cagggagccc     180
ctccggctgg gcagtggaga gtacacagca gaggaactgt gcatcagggc tgcacaggca     240
tgccgtatct ctcctctttg tcacaacctc tttgccctgt atgacgagaa caccaagctc     300
tggtatgctc caaatcgcac catcaccgtt gatgacaaga tgtccctccg gctccactac     360
cggatgaggt ctatttcac caattggcat ggaaccaacg acaatgagca gtcagtgtgg     420
cgtcattctc caaagaagca gaaaaatggc tacgagaaaa aaagattcc agatgcaacc     480 cctctccttg atgccagctc actggagtat ctgtttgctc aggacagta tgatttggtg     540 aaatgcctgg ctcctattcg agaccccaag accgagcagg atggacatga tattgagaac     600
gagtgtctag gatggctgt cctggccatc tcacactatg ccatgatgaa gagatgcag     660 ttgccagaac tgcccaagga catcagctac aagcgatata ttccagaaac attgaataag     720
tccatcagac agaggaacct tctcaccagg atgcggataa ataatgtttt caaggatttc     780
ctaaaggaat taacaacaa gaccatttgt gacagcagcg tgtccacgca tgacctgaag     840
gtgaaatact ggctaccctt ggaaactttg acaaaacatt acggtgctga atatttgag     900 acttccatgt tactgatttc atcagaaaat gagatgaatt ggtttcattc gaatgacggt     960
```

```
ggaaacgttc tctactacga agtgatggtg actgggaatc ttggaatcca gtggaggcat    1020
aaaccaaatg ttgtttctgt tgaaaaggaa aaaataaaac tgaagcggaa aaaactggaa    1080
aataaagaca agaaggatga ggagaaaaac aagatccggg aagagtggaa caattttttca   1140 ttcttccctg aaatcactca cattgtaata aaggagtctg tggtcagcat taacaagcag    1200
gacaacaaga aaatggaact gaagctctct tcccacgagg aggccttgtc ctttgtgtcc    1260
ctggtagatg ctacttccg gctcacagca gatgccatc attacctctg caccgacgtg      1320 gccccccgt tgatcgtcca caacatacag aatggctgtc atggtccaat ctgtacagaa     1380
tacgccatca ataaattgcg gcaagaagga agcgaggagg ggatgtacgt gctgaggtgg    1440
agctgcaccg actttgacaa catcctcatg accgtcacct gctttgagaa gtctgagcag    1500
gtgcagggtg cccagaagca gttcaagaac tttcagatcg aggtgcagaa gggccgctac    1560
agtctgcacg gttcggaccg cagcttcccc agcttgggag acctcatgag ccacctcaag    1620
aagcagatcc tgcgcacgga taacatcagc ttcatgctaa aacgctgctg ccagcccaag    1680
ccccgagaaa tctccaacct gctggtggct actaagaaag cccaggagtg gcagcccgtc    1740
taccccatga gccagctgag tttcgatcgg atcctcaaga aggatctggt gcagggcgag    1800
caccttggga gaggcacgag aacacacatc tattctggga ccctgatgga ttacaaggat    1860
gacgaaggaa cttctgaaga gaagaagata aaagtgatcc tcaaagtctt agaccccagc    1920
cacagggata tttccctggc cttcttcgag gcagccagca tgatgagaca ggtctcccac    1980
aaacacatcg tgtacctcta tggcgtctgt gtccgcgacg tggagaatat catggtggaa    2040
gagtttgtgg aagggggtcc tctggatctc ttcatgcacc ggaaaagtga tgtccttacc    2100
acaccatgga aattcaaagt tgccaaacag ctggccagtg ccctgagcta cttggaggat    2160
aaagacctgg tccatggaaa tgtgtgtact aaaaaccctcc tcctggcccg tgagggaatc    2220
gacagtgagt gtggcccatt catcaagctc agtgaccccg gcatccccat tacggtgctg    2280
tctaggcaag aatgcattga acgaatccca tggattgctc ctgagtgtgt tgaggactcc    2340
aagaacctga gtgtggctgc tgacaagtgg agctttggaa ccacgctctg ggaaatctgc    2400
tacaatggcg agatccccct tgaaagacaag acgctgattg agaaagagag attctatgaa    2460
agccggtgca ggccagtgac accatcatgt aaggagctgg ctgacctcat gacccgctgc    2520
atgaactatg accccaatca gaggcctttc ttccgagcca tcatgagaga cattaataag    2580
cttgaagagc agaatccaga tattgttttcc agaaaaaaaa accagccaac tgaagtggac    2640
cccacacatt ttgagaagcg cttcctaaag aggatccgtg acttgggaga gggccacttt    2700
gggaaggttg agctctgcag gtatgacccc gaagacaata caggggagca ggtggctgtt    2760
aaatctctga gcctgagag tggaggtaac cacatagctg atctgaaaaa ggaaatcgag    2820
atcttaagga acctctatca tgagaacatt gtgaagtaca aaggaatctg cacagaagac    2880
ggaggaaatg tattaagct catcatggaa tttctgcctt cgggaagcct taaggaatat    2940
cttccaaaga ataagaacaa aataaacctc aaacagcagc taaaatatgc cgttcagatt    3000
tgtaagggaa tggactattt gggttctcgg caatacgttc accggacttt ggcagcaaga    3060
aatgtccttg ttgagagtga acaccaagtg aaaattggag acttcggttt aaccaaagca    3120
attgaaaccg ataaggagta ttacaccgtc aaggatgacc gggacagccc tgtgttttgg    3180
tatgctccag aatgttttaat gcaatctaaa ttttatattg cctctgacgt ctggtctttt    3240
ggagtcactc tgcatgagct gctgacttac tgtgattcag attctagtcc catggctttg    3300
ttcctgaaaa tgataggccc aacccatggc cagatgacag tcacaagact tgtgaatacg    3360
```

-continued

```
ttaaagaag gaaaacgcct gccgtgccca cctaactgtc cagatgaggt ttatcagctt    3420
atgagaaaat gctgggaatt ccaaccatcc aatcggacaa gctttcagaa ccttattgaa    3480
ggatttgaag cacttttaaa ataagaagca tgaataacat ttaaattcca cagattatca    3540
a                                                                   3541
```

<210> SEQ ID NO 8
<211> LENGTH: 1142
<212> TYPE: PRT
<213> ORGANISM: Homo sapiens

<400> SEQUENCE: 8

```
Met Ala Phe Cys Ala Lys Met Arg Ser Ser Lys Lys Thr Glu Val Asn
1               5                   10                  15

Leu Glu Ala Pro Glu Pro Gly Val Glu Val Ile Phe Tyr Leu Ser Asp
            20                  25                  30

Arg Glu Pro Leu Arg Leu Gly Ser Gly Glu Tyr Thr Ala Glu Glu Leu
        35                  40                  45

Cys Ile Arg Ala Ala Gln Ala Cys Arg Ile Ser Pro Leu Cys His Asn
    50                  55                  60

Leu Phe Ala Leu Tyr Asp Glu Asn Thr Lys Leu Trp Tyr Ala Pro Asn
65                  70                  75                  80

Arg Thr Ile Thr Val Asp Asp Lys Met Ser Leu Arg Leu His Tyr Arg
                85                  90                  95

Met Arg Phe Tyr Phe Thr Asn Trp His Gly Thr Asn Asp Asn Glu Gln
            100                 105                 110

Ser Val Trp Arg His Ser Pro Lys Lys Gln Lys Asn Gly Tyr Glu Lys
        115                 120                 125

Lys Lys Ile Pro Asp Ala Thr Pro Leu Leu Asp Ala Ser Ser Leu Glu
    130                 135                 140

Tyr Leu Phe Ala Gln Gly Gln Tyr Asp Leu Val Lys Cys Leu Ala Pro
145                 150                 155                 160

Ile Arg Asp Pro Lys Thr Glu Gln Asp Gly His Asp Ile Glu Asn Glu
                165                 170                 175

Cys Leu Gly Met Ala Val Leu Ala Ile Ser His Tyr Ala Met Met Lys
            180                 185                 190

Lys Met Gln Leu Pro Glu Leu Pro Lys Asp Ile Ser Tyr Lys Arg Tyr
        195                 200                 205

Ile Pro Glu Thr Leu Asn Lys Ser Ile Arg Gln Arg Asn Leu Leu Thr
    210                 215                 220

Arg Met Arg Ile Asn Asn Val Phe Lys Asp Phe Leu Lys Glu Phe Asn
225                 230                 235                 240

Asn Lys Thr Ile Cys Asp Ser Ser Val Ser Thr His Asp Leu Lys Val
                245                 250                 255

Lys Tyr Leu Ala Thr Leu Glu Thr Leu Thr Lys His Tyr Gly Ala Glu
            260                 265                 270

Ile Phe Glu Thr Ser Met Leu Leu Ile Ser Ser Glu Asn Glu Met Asn
        275                 280                 285

Trp Phe His Ser Asn Asp Gly Gly Asn Val Leu Tyr Tyr Glu Val Met
    290                 295                 300

Val Thr Gly Asn Leu Gly Ile Gln Trp Arg His Lys Pro Asn Val Val
305                 310                 315                 320

Ser Val Glu Lys Glu Lys Asn Lys Leu Lys Arg Lys Lys Leu Glu Asn
                325                 330                 335

Lys Asp Lys Lys Asp Glu Glu Lys Asn Lys Ile Arg Glu Glu Trp Asn
```

-continued

```
                340                 345                 350
Asn Phe Ser Phe Phe Pro Glu Ile Thr His Ile Val Ile Lys Glu Ser
            355                 360                 365
Val Val Ser Ile Asn Lys Gln Asp Asn Lys Met Glu Leu Lys Leu
370                 375                 380
Ser Ser His Glu Glu Ala Leu Ser Phe Val Ser Leu Val Asp Gly Tyr
385                 390                 395                 400
Phe Arg Leu Thr Ala Asp Ala His His Tyr Leu Cys Thr Asp Val Ala
                405                 410                 415
Pro Pro Leu Ile Val His Asn Ile Gln Asn Gly Cys His Gly Pro Ile
            420                 425                 430
Cys Thr Glu Tyr Ala Ile Asn Lys Leu Arg Gln Glu Gly Ser Glu Glu
            435                 440                 445
Gly Met Tyr Val Leu Arg Trp Ser Cys Thr Asp Phe Asp Asn Ile Leu
    450                 455                 460
Met Thr Val Thr Cys Phe Glu Lys Ser Glu Gln Val Gln Gly Ala Gln
465                 470                 475                 480
Lys Gln Phe Lys Asn Phe Gln Ile Glu Val Gln Lys Gly Arg Tyr Ser
                485                 490                 495
Leu His Gly Ser Asp Arg Ser Phe Pro Ser Leu Gly Asp Leu Met Ser
            500                 505                 510
His Leu Lys Lys Gln Ile Leu Arg Thr Asp Asn Ile Ser Phe Met Leu
            515                 520                 525
Lys Arg Cys Cys Gln Pro Lys Pro Arg Glu Ile Ser Asn Leu Leu Val
            530                 535                 540
Ala Thr Lys Lys Ala Gln Glu Trp Gln Pro Val Tyr Pro Met Ser Gln
545                 550                 555                 560
Leu Ser Phe Asp Arg Ile Leu Lys Lys Asp Leu Val Gln Gly Glu His
                565                 570                 575
Leu Gly Arg Gly Thr Arg Thr His Ile Tyr Ser Gly Thr Leu Met Asp
            580                 585                 590
Tyr Lys Asp Asp Glu Gly Thr Ser Glu Glu Lys Lys Ile Lys Val Ile
        595                 600                 605
Leu Lys Val Leu Asp Pro Ser His Arg Asp Ile Ser Leu Ala Phe Phe
    610                 615                 620
Glu Ala Ala Ser Met Met Arg Gln Val Ser His Lys His Ile Val Tyr
625                 630                 635                 640
Leu Tyr Gly Val Cys Val Arg Asp Val Glu Asn Ile Met Val Glu Glu
                645                 650                 655
Phe Val Glu Gly Gly Pro Leu Asp Leu Phe Met His Arg Lys Ser Asp
            660                 665                 670
Val Leu Thr Thr Pro Trp Lys Phe Lys Val Ala Lys Gln Leu Ala Ser
        675                 680                 685
Ala Leu Ser Tyr Leu Glu Asp Lys Asp Leu Val His Gly Asn Val Cys
    690                 695                 700
Thr Lys Asn Leu Leu Leu Ala Arg Glu Gly Ile Asp Ser Glu Cys Gly
705                 710                 715                 720
Pro Phe Ile Lys Leu Ser Asp Pro Gly Ile Pro Ile Thr Val Leu Ser
                725                 730                 735
Arg Gln Glu Cys Ile Glu Arg Ile Pro Trp Ile Ala Pro Glu Cys Val
            740                 745                 750
Glu Asp Ser Lys Asn Leu Ser Val Ala Ala Asp Lys Trp Ser Phe Gly
            755                 760                 765
```

Thr Thr Leu Trp Glu Ile Cys Tyr Asn Gly Glu Ile Pro Leu Lys Asp
770                 775                 780

Lys Thr Leu Ile Glu Lys Glu Arg Phe Tyr Glu Ser Arg Cys Arg Pro
785                 790                 795                 800

Val Thr Pro Ser Cys Lys Glu Leu Ala Asp Leu Met Thr Arg Cys Met
                805                 810                 815

Asn Tyr Asp Pro Asn Gln Arg Pro Phe Phe Arg Ala Ile Met Arg Asp
            820                 825                 830

Ile Asn Lys Leu Glu Glu Gln Asn Pro Asp Ile Val Ser Arg Lys Lys
        835                 840                 845

Asn Gln Pro Thr Glu Val Asp Pro Thr His Phe Glu Lys Arg Phe Leu
    850                 855                 860

Lys Arg Ile Arg Asp Leu Gly Glu Gly His Phe Gly Lys Val Glu Leu
865                 870                 875                 880

Cys Arg Tyr Asp Pro Glu Asp Asn Thr Gly Glu Gln Val Ala Val Lys
                885                 890                 895

Ser Leu Lys Pro Glu Ser Gly Gly Asn His Ile Ala Asp Leu Lys Lys
            900                 905                 910

Glu Ile Glu Ile Leu Arg Asn Leu Tyr His Glu Asn Ile Val Lys Tyr
        915                 920                 925

Lys Gly Ile Cys Thr Glu Asp Gly Gly Asn Gly Ile Lys Leu Ile Met
    930                 935                 940

Glu Phe Leu Pro Ser Gly Ser Leu Lys Glu Tyr Leu Pro Lys Asn Lys
945                 950                 955                 960

Asn Lys Ile Asn Leu Lys Gln Gln Leu Lys Tyr Ala Val Gln Ile Cys
                965                 970                 975

Lys Gly Met Asp Tyr Leu Gly Ser Arg Gln Tyr Val His Arg Asp Leu
            980                 985                 990

Ala Ala Arg Asn Val Leu Val Glu Ser Glu His Gln Val Lys Ile Gly
        995                 1000                1005

Asp Phe Gly Leu Thr Lys Ala Ile Glu Thr Asp Lys Glu Tyr Tyr Thr
    1010                1015                1020

Val Lys Asp Asp Arg Asp Ser Pro Val Phe Trp Tyr Ala Pro Glu Cys
1025                1030                1035                1040

Leu Met Gln Ser Lys Phe Tyr Ile Ala Ser Asp Val Trp Ser Phe Gly
                1045                1050                1055

Val Thr Leu His Glu Leu Leu Thr Tyr Cys Asp Ser Asp Ser Ser Pro
            1060                1065                1070

Met Ala Leu Phe Leu Lys Met Ile Gly Pro Thr His Gly Gln Met Thr
        1075                1080                1085

Val Thr Arg Leu Val Asn Thr Leu Lys Glu Gly Lys Arg Leu Pro Cys
    1090                1095                1100

Pro Pro Asn Cys Pro Asp Glu Val Tyr Gln Leu Met Arg Lys Cys Trp
1105                1110                1115                1120

Glu Phe Gln Pro Ser Asn Arg Thr Ser Phe Gln Asn Leu Ile Glu Gly
                1125                1130                1135

Phe Glu Ala Leu Leu Lys
            1140

<210> SEQ ID NO 9
<211> LENGTH: 60
<212> TYPE: DNA
<213> ORGANISM: Homo sapiens

<400> SEQUENCE: 9

```
cggacaagct tcagaacct tattgaagga tttgaagcac ttttaaaata agaagcatga      60
```

<210> SEQ ID NO 10
<211> LENGTH: 4157
<212> TYPE: DNA
<213> ORGANISM: Homo sapiens

<400> SEQUENCE: 10

```
agcggggcgg ggcgccagcg ctgccttttc tcctgccggg tagtttcgct ttcctgcgca      60
gagtctgcgg aggggctcgg ctgcaccggg gggatcgcgc ctggcagacc ccagaccgag     120
cagaggcgac ccagcgcgct cgggagaggc tgcaccgccg cgcccccgcc tagcccttcc     180
ggatcctgcg cgcagaaaag tttcatttgc tgtatgccat cctcgagagc tgtctaggtt     240
aacgttcgca ctctgtgtat ataacctcga cagtcttggc acctaacgtg ctgtgcgtag     300
ctgctccttt ggttgaatcc ccaggccctt gttggggcac aaggtggcag gatgtctcag     360
tggtacgaac ttcagcagct tgactcaaaa ttcctggagc aggttcacca gctttatgat     420
gacagttttc ccatggaaat cagacagtac ctggcacagt ggttagaaaa gcaagactgg     480
gagcacgctg ccaatgatgt ttcatttgcc accatccgtt tcatgaccct cctgtcacag     540
ctggatgatc aatatagtcg ctttctcttg gagaataact tcttgctaca gcataacata     600
aggaaaagca agcgtaatct tcaggataat tttcaggaag acccaatcca gatgtctatg     660
atcatttaca gctgtctgaa ggaagaaagg aaaattctgg aaaacgccca gagatttaat     720
caggctcagt cggggaatat tcagagcaca gtgatgttag acaaacagaa agagcttgac     780
agtaaagtca gaaatgtgaa ggacaaggtt atgtgtatag agcatgaaat caagagcctg     840
gaagatttac aagatgaata tgacttcaaa tgcaaaacct tgcagaacag agaacacgag     900
accaatggtg tggcaaagag tgatcagaaa caagaacagc tgttactcaa gaagatgtat     960
ttaatgcttg acaataagag aaaggaagta gttcacaaaa taatagagtt gctgaatgtc    1020
actgaactta cccagaatgc cctgattaat gatgaactag tggagtggaa gcggagacag    1080
cagagcgcct gtattggggg gccgcccaat gcttgcttgg atcagctgca gaactggttc    1140
actatagttg cggagagtct gcagcaagtt cggcagcagc ttaaaaagtt ggaggaattg    1200
gaacagaaat acacctacga acatgaccct atcacaaaaa acaaacaagt gttatgggac    1260
cgcaccttca gtcttttcca gcagctcatt cagagctcgt tgtggtgga aagacagccc    1320
tgcatgccaa cgcaccctca gaggccgctg gtcttgaaga caggggtcca gttcactgtg    1380
aagttgagac tgttggtgaa attgcaagag ctgaattata atttgaaagt caagtcttta    1440
tttgataaag atgtgaatga gagaaataca gtaaaaggat ttaggaagtt caacatttg    1500
ggcacgcaca caaaagtgat gaacatggag gagtccacca atggcagtct ggcggctgaa    1560
tttcggcacc tgcaattgaa agaacagaaa aatgctggca ccagaacgaa tgagggtcct    1620
ctcatcgtta ctgaagagct tcactccctt agttttgaaa cccaattgtg ccagcctggt    1680
ttggtaattg acctcgagac gacctctctg cccgttgtgg tgatctccaa cgtcagccag    1740
ctcccgagcg gttgggcctc catcctttgg tacaacatgc tggtggcgga acccaggaat    1800
ctgtccttct tcctgactcc accatgtgca cgatgggctc agctttcaga agtgctgagt    1860
tggcagtttt cttctgtcac caaaagaggt ctcaatgtgg accagctgaa catgttggga    1920
gagaagcttc ttggtcctaa cgccagcccc gatggtctca ttccgtggac gaggttttgt    1980
aaggaaaata taaatgataa aaattttccc ttctggcttt ggattgaaag catcctagaa    2040
ctcattaaaa aacacctgct ccctctctgg aatgatgggt gcatcatggg cttcatcagc    2100
```

```
aaggagcgag agcgtgccct gttgaaggac cagcagccgg ggaccttcct gctgcggttc    2160
agtgagagct cccgggaagg ggccatcaca ttcacatggg tggagcggtc ccagaacgga    2220
ggcgaacctg acttccatgc ggttgaaccc tacacgaaga aagaactttc tgctgttact    2280
ttccctgaca tcattcgcaa ttacaaagtc atggctgctg agaatattcc tgagaatccc    2340
ctgaagtatc tgtatccaaa tattgacaaa gaccatgcct ttggaaagta ttactccagg    2400
ccaaaggaag caccagagcc aatggaactt gatggccvta aggaactgg atatatcaag    2460
actgagttga tttctgtgtc tgaagttcac ccttctagac ttcagaccac agacaacctg    2520
ctccccatgt ctcctgagga gtttgacgag gtgtctcgga tagtgggctc tgtagaattc    2580
gacagtatga tgaacacagt atagagcatg aattttttc atcttctctg gcgacagttt    2640
tccttctcat ctgtgattcc ctcctgctac tctgttcctt cacatcctgt gtttctaggg    2700
aaatgaaaga aaggccagca aattcgctgc aacctgttga tagcaagtga attttctct    2760
aactcagaaa catcagttac tctgaagggc atcatgcatc ttactgaagg taaaattgaa    2820
aggcattctc tgaagagtgg gtttcacaag tgaaaaacat ccagatacac ccaaagtatc    2880
aggacgagaa tgagggtcct ttgggaaagg agaagttaag caacatctag caaatgttat    2940
gcataaagtc agtgcccaac tgttataggt tgttggataa atcagtggtt atttagggaa    3000
ctgcttgacg taggaacggt aaatttctgt gggagaattc ttacatgttt tctttgcttt    3060
aagtgtaact ggcagtttc cattggttta cctgtgaaat agttcaaagc caagtttata    3120
tacaattata tcagtcctct ttcaaaggta gccatcatgg atctggtagg gggaaaatgt    3180
gtattttatt acatctttca cattggctat ttaaagacaa agacaaattc tgtttcttga    3240
gaagagaata ttagctttac tgtttgttat ggcttaatga cactagctaa tatcaataga    3300
aggatgtaca tttccaaatt cacaagttgt gtttgatatc caaagctgaa tacattctgc    3360
tttcatcttg gtcacataca attattttta cagttctccc aagggagtta ggctattcac    3420
aaccactcat tcaaaagttg aaattaacca tagatgtaga taaactcaga aatttaattc    3480
atgtttctta aatgggctac tttgtccttt ttgttattag ggtggtattt agtctattag    3540
ccacaaaatt gggaaggag tagaaaaagc agtaactgac aacttgaata atacaccaga    3600
gataatatga gaatcagatc atttcaaaac tcatttccta tgtaactgca ttgagaactg    3660
catatgtttc gctgatatat gtgtttttca catttgcgaa tggttccatt ctctctcctg    3720
tacttttcc agacactttt ttgagtggat gatgtttcgt gaagtatact gtattttac     3780
cttttttcctt ccttatcact gacacaaaaa gtagattaag agatgggttt gacaaggttc    3840
ttcccttta catactgctg tctatgtggc tgtatcttgt ttttccacta ctgctaccac    3900
aactatatta tcatgcaaat gctgtattct tctttggtgg agataaagat ttcttgagtt    3960
ttgtttaaa attaaagcta agtatctgt attgcattaa atataatatg cacacagtgc     4020
tttccgtggc actgcataca atctgaggcc tcctctctca gttttatat agatggcgag    4080
aacctaagtt tcagttgatt ttacaattga aatgactaaa aaacaaagaa gacaacatta    4140
aaacaatatt gtttcta                                                   4157
```

<210> SEQ ID NO 11
<211> LENGTH: 750
<212> TYPE: PRT
<213> ORGANISM: Homo sapiens

<400> SEQUENCE: 11

```
Met Ser Gln Trp Tyr Glu Leu Gln Gln Leu Asp Ser Lys Phe Leu Glu
1               5                   10                  15
```

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Asn
            35                  40                  45

Asp Val Ser Phe Ala Thr Ile Arg Phe His Asp Leu Leu Ser Gln Leu
 50                  55                  60

Asp Asp Gln Tyr Ser Arg Phe Ser Leu Glu Asn Asn Phe Leu Leu Gln
 65                  70                  75                  80

His Asn Ile Arg Lys Ser Lys Arg Asn Leu Gln Asp Asn Phe Gln Glu
                85                  90                  95

Asp Pro Ile Gln Met Ser Met Ile Ile Tyr Ser Cys Leu Lys Glu Glu
                100                 105                 110

Arg Lys Ile Leu Glu Asn Ala Gln Arg Phe Asn Gln Ala Gln Ser Gly
                115                 120                 125

Asn Ile Gln Ser Thr Val Met Leu Asp Lys Gln Lys Glu Leu Asp Ser
 130                 135                 140

Lys Val Arg Asn Val Lys Asp Lys Val Met Cys Ile Glu His Glu Ile
145                 150                 155                 160

Lys Ser Leu Glu Asp Leu Gln Asp Glu Tyr Asp Phe Lys Cys Lys Thr
                165                 170                 175

Leu Gln Asn Arg Glu His Glu Thr Asn Gly Val Ala Lys Ser Asp Gln
                180                 185                 190

Lys Gln Glu Gln Leu Leu Leu Lys Lys Met Tyr Leu Met Leu Asp Asn
                195                 200                 205

Lys Arg Lys Glu Val Val His Lys Ile Ile Glu Leu Leu Asn Val Thr
 210                 215                 220

Glu Leu Thr Gln Asn Ala Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255

Asp Gln Leu Gln Asn Trp Phe Thr Ile Val Ala Glu Ser Leu Gln Gln
                260                 265                 270

Val Arg Gln Gln Leu Lys Lys Leu Glu Glu Leu Glu Gln Lys Tyr Thr
                275                 280                 285

Tyr Glu His Asp Pro Ile Thr Lys Asn Lys Gln Val Leu Trp Asp Arg
            290                 295                 300

Thr Phe Ser Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                325                 330                 335

Thr Gly Val Gln Phe Thr Val Lys Leu Arg Leu Leu Val Lys Leu Gln
            340                 345                 350

Glu Leu Asn Tyr Asn Leu Lys Val Lys Val Leu Phe Asp Lys Asp Val
            355                 360                 365

Asn Glu Arg Asn Thr Val Lys Gly Phe Arg Lys Phe Asn Ile Leu Gly
 370                 375                 380

Thr His Thr Lys Val Met Asn Met Glu Glu Ser Thr Asn Gly Ser Leu
385                 390                 395                 400

Ala Ala Glu Phe Arg His Leu Gln Leu Lys Glu Gln Lys Asn Ala Gly
                405                 410                 415

Thr Arg Thr Asn Glu Gly Pro Leu Ile Val Thr Glu Glu Leu His Ser
            420                 425                 430

Leu Ser Phe Glu Thr Gln Leu Cys Gln Pro Gly Leu Val Ile Asp Leu

```
                435              440              445
Glu Thr Thr Ser Leu Pro Val Val Ile Ser Asn Val Ser Gln Leu
            450              455              460
Pro Ser Gly Trp Ala Ser Ile Leu Trp Tyr Asn Met Leu Val Ala Glu
465              470              475              480
Pro Arg Asn Leu Ser Phe Phe Leu Thr Pro Cys Ala Arg Trp Ala
            485              490              495
Gln Leu Ser Glu Val Leu Ser Trp Gln Phe Ser Ser Val Thr Lys Arg
                500              505              510
Gly Leu Asn Val Asp Gln Leu Asn Met Leu Gly Glu Lys Leu Leu Gly
            515              520              525
Pro Asn Ala Ser Pro Asp Gly Leu Ile Pro Trp Thr Arg Phe Cys Lys
530              535              540
Glu Asn Ile Asn Asp Lys Asn Phe Pro Phe Trp Leu Trp Ile Glu Ser
545              550              555              560
Ile Leu Glu Leu Ile Lys Lys His Leu Leu Pro Leu Trp Asn Asp Gly
            565              570              575
Cys Ile Met Gly Phe Ile Ser Lys Glu Arg Glu Arg Ala Leu Leu Lys
            580              585              590
Asp Gln Gln Pro Gly Thr Phe Leu Leu Arg Phe Ser Glu Ser Ser Arg
            595              600              605
Glu Gly Ala Ile Thr Phe Thr Trp Val Glu Arg Ser Gln Asn Gly Gly
610              615              620
Glu Pro Asp Phe His Ala Val Glu Pro Tyr Thr Lys Lys Glu Leu Ser
625              630              635              640
Ala Val Thr Phe Pro Asp Ile Ile Arg Asn Tyr Lys Val Met Ala Ala
            645              650              655
Glu Asn Ile Pro Glu Asn Pro Leu Lys Tyr Leu Tyr Pro Asn Ile Asp
            660              665              670
Lys Asp His Ala Phe Gly Lys Tyr Tyr Ser Arg Pro Lys Glu Ala Pro
            675              680              685
Glu Pro Met Glu Leu Asp Gly Pro Lys Gly Thr Gly Tyr Ile Lys Thr
            690              695              700
Glu Leu Ile Ser Val Ser Glu Val His Pro Ser Arg Leu Gln Thr Thr
705              710              715              720
Asp Asn Leu Leu Pro Met Ser Pro Glu Glu Phe Asp Glu Val Ser Arg
            725              730              735
Ile Val Gly Ser Val Glu Phe Asp Ser Met Met Asn Thr Val
            740              745              750

<210> SEQ ID NO 12
<211> LENGTH: 60
<212> TYPE: DNA
<213> ORGANISM: Homo sapiens

<400> SEQUENCE: 12
atcagatcat ttcaaaactc atttcctatg taactgcatt gagaactgca tatgtttcgc    60

<210> SEQ ID NO 13
<211> LENGTH: 4953
<212> TYPE: DNA
<213> ORGANISM: Homo sapiens

<400> SEQUENCE: 13
ggtttccgga gctgcggcgg cgcagactgg gagggggagc cggggggttcc gacgtcgcag    60 ccgagggaac aagccccaac cggatcctgg acaggcaccc cggcttggcg ctgtctctcc   120
```

```
ccctcggctc ggagaggccc ttcggcctga gggagcctcg ccgcccgtcc ccggcacacg      180
cgcagccccg gcctctcggc tctgccggaa gaaacaggat ggcccaatgg aatcagctac      240
agcagcttga cacacggtac ctggagcagc tccatcagct ctacagtgac agcttcccaa      300
tggagctgcg gcagtttctg gccccttgga ttgagagtca agattgggca tatgcggcca      360
gcaaagaatc acatgccact ttggtgtttc ataatctcct gggagagatt gaccagcagt      420
atagccgctt cctgcaagag tcgaatgttc tctatcagca caatctacga agaatcaagc      480
agtttcttca gagcaggtat cttgagaagc caatggagat tgcccggatt gtggcccggt      540
gcctgtggga agaatcacgc cttctacaga ctgcagccac tgcggcccag caaggggggcc     600 aggccaacca ccccacagca gccgtggtga cggagaagca gcagatgctg gagcagcacc      660
ttcaggatgt ccggaagaga gtgcaggatc tagaacagaa aatgaaagtg gtagagaatc      720
tccaggatga cttttgatttc aactataaaa ccctcaagag tcaaggagac atgcaagatc      780
tgaatggaaa caaccagtca gtgaccaggc agaagatgca gcagctggaa cagatgctca      840
ctgcgctgga ccagatgcgg agaagcatcg tgagtgagct ggcggggctt ttgtcagcga      900
tggagtacgt gcagaaaact ctcacggacg aggagctggc tgactggaag aggcggcaac      960
agattgcctg cattggaggc ccgcccaaca tctgcctaga tcggctagaa aactggataa     1020
cgtcattagc agaatctcaa cttcagaccc gtcaacaaat taagaaactg gaggagttgc     1080
agcaaaaagt ttcctacaaa ggggacccca ttgtacagca ccggccgatg ctggaggaga     1140
gaatcgtgga gctgtttaga aacttaatga aaagtgccgtt tgtggtggag cggcagccct     1200
gcatgcccat gcatcctgac cggcccctcg tcatcaagac cggcgtccag ttcactacta     1260
aagtcaggtt gctggtcaaa ttccctgagt tgaattatca gcttaaaatt aaagtgtgca     1320
ttgacaaaga ctctggggac gttgcagctc tcagaggatc ccggaaattt aacattctgg     1380
gcacaaacac aaaagtgatg aacatggaag aatccaacaa cggcagcctc tctgcagaat     1440
tcaaacactt gaccctgagg gagcagagat gtgggaatgg gggccgagcc aattgtgatg     1500
cttccctgat tgtgactgag gagctgcacc tgatcacctt tgagaccgag gtgtatcacc     1560
aaggcctcaa gattgaccta gagacccact ccttgccagt tgtggtgatc tccaacatct     1620
gtcagatgcc aaatgcctgg gcgtccatcc tgtggtacaa catgctgacc aacaatccca     1680
agaatgtaaa cttttttacc aagcccccaa ttggaacctg ggatcaagtg gccgaggtcc     1740
tgagctggca gttctcctcc accaccaagc gaggactgag catcgagcag ctgactacac     1800
tggcagagaa actcttggga cctggtgtga attattcagg gtgtcagatc acatgggcta     1860
aattttgcaa agaaaacatg gctggcaagg gcttctcctt ctgggtctgg ctggacaata     1920
tcattgacct tgtgaaaaag tacatcctgg cccttttgaa cgaagggtac atcatgggct     1980
ttatcagtaa ggagcgggag cgggccatct tgagcactaa gcctccaggc accttcctgc     2040
taagattcag tgaaagcagc aaagaaggag gcgtcacttt cacttgggtg gagaaggaca     2100
tcagcggtaa gacccagatc cagtccgtgg aaccatacac aaaagcagcag ctgaacaaca     2160 tgtcatttgc tgaaatcatc atgggctata agatcatgga tgctaccaat atcctggtgt     2220
ctccactggt ctatctctat cctgacattc caaggagga ggcattcgga aagtattgtc      2280
ggccagagag ccaggagcat cctgaagctg acccaggcgc tgccccatac ctgaagacca     2340
agtttatctg tgtgacacca acgacctgca gcaataccat tgacctgccg atgtcccccc     2400
gcactttaga ttcattgatg cagtttggaa ataatggtga aggtgctgaa ccctcagcag     2460
gagggcagtt tgagtccctc acctttgaca tggagttgac ctcggagtgc gctacctccc     2520
```

```
ccatgtgagg agctgagaac ggaagctgca gaaagatacg actgaggcgc ctacctgcat   2580
tctgccaccc ctcacacagc caaaccccag atcatctgaa actactaact tgtggttcc    2640 agatttttt  taatctccta cttctgctat ctttgagcaa tctgggcact tttaaaata    2700 gagaaatgag tgaatgtggg tgatctgctt ttatctaaat gcaataagg atgtgttctc    2760 tgagacccat gatcagggga tgtggcgggg ggtggctaga gggagaaaaa ggaaatgtct   2820
tgtgttgttt tgttcccctg ccctcctttc tcagcagctt tttgttattg ttgttgttgt   2880
tcttagacaa gtgcctcctg gtgcctgcgg catccttctg cctgtttctg taagcaaatg   2940
ccacaggcca cctatagcta catactcctg gcattgcact ttttaacctt gctgacatcc   3000
aaatagaaga taggactatc taagccctag gtttcttttt aaattaagaa ataataacaa   3060
ttaaagggca aaaaacactg tatcagcata gcctttctgt atttaagaaa cttaagcagc   3120
cgggcatggt ggctcacgcc tgtaatccca gcactttggg aggccgaggc ggatcataag   3180
gtcaggagat caagaccatc ctggctaaca cggtgaaacc ccgtctctac taaaagtaca   3240
aaaaattagc tgggtgtggt ggtgggcgcc tgtagtccca gctactcggg aggctgaggc   3300
aggagaatcg cttgaacctg agaggcggag gttgcagtga gccaaaattg caccactgca   3360
cactgcactc catcctgggc gacagtctga gactctgtct caaaaaaaaa aaaaaaaaa    3420 agaaacttca gttaacagcc tccttggtgc tttaagcatt cagcttcctt caggctggta   3480
atttatataa tccctgaaac gggcttcagg tcaaaccctt aagacatctg aagctgcaac   3540
ctggcctttg gtgttgaaat aggaaggttt aaggagaatc taagcatttt agactttttt   3600
ttataaatag acttattttc ctttgtaatg tattggcctt ttagtgagta aggctgggca   3660
gagggtgctt acaaccttga ctcccttttct ccctggactt gatctgctgt ttcagaggct   3720
aggttgtttc tgtgggtgcc ttatcagggc tgggatactt ctgattctgg cttccttcct   3780
gccccaccct cccgacccca gtccccctga tcctgctaga ggcatgtctc cttgcgtgtc   3840
taaaggtccc tcatcctgtt tgttttagga atcctggtct caggacctca tggaagaaga   3900
gggggagaga gttacaggtt ggacatgatg cacactatgg ggccccagcg acgtgtctgg   3960
ttgagctcag ggaatatggt tcttagccag tttcttggtg atatccagtg gcacttgtaa   4020
tggcgtcttc attcagttca tgcagggcaa aggcttactg ataaacttga gtctgccctc   4080
gtatgagggt gtatacctgg cctccctctg aggctggtga ctcctccctg ctggggcccc   4140
acaggtgagg cagaacagct agagggcctc cccgcctgcc cgccttggct ggctagctcg   4200
cctctcctgt gcgtatggga acacctagca cgtgctggat gggctgcctc tgactcagag   4260
gcatggccgg atttgcaac  tcaaaaccac cttgcctcag ctgatcagag tttctgtgga   4320
attctgtttg ttaaatcaaa ttagctggtc tctgaattaa gggggagacg accttctcta   4380
agatgaacag ggttcgcccc agtcctcctg cctggagaca gttgatgtgt catgcagagc   4440
tcttacttct ccagcaacac tcttcagtac ataataagct taactgataa acagaatatt   4500
tagaaaggtg agacttgggc ttaccattgg gtttaaatca tagggaccta gggcgagggt   4560
tcagggcttc tctggagcag atattgtcaa gttcatggcc ttaggtagca tgtatctggt   4620
cttaactctg attgtagcaa aagttctgag aggagctgag ccctgttgtg gcccattaaa   4680
gaacagggtc ctcaggccct gcccgcttcc tgtccactgc cccctcccca tcccagccc   4740 agccgaggga atcccgtggg ttgcttacct acctataagg tggtttataa gctgctgtcc   4800
tggccactgc attcaaattc caatgtgtac ttcatagtgt aaaaatttat attattgtga   4860
ggttttttgt cttttttttt tttttttttt tttggtatat tgctgtatct actttaactt   4920
```
ccagaaataa acgttatata ggaaccgtaa aaa 4953

<210> SEQ ID NO 14
<211> LENGTH: 769
<212> TYPE: PRT
<213> ORGANISM: Homo sapiens

<400> SEQUENCE: 14

```
Met Ala Gln Trp Asn Gln Leu Gln Gln Leu Asp Thr Arg Tyr Leu Glu
1               5                   10                  15
Gln Leu His Gln Leu Tyr Ser Asp Ser Phe Pro Met Glu Leu Arg Gln
            20                  25                  30
Phe Leu Ala Pro Trp Ile Glu Ser Gln Asp Trp Ala Tyr Ala Ala Ser
        35                  40                  45
Lys Glu Ser His Ala Thr Leu Val Phe His Asn Leu Leu Gly Glu Ile
    50                  55                  60
Asp Gln Gln Tyr Ser Arg Phe Leu Gln Glu Ser Asn Val Leu Tyr Gln
65                  70                  75                  80
His Asn Leu Arg Arg Ile Lys Gln Phe Leu Gln Ser Arg Tyr Leu Glu
                85                  90                  95
Lys Pro Met Glu Ile Ala Arg Ile Val Ala Arg Cys Leu Trp Glu Glu
            100                 105                 110
Ser Arg Leu Leu Gln Thr Ala Ala Thr Ala Ala Gln Gln Gly Gly Gln
        115                 120                 125
Ala Asn His Pro Thr Ala Ala Val Val Thr Glu Lys Gln Gln Met Leu
    130                 135                 140
Glu Gln His Leu Gln Asp Val Arg Lys Arg Val Gln Asp Leu Glu Gln
145                 150                 155                 160
Lys Met Lys Val Val Glu Asn Leu Gln Asp Asp Phe Asp Phe Asn Tyr
                165                 170                 175
Lys Thr Leu Lys Ser Gln Gly Asp Met Gln Asp Leu Asn Gly Asn Asn
            180                 185                 190
Gln Ser Val Thr Arg Gln Lys Met Gln Gln Leu Glu Gln Met Leu Thr
        195                 200                 205
Ala Leu Asp Gln Met Arg Arg Ser Ile Val Ser Glu Leu Ala Gly Leu
    210                 215                 220
Leu Ser Ala Met Glu Tyr Val Gln Lys Thr Leu Thr Asp Glu Glu Leu
225                 230                 235                 240
Ala Asp Trp Lys Arg Arg Gln Gln Ile Ala Cys Ile Gly Gly Pro Pro
                245                 250                 255
Asn Ile Cys Leu Asp Arg Leu Glu Asn Trp Ile Thr Ser Leu Ala Glu
            260                 265                 270
Ser Gln Leu Gln Thr Arg Gln Gln Ile Lys Lys Leu Glu Glu Leu Gln
        275                 280                 285
Gln Lys Val Ser Tyr Lys Gly Asp Pro Ile Val Gln His Arg Pro Met
    290                 295                 300
Leu Glu Glu Arg Ile Val Glu Leu Phe Arg Asn Leu Met Lys Ser Ala
305                 310                 315                 320
Phe Val Val Glu Arg Gln Pro Cys Met Pro Met His Pro Asp Arg Pro
                325                 330                 335
Leu Val Ile Lys Thr Gly Val Gln Phe Thr Thr Lys Val Arg Leu Leu
            340                 345                 350
Val Lys Phe Pro Glu Leu Asn Tyr Gln Leu Lys Ile Lys Val Cys Ile
        355                 360                 365
```

-continued

Asp Lys Asp Ser Gly Asp Val Ala Ala Leu Arg Gly Ser Arg Lys Phe
370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
            405                 410                 415

Arg Cys Gly Asn Gly Arg Ala Asn Cys Asp Ala Ser Leu Ile Val
        420                 425                 430

Thr Glu Glu Leu His Leu Ile Thr Phe Glu Thr Glu Val Tyr His Gln
            435                 440                 445

Gly Leu Lys Ile Asp Leu Glu Thr His Ser Leu Pro Val Val Val Ile
450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
            485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
            515                 520                 525

Ala Glu Lys Leu Leu Gly Pro Gly Val Asn Tyr Ser Gly Cys Gln Ile
530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
            565                 570                 575

Leu Ala Leu Trp Asn Glu Gly Tyr Ile Met Gly Phe Ile Ser Lys Glu
            580                 585                 590

Arg Glu Arg Ala Ile Leu Ser Thr Lys Pro Pro Gly Thr Phe Leu Leu
            595                 600                 605

Arg Phe Ser Glu Ser Ser Lys Glu Gly Gly Val Thr Phe Thr Trp Val
            610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
            645                 650                 655

Tyr Lys Ile Met Asp Ala Thr Asn Ile Leu Val Ser Pro Leu Val Tyr
            660                 665                 670

Leu Tyr Pro Asp Ile Pro Lys Glu Glu Ala Phe Gly Lys Tyr Cys Arg
            675                 680                 685

Pro Glu Ser Gln Glu His Pro Glu Ala Asp Pro Gly Ala Ala Pro Tyr
690                 695                 700

Leu Lys Thr Lys Phe Ile Cys Val Thr Pro Thr Thr Cys Ser Asn Thr
705                 710                 715                 720

Ile Asp Leu Pro Met Ser Pro Arg Thr Leu Asp Ser Leu Met Gln Phe
            725                 730                 735

Gly Asn Asn Gly Glu Gly Ala Glu Pro Ser Ala Gly Gly Gln Phe Glu
            740                 745                 750

Ser Leu Thr Phe Asp Met Glu Leu Thr Ser Glu Cys Ala Thr Ser Pro
            755                 760                 765

Met

<210> SEQ ID NO 15
<211> LENGTH: 60

```
<212> TYPE: DNA
<213> ORGANISM: Homo sapiens

<400> SEQUENCE: 15
agtgaatgtg ggtgatctgc ttttatctaa atgcaaataa ggatgtgttc tctgagaccc    60

<210> SEQ ID NO 16
<211> LENGTH: 1610
<212> TYPE: DNA
<213> ORGANISM: Homo sapiens

<400> SEQUENCE: 16 gcttttgca aatgttgaat catggttctg tttctaagtt ggatcttttt tgttttctcc      60
ttgccaccct aatttgacat caaattctct cttgtgcatt gggccctggg tcattcaaac    120
ccaggtcacc tcattcccct tctctgttca cacctaatgt cttgaagagt aggtagcagc    180
agtgtgggct gaacctaggc cagcttgctt agcgggtcac cctgctgtga agtcctggca    240
ggtgttggta atgtgtggaa atgcagtcag caagtttgct ggggagtttg ataaaagtat    300
aaaacaaaac aaaaaaagcc tcggtataat tttgttccac gacttcttct gtagctttac    360
accagaagga aggaatgggc tacagcaggt agtggaggaa gaggggggtg agcaggtgta    420
ttaaaatagc ttacgggtaa ggcctaaaag gtcacccctc ggcccctct ccaaagaag      480 ggcatgggca cccccaggag aggatggccc caaaaacctt atttttatac atgagagtaa    540
ataaacatat ttttttaca aaaataactt ctgaatttat cagtgttttg ccgttaaaaa     600
tattcctcta tagtaaatta tttattggaa gatgactttt ttaaagctgc cgtttgcctt    660
ggcttggttt catacactga tttattttc tatgccaggc agtagagtct ctctgcctct     720
gaggagcagg ctacccgcat cccactcagc ccctccctac ccctcaagat tgatgaaaa     780 ttccaaccat gaggatgggt gcatcgggga agggtgagaa ggagagcctg cctgctcagg   840
gatccaggct cgtagagtca ctccctgccc gtctcccaga gatgcttcac cagcacctgc   900
ctctgagacc tcgctctctg ttccagcaac cctggttggg gggtcagact tgatacactt    960
tcaggttggg agtggaccca ccccagggcc tgctgaggac agagcagcca ggccgtcctg   1020
gctcactttg cagttggcac tgggttgggg aggaagagag ctgatgagtg tggcttccct   1080
gagctggggt ttccctgctt gtccagttgt gagctgtcct cggtgttacc gaggctgtgc   1140
ctagagagtg gagattttg atgaaaggtg tgctcgctct ctgcgttcta tcttctctct    1200
cctccttgtt cctgcaaacc acaagataaa ggtagtggtg tgtctcgacc ccatcagcct   1260
ctcacccact cccagacaca cacaagtcct caaaagtttc agctccgtgt gtgagatgtg   1320 caggttttt ctaggggta gggggagact aaaatcgaat ataacttaaa atgaaagtat     1380 acttttata attttctttt ttaaaacttg gtgaaattat ttcagataca tattttagtg   1440
tcaaggcaga ttagttattt agccaccaaa aaaagtatt gtgtacaatt tggggcctca    1500
aatttgactc tgcctcaaaa aaaagaaata tatcctatgc agagttacag tcacaaagtt  1560
gtgtatttta tgttacaata aagccttcct ctggaaggga aaaaaaaaa                1610

<210> SEQ ID NO 17
<211> LENGTH: 60
<212> TYPE: DNA
<213> ORGANISM: Homo sapiens

<400> SEQUENCE: 17
atcctatgca gagttacagt cacaaagttg tgtattttat gttacaataa agccttcctc    60
```

-continued

```
<210> SEQ ID NO 18
<211> LENGTH: 1216
<212> TYPE: DNA
<213> ORGANISM: Homo sapiens

<400> SEQUENCE: 18
ggcagctgca cggctcctgg ccccggagca tgcgcgagag ccgccccgga gcgccccgga      60 gcccccgcc gtcccgcccg cggcgtcccg cgccccgccg ccagcgcacc cccggacgct     120
atggcccacc cctccggctg ccccttctg taggatggta gcacacaacc aggtggcagc     180
cgacaatgca gtctccacag cagcagagcc ccgacggcgg ccagaacctt cctcctcttc     240
ctcctcctcg cccgcggccc ccgcgcgccc gcggccgtgc cccgcggtcc cggccccggc     300
ccccggcgac acgcacttcc gcacattccg ttcgcacgcc gattaccggc gcatcacgcg     360
cgccagcgcg ctcctggacg cctgcggatt ctactggggg ccctgagcg tgcacggggc     420 gcacgagcgg ctgcgcgccg agcccgtggg caccttcctg gtgcgcgaca gccgccagcg     480
gaactgcttt ttcgccctta gcgtgaagat ggcctcggga cccacgagca tccgcgtgca     540
ctttcaggcc ggccgctttc acctggatgg cagccgcgag agcttcgact gcctcttcga     600
gctgctggag cactacgtgg cggcgccgcg ccgcatgctg ggggccccgc tgcgccagcg     660
ccgcgtgcgg ccgctgcagg agctgtgccg ccagcgcatc gtggccaccg tgggccgcga     720
gaacctggct cgcatccccc tcaaccccgt cctccgcgac tacctgagct ccttcccctt     780
ccagatttga ccggcagcgc ccgccgtgca cgcagcatta actgggatgc cgtgttattt     840
tgttattact tgcctggaac catgtgggta ccctccccgg cctgggttgg agggagcgga     900
tgggtgtagg ggcgaggcgc ctcccgccct cggctggaga cgaggccgca gaccccttct     960
cacctcttga gggggtcctc cccctcctgg tgctccctct gggtcccct ggttgttgta    1020 gcagcttaac tgtatctgga gccaggacct gaactcgcac ctcctacctc ttcatgttta    1080 catatacccca gtatctttgc acaaaccagg ggttggggga gggtctctgg ctttattttt    1140
ctgctgtgca gaatcctatt ttatatttt taaagtcagt ttaggtaata aactttatta    1200
tgaaagtttt tttttt                                                    1216

<210> SEQ ID NO 19
<211> LENGTH: 211
<212> TYPE: PRT
<213> ORGANISM: Homo sapiens

<400> SEQUENCE: 19

Met Val Ala His Asn Gln Val Ala Asp Asn Ala Val Ser Thr Ala
1               5                   10                  15

Ala Glu Pro Arg Arg Arg Pro Glu Pro Ser Ser Ser Ser Ser Ser
                20                  25                  30

Pro Ala Ala Pro Ala Arg Pro Arg Pro Cys Pro Ala Val Pro Ala Pro
            35                  40                  45

Ala Pro Gly Asp Thr His Phe Arg Thr Phe Arg Ser His Ala Asp Tyr
        50                  55                  60

Arg Arg Ile Thr Arg Ala Ser Ala Leu Leu Asp Ala Cys Gly Phe Tyr
65                  70                  75                  80

Trp Gly Pro Leu Ser Val His Gly Ala His Glu Arg Leu Arg Ala Glu
                85                  90                  95

Pro Val Gly Thr Phe Leu Val Arg Asp Ser Arg Gln Arg Asn Cys Phe
            100                 105                 110

Phe Ala Leu Ser Val Lys Met Ala Ser Gly Pro Thr Ser Ile Arg Val
        115                 120                 125
```

```
His Phe Gln Ala Gly Arg Phe His Leu Asp Gly Ser Arg Glu Ser Phe
    130                 135                 140

Asp Cys Leu Phe Glu Leu Leu Glu His Tyr Val Ala Ala Pro Arg Arg
145                 150                 155                 160

Met Leu Gly Ala Pro Leu Arg Gln Arg Arg Val Arg Pro Leu Gln Glu
                165                 170                 175

Leu Cys Arg Gln Arg Ile Val Ala Thr Val Gly Arg Glu Asn Leu Ala
                180                 185                 190

Arg Ile Pro Leu Asn Pro Val Leu Arg Asp Tyr Leu Ser Ser Phe Pro
            195                 200                 205

Phe Gln Ile
    210

<210> SEQ ID NO 20
<211> LENGTH: 60
<212> TYPE: DNA
<213> ORGANISM: Homo sapiens

<400> SEQUENCE: 20
tcgcacctcc tacctcttca tgtttacata tacccagtat ctttgcacaa accaggggtt    60

<210> SEQ ID NO 21
<211> LENGTH: 2746
<212> TYPE: DNA
<213> ORGANISM: Homo sapiens

<400> SEQUENCE: 21
ggctccgact tggactccct gctccgctgc tgccgcttcg gccccgcacg cagccagccg      60
ccagccgccc gccggcccca gctccgccg cggcccttg ccgcggtccc tctcctggtc      120
ccctcccggt tggtccgggg gtgcgcaggg ggcagggcgg gcgcccaggg gaagctcgag    180
ggacgcgcgc gcgaaggctc ctttgtggac ttcacggccg ccaacatctg gcgcagcgc    240 gggccaccgc tggccgtctc gccgccgcgt cgccttgggg acccgagggg gctcagcccc    300
aaggacggag acttcgattc gggaccagcc ccccgggatg cggtagcggc cgctgtgcgg    360
aggccgcgaa gcagctgcag ccgccgccgc gcagatccac gctggctccg tgcgccatgg    420
tcacccacag caagtttccc gccgccggga tgagccgccc cctggacacc agcctgcgcc    480
tcaagacctt cagctccaag agcgagtacc agctggtggt gaacgcagtg cgcaagctgc    540
aggagagcgg cttctactgg agcgcagtga ccggcggcga ggcgaacctg ctgctcagtg    600
ccgagcccgc cggcaccttt ctgatccgcg acagctcgga ccagcgccac ttcttcacgc    660
tcagcgtcaa gacccagtct gggaccaaga acctgcgcat ccagtgtgag gggggcagct    720
tctctctgca gagcgatccc ggagcacgc agcccgtgcc ccgcttcgac tgcgtgctca    780
agctggtgca ccactacatg ccgccccctg gagccccctc cttccccctcg ccacctactg    840 aaccctcctc cgaggtgccc gagcagccgt ctgcccagcc actccctggg agtccccca    900 gaagagccta ttacatctac tccggggggcg agaagatccc cctggtgttg agccggcccc    960
tctcctccaa cgtggccact cttcagcatc tctgtcggaa gaccgtcaac ggccacctgg   1020
actcctatga gaaagtcacc cagctgccgg ggcccattcg ggagttcctg gaccagtacg   1080 atgcccgct ttaaggggta aagggcgcaa agggcatggg tcgggagagg ggacgcaggc    1140
ccctctcctc cgtggcacat ggcacaagca caagaagcca accaggagag agtcctgtag   1200 ctctggggg aaagagggcg gacaggcccc tccctctgcc ctctccctgc agaatgtggc   1260
aggcggacct ggaatgtgtt ggagggaagg gggagtacca cctgagtctc cagcttctcc   1320
```

```
ggaggagcca gctgtcctgg tgggacgata gcaaccacaa gtggattctc cttcaattcc    1380
tcagcttccc ctctgcctcc aaacagggga cacttcggga atgctgaact aatgagaact    1440
gccagggaat cttcaaactt tccaacggaa cttgtttgct cttttgatttg gtttaaacct   1500 gagctggttg tggagcctgg gaaaggtgga agagagagag gtcctgaggg ccccagggct    1560
gcgggctggc gaaggaaatg gtcacacccc ccgcccaccc caggcgagga tcctggtgac    1620
atgctcctct ccctggctcc ggggagaagg gcttggggtg acctgaaggg aaccatcctg    1680 gtacccaca tcctctcctc cgggacagtc accgaaaaca caggttccaa agtctacctg     1740
gtgcctgaga gcccagggcc cttcctccgt tttaaggggg aagcaacatt tggaggggat    1800
ggatgggctg gtcagctggt ctccttttcc tactcatact ataccttcct gtacctgggt    1860
ggatggagcg ggaggatgga ggagacggga catctttcac ctcaggctcc tggtagagaa    1920
gacaggggat tctactctgt gcctcctgac tatgtctggc taagagattc gccttaaatg    1980
ctccctgtcc catggagagg gacccagcat aggaaagcca catactcagc ctggatgggg    2040
ggagaggctg agggactcac tggagggcac caagccagcc cacagccagg gaagtgggga    2100 ggggggggcgg aaacccatgc ctcccagctg agcactggga atgtcagccc agtaagtatt   2160
ggccagtcag gcgcctcgtg gtcagagcag agccaccagg tcccactgcc ccgagccctg    2220
cacagccctc cctcctgcct gggtggggga ggctggaggt cattggagag ctggactgc     2280 tgccaccccg ggtgctcccg ctctgccata gcactgatca gtgacaattt acaggaatgt    2340
agcagcgatg gaattacctg gaacagtttt ttgtttttgt ttttgttttt gttttttgtgg  2400 gggggggcaa ctaaacaaac acaaagtatt ctgtgtcagg tattgggctg gacagggcag    2460
ttgtgtgttg gggtggtttt tttctctatt ttttgtttg tttcttgttt ttaataatg      2520 tttacaatct gcctcaatca ctctgtcttt tataaagatt ccacctccag tcctctctcc    2580
tcccccctac tcaggcccct gaggctatta ggagatgctt gaagaactca acaaaatccc    2640
aatccaagtc aaactttgca catatttata tttatattca gaaagaaac attcagtaa      2700 tttataataa agagcactat ttttaatga aaaaaaaaa aaaaaa                    2746
```

<210> SEQ ID NO 22
<211> LENGTH: 225
<212> TYPE: PRT
<213> ORGANISM: Homo sapiens

<400> SEQUENCE: 22

```
Met Val Thr His Ser Lys Phe Pro Ala Ala Gly Met Ser Arg Pro Leu
1               5                   10                  15

Asp Thr Ser Leu Arg Leu Lys Thr Phe Ser Ser Lys Ser Glu Tyr Gln
            20                  25                  30

Leu Val Val Asn Ala Val Arg Lys Leu Gln Glu Ser Gly Phe Tyr Trp
        35                  40                  45

Ser Ala Val Thr Gly Gly Glu Ala Asn Leu Leu Ser Ala Glu Pro
    50                  55                  60

Ala Gly Thr Phe Leu Ile Arg Asp Ser Ser Asp Gln Arg His Phe Phe
65                  70                  75                  80

Thr Leu Ser Val Lys Thr Gln Ser Gly Thr Lys Asn Leu Arg Ile Gln
                85                  90                  95

Cys Glu Gly Gly Ser Phe Ser Leu Gln Ser Asp Pro Arg Ser Thr Gln
            100                 105                 110

Pro Val Pro Arg Phe Asp Cys Val Leu Lys Leu Val His His Tyr Met
        115                 120                 125
```

```
Pro Pro Pro Gly Ala Pro Ser Phe Pro Ser Pro Thr Glu Pro Ser
    130                 135                 140
Ser Glu Val Pro Glu Gln Pro Ser Ala Gln Pro Leu Pro Gly Ser Pro
145                 150                 155                 160
Pro Arg Arg Ala Tyr Tyr Ile Tyr Ser Gly Gly Glu Lys Ile Pro Leu
                165                 170                 175
Val Leu Ser Arg Pro Leu Ser Ser Asn Val Ala Thr Leu Gln His Leu
            180                 185                 190
Cys Arg Lys Thr Val Asn Gly His Leu Asp Ser Tyr Glu Lys Val Thr
        195                 200                 205
Gln Leu Pro Gly Pro Ile Arg Glu Phe Leu Asp Gln Tyr Asp Ala Pro
    210                 215                 220
Leu
225

<210> SEQ ID NO 23
<211> LENGTH: 60
<212> TYPE: DNA
<213> ORGANISM: Homo sapiens

<400> SEQUENCE: 23
tggaccagta cgatgccccg ctttaagggg taaagggcgc aaagggcatg ggtcgggaga      60

<210> SEQ ID NO 24
<211> LENGTH: 4298
<212> TYPE: DNA
<213> ORGANISM: Homo sapiens

<400> SEQUENCE: 24
cagacaggat attcactgct gtggcaaggc ctgtagagag tttcgaagtt aggaggactc      60
aagacggtcc ctccctggac ttttctgaag gggctcaaaa gatgacacgc gccagagctg     120
gaaggcgtcg ccaattggtc caacttttcc ctcctccctt tttgcggatg agaaaaactg     180
aggcccaggt ttgggatttc cagagcccgg gatttcccgg caacgccgac aaccacattc     240
ccccggctat tctgacccgc cccggttccg ggacgctccc tgggagccgc cgccgagggc     300
ctgctgggac tcccggggac cccgccgtcg gggcagcccc cacgcccggc gccgcccgcc     360
ggaacggcgc cgctgttgcg cacttgcagg ggagccggcg actgagggcg aggcagggag     420
ggagcaagcg gggctgggag ggctgctggc gcgggctcgc cggctgtgta tggtctatcg     480
caggcagctg acctttgagg aggaaatcgc tgctctccgc tccttcctgt agtaacagcc     540
gccgctgccg ccgccgccag gaaccccggc cgggagcgag agccgcgggg cgcagagccg     600
gcccggctgc cggacggtgc ggccccacca ggtgaacggc catggcgggc tggatccagg     660
cccagcagct gcagggagac gcgctgcgcc agatgcaggt gctgtacggc agcacttcc      720 ccatcgaggt ccggcactac ttggcccagt ggattgagag ccagccatgg gatgccattg     780
acttggacaa tcccccaggac agagcccaag ccacccagct cctggagggc ctggtgcagg     840
agctgcagaa gaaggcggag caccaggtgg gggaagatgg gtttttactg aagatcaagc     900
tggggcacta cgccacgcag ctccagaaaa catatgaccg ctgccccctg gagctggtcc     960
gctgcatccg gcacattctg tacaatgaac agaggctggt ccgagaagcc aacaattgca    1020
gctctccggc tgggatcctg gttgacgcca tgtcccagaa gcaccttcag atcaaccaga    1080
catttgagga gctgcgactg gtcacgcagg acacagagaa tgagctgaag aaactgcagc    1140
agactcagga gtacttcatc atccagtacc aggagagcct gaggatccaa gctcagtttg    1200
```

-continued

```
cccagctggc ccagctgagc ccccaggagc gtctgagccg ggagacggcc ctccagcaga    1260
agcaggtgtc tctggaggcc tggttgcagc gtgaggcaca gacactgcag cagtaccgcg    1320
tggagctggc cgagaagcac cagaagaccc tgcagctgct gcggaagcag cagaccatca    1380
tcctggatga cgagctgatc cagtggaagc ggcggcagca gctggccggg aacggcgggc    1440
cccccgaggg cagcctggac gtgctacagt cctggtgtga agttggcc gagatcatct      1500
ggcagaaccg gcagcagatc cgcagggctg agcacctctg ccagcagctg ccatccccg     1560
gcccagtgga ggagatgctg gccgaggtca cgccaccat cacggacatt atctcagccc     1620
tggtgaccag cacattcatc attgagaagc agcctcctca ggtcctgaag acccagacca    1680
agtttgcagc caccgtacgc ctgctggtgg gcgggaagct gaacgtgcac atgaatcccc    1740
cccaggtgaa ggccaccatc atcagtgagc agcaggccaa gtctctgctt aaaaatgaga    1800
acacccgcaa cgagtgcagt ggtgagatcc tgaacaactg ctgcgtgatg gagtaccacc    1860
aagccacggg caccctcagt gcccacttca ggaacatgtc actgaagagg atcaagcgtg    1920
ctgaccggcg gggtgcagag tccgtgacag aggagaagtt cacagtcctg tttgagtctc    1980
agttcagtgt tggcagcaat gagcttgtgt tccaggtgaa gactctgtcc ctacctgtgg    2040
ttgtcatcgt ccacggcagc caggaccaca atgccacggc tactgtgctg tgggacaatg    2100
cctttgctga gccgggcagg gtgccatttg ccgtgcctga caaagtgctg tggccgcagc    2160
tgtgtgaggc gctcaacatg aaattcaagg ccgaagtgca gagcaaccgg ggcctgacca    2220
aggagaacct cgtgttcctg gcgcagaaac tgttcaacaa cagcagcagc cacctggagg    2280
actacagtgg cctgtccgtg tcctggtccc agttcaacag ggagaacttg ccgggctgga    2340
actacacctt ctggcagtgg tttgacgggg tgatggaggt gttgaagaag caccacaagc    2400
cccactggaa tgatggggcc atcctaggtt ttgtgaataa gcaacaggcc cacgacctgc    2460
tcatcaacaa gcccgacggg accttcttgt tgcgctttag tgactcagaa atcgggggca    2520
tcaccatcgc ctggaagttt gactcccgg aacgcaacct gtggaacctg aaaccattca    2580
ccacgcggga tttctccatc aggtccctgg ctgaccggct gggggacctg agctatctca    2640
tctatgtgtt tcctgaccgc cccaaggatg aggtcttctc caagtactac actcctgtgc    2700
tggctaaagc tgttgatgga tatgtgaaac cacagatcaa gcaagtggtc cctgagtttg    2760
tgaatgcatc tgcagatgct gggggcagca gcgccacgta catggaccag gccccctccc    2820
cagctgtgtg ccccccaggct ccctataaca tgtacccaca gaaccctgac catgtactcg    2880
atcaggatgg agaattcgac ctggatgaga ccatggatgt ggccaggcac gtggaggaac    2940
tcttacgccg accaatggac agtcttgact cccgcctctc gccccctgcc ggtcttttca    3000
cctctgccag aggctcccte tcatgaatgt ttgaatccca cgcttctctt tggaaacaat    3060
atgcaatgtg aagcggtcgt gttgtgagtt tagtaaggtt gtgtacactg acacctttgc    3120
aggcatgcat gtgcttgtgt gtgtgtgtgt gtgtgtgtcc ttgtgcatga gctacgcctg    3180
cctcccctgt gcagtcctgg gatgtggctg cagcagcggt ggcctctttt cagatcatgg    3240
catccaagag tgcgccgagt ctgtctctgt catggtagag accgagcctc tgtcactgca    3300
ggcactcaat gcagccagac ctattcctcc tgggcccctc atctgctcag cagctatttg    3360
aatgagatga ttcagaaggg gaggggagac aggtaacgtc tgtaagctga agtttcactc    3420
cggagtgaga agctttgccc tcctaagaga gagagacaga gagacagaga gagagaaaga    3480
gagagtgtgt gggtctatgt aaatgcatct gtcctcatgt gttgatgtaa ccgattcatc    3540
tctcagaagg gaggctgggg gttcatttc gagtagtatt ttatacttta gtgaacgtgg    3600
```

-continued

```
actccagact ctctgtgaac cctatgagag cgcgtctggg cccggccatg tccttagcac    3660 agggggggccg ccggtttgag tgagggtttc tgagctgctc tgaattagtc cttgcttggc    3720
tgcttggcct tgggcttcat tcaagtctat gatgctgttg cccacgtttc ccgggatata    3780
tattctctcc cctccgttgg gccccagcct tctttgcttg cctctctgtt tgtaaccttg    3840
tcgacaaaga ggtagaaaag attgggtcta ggatatggtg ggtggacagg ggccccggga    3900
cttggagggt tggtcctctt gcctcctgga aaaacaaaa acaaaaaact gcagtgaaag     3960
acaagctgca aatcagccat gtgctgcgtg cctgtggaat ctggagtgag gggtaaaagc    4020
tgatctggtt tgactccgct ggaggtgggg cctggagcag gccttgcgct gttgcgtaac    4080
tggctgtgtt ctggtgaggc cttgctccca accccacacg ctcctccctc tgaggctgta    4140
ggactcgcag tcaggggcag ctgaccatgg aagattgaga gcccaaggtt taaacttctc    4200
tgaagggagg tggggatgag aagaggggtt tttttgtact ttgtacaaag accacacatt    4260
tgtgtaaaca gtgttttgga ataaaatatt tttttcat                             4298
```

<210> SEQ ID NO 25
<211> LENGTH: 794
<212> TYPE: PRT
<213> ORGANISM: Homo sapiens

<400> SEQUENCE: 25

```
Met Ala Gly Trp Ile Gln Ala Gln Gln Leu Gln Gly Asp Ala Leu Arg
1               5                   10                  15

Gln Met Gln Val Leu Tyr Gly Gln His Phe Pro Ile Glu Val Arg His
            20                  25                  30

Tyr Leu Ala Gln Trp Ile Glu Ser Gln Pro Trp Asp Ala Ile Asp Leu
        35                  40                  45

Asp Asn Pro Gln Asp Arg Ala Gln Ala Thr Gln Leu Leu Glu Gly Leu
    50                  55                  60

Val Gln Glu Leu Gln Lys Lys Ala Glu His Gln Val Gly Glu Asp Gly
65                  70                  75                  80

Phe Leu Leu Lys Ile Lys Leu Gly His Tyr Ala Thr Gln Leu Gln Lys
                85                  90                  95

Thr Tyr Asp Arg Cys Pro Leu Glu Leu Val Arg Cys Ile Arg His Ile
            100                 105                 110

Leu Tyr Asn Glu Gln Arg Leu Val Arg Glu Ala Asn Asn Cys Ser Ser
        115                 120                 125

Pro Ala Gly Ile Leu Val Asp Ala Met Ser Gln Lys His Leu Gln Ile
    130                 135                 140

Asn Gln Thr Phe Glu Glu Leu Arg Leu Val Thr Gln Asp Thr Glu Asn
145                 150                 155                 160

Glu Leu Lys Lys Leu Gln Gln Thr Gln Glu Tyr Phe Ile Ile Gln Tyr
                165                 170                 175

Gln Glu Ser Leu Arg Ile Gln Ala Gln Phe Ala Gln Leu Ala Gln Leu
            180                 185                 190

Ser Pro Gln Glu Arg Leu Ser Arg Glu Thr Ala Leu Gln Gln Lys Gln
        195                 200                 205

Val Ser Leu Glu Ala Trp Leu Gln Arg Glu Ala Gln Thr Leu Gln Gln
    210                 215                 220

Tyr Arg Val Glu Leu Ala Glu Lys His Gln Lys Thr Leu Gln Leu Leu
225                 230                 235                 240

Arg Lys Gln Gln Thr Ile Ile Leu Asp Asp Glu Leu Ile Gln Trp Lys
                245                 250                 255
```

```
Arg Arg Gln Gln Leu Ala Gly Asn Gly Gly Pro Pro Glu Gly Ser Leu
            260                 265                 270

Asp Val Leu Gln Ser Trp Cys Glu Lys Leu Ala Glu Ile Ile Trp Gln
            275                 280                 285

Asn Arg Gln Gln Ile Arg Arg Ala Glu His Leu Cys Gln Gln Leu Pro
            290                 295                 300

Ile Pro Gly Pro Val Glu Glu Met Leu Ala Glu Val Asn Ala Thr Ile
305                 310                 315                 320

Thr Asp Ile Ile Ser Ala Leu Val Thr Ser Thr Phe Ile Ile Glu Lys
                325                 330                 335

Gln Pro Pro Gln Val Leu Lys Thr Gln Thr Lys Phe Ala Ala Thr Val
            340                 345                 350

Arg Leu Leu Val Gly Gly Lys Leu Asn Val His Met Asn Pro Pro Gln
            355                 360                 365

Val Lys Ala Thr Ile Ile Ser Glu Gln Gln Ala Lys Ser Leu Leu Lys
            370                 375                 380

Asn Glu Asn Thr Arg Asn Glu Cys Ser Gly Glu Ile Leu Asn Asn Cys
385                 390                 395                 400

Cys Val Met Glu Tyr His Gln Ala Thr Gly Thr Leu Ser Ala His Phe
                405                 410                 415

Arg Asn Met Ser Leu Lys Arg Ile Lys Arg Ala Asp Arg Arg Gly Ala
            420                 425                 430

Glu Ser Val Thr Glu Glu Lys Phe Thr Val Leu Phe Glu Ser Gln Phe
            435                 440                 445

Ser Val Gly Ser Asn Glu Leu Val Phe Gln Val Lys Thr Leu Ser Leu
            450                 455                 460

Pro Val Val Val Ile Val His Gly Ser Gln Asp His Asn Ala Thr Ala
465                 470                 475                 480

Thr Val Leu Trp Asp Asn Ala Phe Ala Glu Pro Gly Arg Val Pro Phe
                485                 490                 495

Ala Val Pro Asp Lys Val Leu Trp Pro Gln Leu Cys Glu Ala Leu Asn
            500                 505                 510

Met Lys Phe Lys Ala Glu Val Gln Ser Asn Arg Gly Leu Thr Lys Glu
            515                 520                 525

Asn Leu Val Phe Leu Ala Gln Lys Leu Phe Asn Asn Ser Ser Ser His
530                 535                 540

Leu Glu Asp Tyr Ser Gly Leu Ser Val Ser Trp Ser Gln Phe Asn Arg
545                 550                 555                 560

Glu Asn Leu Pro Gly Trp Asn Tyr Thr Phe Trp Gln Trp Phe Asp Gly
            565                 570                 575

Val Met Glu Val Leu Lys Lys His His Lys Pro His Trp Asn Asp Gly
            580                 585                 590

Ala Ile Leu Gly Phe Val Asn Lys Gln Gln Ala His Asp Leu Leu Ile
            595                 600                 605

Asn Lys Pro Asp Gly Thr Phe Leu Leu Arg Phe Ser Asp Ser Glu Ile
            610                 615                 620

Gly Gly Ile Thr Ile Ala Trp Lys Phe Asp Ser Pro Glu Arg Asn Leu
625                 630                 635                 640

Trp Asn Leu Lys Pro Phe Thr Thr Arg Asp Phe Ser Ile Arg Ser Leu
                645                 650                 655

Ala Asp Arg Leu Gly Asp Leu Ser Tyr Leu Ile Tyr Val Phe Pro Asp
            660                 665                 670

Arg Pro Lys Asp Glu Val Phe Ser Lys Tyr Tyr Thr Pro Val Leu Ala
            675                 680                 685
```

```
Lys Ala Val Asp Gly Tyr Val Lys Pro Gln Ile Lys Gln Val Val Pro
    690             695                 700

Glu Phe Val Asn Ala Ser Ala Asp Ala Gly Gly Ser Ser Ala Thr Tyr
705             710                 715                 720

Met Asp Gln Ala Pro Ser Pro Ala Val Cys Pro Gln Ala Pro Tyr Asn
            725                 730                 735

Met Tyr Pro Gln Asn Pro Asp His Val Leu Asp Gln Asp Gly Glu Phe
                740                 745                 750

Asp Leu Asp Glu Thr Met Asp Val Ala Arg His Val Glu Glu Leu Leu
            755                 760                 765

Arg Arg Pro Met Asp Ser Leu Asp Ser Arg Leu Ser Pro Pro Ala Gly
        770                 775                 780

Leu Phe Thr Ser Ala Arg Gly Ser Leu Ser
785                 790

<210> SEQ ID NO 26
<211> LENGTH: 60
<212> TYPE: DNA
<213> ORGANISM: Homo sapiens

<400> SEQUENCE: 26
tctctgtttg taaccttgtc gacaaagagg tagaaaagat tgggtctagg atatggtggg     60

<210> SEQ ID NO 27
<211> LENGTH: 4025
<212> TYPE: DNA
<213> ORGANISM: Homo sapiens

<400> SEQUENCE: 27
cccggctctg cccgcccttc gaaagtccag ggtccctgcc cgctaggcaa gttgcactca     60
tggcacctcc aagtgaagag cgcccctga tccctcagcg ttcatgcagc ctcttgtcca    120
cggaggctgg tgcctgcat gtgctgctgc ccgctcgggg ccccgggccc cccagcgcc    180 tatctttctc ctttggggac acttggctg aggacctgtg cgtgcaggct gccaaggcca    240
gcggcatcct gcctgtgtac cactccctct ttgctctggc cacggaggac ctgtcctgct    300
ggttcccccc gagccacatc ttctccgtgg aggatgccag cacccaagtc ctgctgtaca    360
ggattcgctt ttacttcccc aattggtttg ggctggagaa gtgccaccgc ttcgggctac    420
gcaaggattt ggccagtgct atccttgacc tgccagtcct ggagcacctc tttgcccagc    480
accgcagtga cctggtgagt gggcgcctcc ccgtgggcct cagtctcaag gagcagggtg    540
agtgtctcag cctggccgtg ttggacctgg cccggatggc gcgagagcag gcccagcggc    600
cgggagagct gctgaagact gtcagctaca aggcctgcct acccccaagc ctgcgcgacc    660
tgatccaggg cctgagcttc gtgacgcgga ggcgtattcg gaggacggtg cgcagagccc    720
tgcgccgcgt ggccgcctgc caggcagacc ggcactcgct catggccaag tacatcatgg    780
acctggagcg gctggatcca gccggggccg ccgagacctt ccacgtgggc ctccctgggg    840
cccttggtgg ccacgacggg ctgggctgc tccgcgtggc tggtgacggc ggcatcgcct    900
ggacccaggg agaacaggag gtcctccagc ccttctgcga ctttccagaa atcgtagaca    960
ttagcatcaa gcaggcccg cgcgttggcc cggccggaga gcaccgcctg gtcactgtta   1020
ccaggacaga caaccagatt ttagaggccg agttcccagg gctgcccgag gctctgtcgt   1080
tcgtggcgct cgtggacggc tacttccggc tgaccacgga ctcccagcac ttcttctgca   1140
aggaggtggc caccgccgagg ctgctggagg aagtggccga gcagtgccac ggccccatca   1200
```

```
ctctggactt tgccatcaac aagctcaaga ctgggggctc acgtcctggc tcctatgttc    1260
tccgccgcag ccccccaggac tttgacagct tcctcctcac tgtctgtgtc cagaaccccc    1320
ttggtcctga ttataagggc tgcctcatcc ggcgcagccc cacaggaacc ttccttctgg    1380
ttggcctcag ccgaccccac agcagtcttc gagagctcct ggcaacctgc tgggatgggg    1440
ggctgcacgt agatggggtg gcagtgaccc tcacttcctg ctgtatcccc agacccaaag    1500
aaaagtccaa cctgatcgtg gtccagagag gtcacagccc acccacatca tccttggttc    1560
agccccaatc ccaataccag ctgagtcaga tgacatttca caagatccct gctgacagcc    1620
tggagtggca tgagaacctg ggccatgggt ccttcaccaa gatttaccgg ggctgtcgcc    1680
atgaggtggt ggatggggag gcccgaaaga cagaggtgct gctgaaggtc atggatgcca    1740
agcacaagaa ctgcatggag tcattcctgg aagcagcgag cttgatgagc caagtgtcgt    1800
accggcatct cgtgctgctc cacggcgtgt gcatggctgg agacagcacc atggtgcagg    1860
aatttgtaca cctgggggcc atagacatgt atctgcgaaa acgtgccac ctggtgccag    1920
ccagctggaa gctgcaggtg gtcaaacagc tggcctacgc cctcaactat ctggaggaca    1980
aaggcctgcc ccatggcaat gtctctgccc ggaaggtgct cctggctcgg agggggctg    2040
atgggagccc gcccttcatc aagctgagtg accctgggt cagccccgct gtgttaagcc    2100
tggagatgct caccgacagg atccctggg tggcccccga gtgtctccgg gaggcgcaga    2160
cacttagctt ggaagctgac aagtggggct tcggcgccac ggtctgggaa gtgtttagtg    2220
gcgtcaccat gcccatcagt gccctggatc ctgctaagaa actccaattt tatgaggacc    2280
ggcagcagct gccggccccc aagtggacag agctggccct gctgattcaa cagtgcatgg    2340
cctatgagcc ggtccagagg ccctccttcc gagccgtcat tcgtgacctc aatagcctca    2400
tctcttcaga ctatgagctc ctctcagacc ccacacctgg tgccctggca cctcgtgatg    2460
ggctgtggaa tggtcccag ctctatgcct ccaagaccc cacgatcttc gaggagagac    2520
acctcaagta catctcacag ctgggcaagg gcaactttgg cagcgtggag ctgtgccgct    2580
atgacccgct aggcgacaat acaggtgccc tggtggccgt gaaacagctg cagcacagcg    2640
ggccagacca gcagagggac tttcagcggg agattcagat cctcaaagca ctgcacagtg    2700
atttcattgt caagtatcgt ggtgtcagct atggcccggg ccgccagagc ctgcggctgg    2760
tcatggagta cctgcccagc ggctgcttgc gcgacttcct gcagcggcac cgcgcgcgcc    2820
tcgatgccag ccgcctcctt ctctattcct cgcagatctg caagggcatg gagtacctgg    2880
gctcccgccg ctgcgtgcac cgcgacctgg ccgcccgaaa catcctcgtg gagagcgagg    2940
cacacgtcaa gatcgctgac ttcggcctag ctaagctgct gccgcttgac aaagactact    3000
acgtggtccg cgagccaggc cagagcccca ttttctggta tgcccccgaa tccctctcgg    3060
acaacatctt ctctcgccag tcagacgtct ggagcttcgg ggtcgtcctg tacgagctct    3120
tcacctactg cgacaaaagc tgcagccccct cggccgagtt cctgcggatg atgggatgtg    3180
agcgggatgt ccccgcccctc tgccgcctct tggaactgct ggaggagggc cagaggctgc    3240
cggcgcctcc tgcctgccct gctgaggttc acgagctcat gaagctgtgc tgggcccccta    3300
gcccacagga ccggccatca ttcagcgccc tgggcccccca gctggacatg ctgtggagcg    3360
gaagccgggg gtgtgagact catgccttca ctgctcaccc agagggcaaa caccactccc    3420
tgtccttttc atagctcctg cccgcagacc tctggattag gtctctgttg actggctgtg    3480
tgaccttagg cccggagctg cccctctctg ggcctcagag gccttatgag ggtcctctac    3540
ttcaggaaca cccccatgac attgcatttg gggggggctcc cgtggcctgt agaatagcct    3600
```

-continued

```
gtggcctttg caatttgtta aggttcaaga cagatgggca tatgtgtcag tggggctctc    3660
tgagtcctgg cccaaagaag caaggaacca aatttaagac tctcgcatct tcccaacccc    3720
ttaagccctg gcccctgag tttccttttc tgtctctctc tttttatttt ttttattttt     3780 attttattt ttgagacaga gcctcgctct gttacccagg gtggagtgca gtggtgcgat     3840
ctcggctcag tgcaacctct gcttcccagg ttcaagcgat tctcctgcct cagcctcccg    3900
agtagctggg attacaggtg tgcaccacca cacccggcta ttttttttta tttttaatag    3960
agatgaggtt tcaccatgat ggccaggctg atctcgaact cctaacctca agtgatcctc    4020
ccacc                                                                4025
```

<210> SEQ ID NO 28
<211> LENGTH: 1124
<212> TYPE: PRT
<213> ORGANISM: Homo sapiens

<400> SEQUENCE: 28

```
Met Ala Pro Pro Ser Glu Glu Thr Pro Leu Ile Pro Gln Arg Ser Cys
  1               5                  10                  15

Ser Leu Leu Ser Thr Glu Ala Gly Ala Leu His Val Leu Leu Pro Ala
             20                  25                  30

Arg Gly Pro Gly Pro Pro Gln Arg Leu Ser Phe Ser Phe Gly Asp His
         35                  40                  45

Leu Ala Glu Asp Leu Cys Val Gln Ala Ala Lys Ala Ser Gly Ile Leu
     50                  55                  60

Pro Val Tyr His Ser Leu Phe Ala Leu Ala Thr Glu Asp Leu Ser Cys
 65                  70                  75                  80

Trp Phe Pro Pro Ser His Ile Phe Ser Val Glu Asp Ala Ser Thr Gln
                 85                  90                  95

Val Leu Leu Tyr Arg Ile Arg Phe Tyr Phe Pro Asn Trp Phe Gly Leu
            100                 105                 110

Glu Lys Cys His Arg Phe Gly Leu Arg Lys Asp Leu Ala Ser Ala Ile
        115                 120                 125

Leu Asp Leu Pro Val Leu Glu His Leu Phe Ala Gln His Arg Ser Asp
    130                 135                 140

Leu Val Ser Gly Arg Leu Pro Val Gly Leu Ser Leu Lys Glu Gln Gly
145                 150                 155                 160

Glu Cys Leu Ser Leu Ala Val Leu Asp Leu Ala Arg Met Ala Arg Glu
                165                 170                 175

Gln Ala Gln Arg Pro Gly Glu Leu Leu Lys Thr Val Ser Tyr Lys Ala
            180                 185                 190

Cys Leu Pro Pro Ser Leu Arg Asp Leu Ile Gln Gly Leu Ser Phe Val
        195                 200                 205

Thr Arg Arg Arg Ile Arg Arg Thr Val Arg Arg Ala Leu Arg Arg Val
    210                 215                 220

Ala Ala Cys Gln Ala Asp Arg His Ser Leu Met Ala Lys Tyr Ile Met
225                 230                 235                 240

Asp Leu Glu Arg Leu Asp Pro Ala Gly Ala Ala Glu Thr Phe His Val
                245                 250                 255

Gly Leu Pro Gly Ala Leu Gly Gly His Asp Gly Leu Gly Leu Leu Arg
            260                 265                 270

Val Ala Gly Asp Gly Gly Ile Ala Trp Thr Gln Gly Glu Gln Glu Val
        275                 280                 285

Leu Gln Pro Phe Cys Asp Phe Pro Glu Ile Val Asp Ile Ser Ile Lys
    290                 295                 300
```

```
Gln Ala Pro Arg Val Gly Pro Ala Gly Glu His Arg Leu Val Thr Val
305                 310                 315                 320

Thr Arg Thr Asp Asn Gln Ile Leu Glu Ala Glu Phe Pro Gly Leu Pro
            325                 330                 335

Glu Ala Leu Ser Phe Val Ala Leu Val Asp Gly Tyr Phe Arg Leu Thr
                340                 345                 350

Thr Asp Ser Gln His Phe Phe Cys Lys Glu Val Ala Pro Pro Arg Leu
            355                 360                 365

Leu Glu Glu Val Ala Glu Gln Cys His Gly Pro Ile Thr Leu Asp Phe
370                 375                 380

Ala Ile Asn Lys Leu Lys Thr Gly Gly Ser Arg Pro Gly Ser Tyr Val
385                 390                 395                 400

Leu Arg Arg Ser Pro Gln Asp Phe Asp Ser Phe Leu Leu Thr Val Cys
                405                 410                 415

Val Gln Asn Pro Leu Gly Pro Asp Tyr Lys Gly Cys Leu Ile Arg Arg
            420                 425                 430

Ser Pro Thr Gly Thr Phe Leu Leu Val Gly Leu Ser Arg Pro His Ser
            435                 440                 445

Ser Leu Arg Glu Leu Leu Ala Thr Cys Trp Asp Gly Gly Leu His Val
450                 455                 460

Asp Gly Val Ala Val Thr Leu Thr Ser Cys Cys Ile Pro Arg Pro Lys
465                 470                 475                 480

Glu Lys Ser Asn Leu Ile Val Val Gln Arg Gly His Ser Pro Pro Thr
                485                 490                 495

Ser Ser Leu Val Gln Pro Gln Ser Gln Tyr Gln Leu Ser Gln Met Thr
                500                 505                 510

Phe His Lys Ile Pro Ala Asp Ser Leu Glu Trp His Glu Asn Leu Gly
            515                 520                 525

His Gly Ser Phe Thr Lys Ile Tyr Arg Gly Cys Arg His Glu Val Val
530                 535                 540

Asp Gly Glu Ala Arg Lys Thr Glu Val Leu Leu Lys Val Met Asp Ala
545                 550                 555                 560

Lys His Lys Asn Cys Met Glu Ser Phe Leu Glu Ala Ala Ser Leu Met
                565                 570                 575

Ser Gln Val Ser Tyr Arg His Leu Val Leu Leu His Gly Val Cys Met
            580                 585                 590

Ala Gly Asp Ser Thr Met Val Gln Glu Phe Val His Leu Gly Ala Ile
            595                 600                 605

Asp Met Tyr Leu Arg Lys Arg Gly His Leu Val Pro Ala Ser Trp Lys
610                 615                 620

Leu Gln Val Val Lys Gln Leu Ala Tyr Ala Leu Asn Tyr Leu Glu Asp
625                 630                 635                 640

Lys Gly Leu Pro His Gly Asn Val Ser Ala Arg Lys Val Leu Leu Ala
                645                 650                 655

Arg Glu Gly Ala Asp Gly Ser Pro Pro Phe Ile Lys Leu Ser Asp Pro
            660                 665                 670

Gly Val Ser Pro Ala Val Leu Ser Leu Glu Met Leu Thr Asp Arg Ile
            675                 680                 685

Pro Trp Val Ala Pro Glu Cys Leu Arg Glu Ala Gln Thr Leu Ser Leu
            690                 695                 700

Glu Ala Asp Lys Trp Gly Phe Gly Ala Thr Val Trp Glu Val Phe Ser
705                 710                 715                 720

Gly Val Thr Met Pro Ile Ser Ala Leu Asp Pro Ala Lys Lys Leu Gln
```

```
                725                 730                 735
Phe Tyr Glu Asp Arg Gln Gln Leu Pro Ala Pro Lys Trp Thr Glu Leu
            740                 745                 750

Ala Leu Leu Ile Gln Gln Cys Met Ala Tyr Glu Pro Val Gln Arg Pro
            755                 760                 765

Ser Phe Arg Ala Val Ile Arg Asp Leu Asn Ser Leu Ile Ser Ser Asp
            770                 775                 780

Tyr Glu Leu Leu Ser Asp Pro Thr Pro Gly Ala Leu Ala Pro Arg Asp
785                 790                 795                 800

Gly Leu Trp Asn Gly Ala Gln Leu Tyr Ala Cys Gln Asp Pro Thr Ile
                805                 810                 815

Phe Glu Glu Arg His Leu Lys Tyr Ile Ser Gln Leu Gly Lys Gly Asn
            820                 825                 830

Phe Gly Ser Val Glu Leu Cys Arg Tyr Asp Pro Leu Gly Asp Asn Thr
            835                 840                 845

Gly Ala Leu Val Ala Val Lys Gln Leu Gln His Ser Gly Pro Asp Gln
            850                 855                 860

Gln Arg Asp Phe Gln Arg Glu Ile Gln Ile Leu Lys Ala Leu His Ser
865                 870                 875                 880

Asp Phe Ile Val Lys Tyr Arg Gly Val Ser Tyr Gly Pro Gly Arg Gln
                885                 890                 895

Ser Leu Arg Leu Val Met Glu Tyr Leu Pro Ser Gly Cys Leu Arg Asp
            900                 905                 910

Phe Leu Gln Arg His Arg Ala Arg Leu Asp Ala Ser Arg Leu Leu Leu
            915                 920                 925

Tyr Ser Ser Gln Ile Cys Lys Gly Met Glu Tyr Leu Gly Ser Arg Arg
            930                 935                 940

Cys Val His Arg Asp Leu Ala Ala Arg Asn Ile Leu Val Glu Ser Glu
945                 950                 955                 960

Ala His Val Lys Ile Ala Asp Phe Gly Leu Ala Lys Leu Leu Pro Leu
                965                 970                 975

Asp Lys Asp Tyr Tyr Val Val Arg Glu Pro Gly Gln Ser Pro Ile Phe
            980                 985                 990

Trp Tyr Ala Pro Glu Ser Leu Ser Asp Asn Ile Phe Ser Arg Gln Ser
            995                 1000                1005

Asp Val Trp Ser Phe Gly Val Val Leu Tyr Glu Leu Phe Thr Tyr Cys
            1010                1015                1020

Asp Lys Ser Cys Ser Pro Ser Ala Glu Phe Leu Arg Met Met Gly Cys
1025                1030                1035                1040

Glu Arg Asp Val Pro Ala Leu Cys Arg Leu Leu Glu Leu Leu Glu Glu
            1045                1050                1055

Gly Gln Arg Leu Pro Ala Pro Ala Cys Pro Ala Glu Val His Glu
            1060                1065                1070

Leu Met Lys Leu Cys Trp Ala Pro Ser Pro Gln Asp Arg Pro Ser Phe
            1075                1080                1085

Ser Ala Leu Gly Pro Gln Leu Asp Met Leu Trp Ser Gly Ser Arg Gly
            1090                1095                1100

Cys Glu Thr His Ala Phe Thr Ala His Pro Glu Gly Lys His His Ser
1105                1110                1115                1120

Leu Ser Phe Ser

<210> SEQ ID NO 29
<211> LENGTH: 60
<212> TYPE: DNA
```

<213> ORGANISM: Homo sapiens

<400> SEQUENCE: 29

```
cgcatcttcc caaccccttta agccctggcc ccctgagttt ccttttctcg tctctctctt      60
```

<210> SEQ ID NO 30
<211> LENGTH: 4451
<212> TYPE: DNA
<213> ORGANISM: Homo sapiens

<400> SEQUENCE: 30

```
gctcatacta gggacgggaa gtcgcgacca gagccattgg agggcgcggg gactgcaacc      60
ctaatcagca gagcccaaat ggcgcagtgg gaaatgctgc agaatcttga cagccccttt     120
caggatcagc tgcaccagct ttactcgcac agcctcctgc ctgtggacat tcgacagtac     180
ttggctgtct ggattgaaga ccagaactgg caggaagctg cacttgggag tgatgattcc     240
aaggctacca tgctattctt ccacttcttg gatcagctga actatgagtg tggccgttgc     300
agccaggacc cagagtcctt gttgctgcag cacaatttgc ggaaattctg ccgggacatt     360
cagcccttttt cccaggatcc tacccagttg gctgagatga tctttaacct ccttctggaa     420
gaaaaaagaa ttttgatcca ggctcagagg gcccaattgg aacaaggaga gccagttctc     480
gaaacacctg tggagagcca gcaacatgag attgaatccc ggatcctgga tttaagggct     540
atgatggaga agctggtaaa atccatcagc caactgaaag accagcagga tgtcttctgc     600
ttccgatata gatccaggc caaagggaag acaccctctc tggaccccca tcagaccaaa     660
gagcagaaga ttctgcagga aactctcaat gaactggaca aaaggagaaa ggaggtgctg     720
gatgcctcca agcactgct aggccgatta actaccctaa tcgagctact gctgccaaag     780
ttggaggagt ggaaggccca gcagcaaaaa gcctgcatca gagctcccat tgaccacggg     840
ttggaacagc tggagacatg gttcacagct ggagcaaagc tgttgtttca cctgaggcag     900
ctgctgaagg agctgaaggg actgagttgc ctggttagct atcaggatga ccctctgacc     960
aaagggggtgg acctacgcaa cgcccaggtc acagagttgc tacagcgtct gctccacaga    1020
gcctttgtgg tagaaaccca gccctgcatg ccccaaactc ccatcgacc cctcatcctc    1080
aagactggca gcaagttcac cgtccgaaca aggctgctgg tgagactcca ggaaggcaat    1140
gagtcactga ctgtggaagt ctccattgac aggaatcctc tcaattaca aggcttccgg    1200
aagttcaaca ttctgacttc aaaccagaaa actttgaccc ccgagaaggg gcagagtcag    1260
ggtttgattt gggactttgg ttacctgact ctggtggagc aacgttcagg tggttcagga    1320
aagggcagca ataaggggcc actaggtgtg acagaggaac tgcacatcat cagcttcacg    1380
gtcaaatata cctaccaggg tctgaagcag gagctgaaaa cggacaccct ccctgtggtg    1440
attatttcca acatgaacca gctctcaatt gcctgggctt cagttctctg gttcaatttg    1500
ctcagcccaa accttcagaa ccagcagttc ttctccaacc cccccaaggc cccctggagc    1560
ttgctgggcc ctgctctcag ttggcagttc tcctcctatg ttggccgagg cctcaactca    1620
gaccagctga gcatgctgag aaacaagctg ttcgggcaga actgtaggac tgaggatcca    1680
ttattgtcct gggctgactt cactaagcga gagagccctc ctggcaagtt accattctgg    1740
acatggctgg acaaaattct ggagttggta catgaccacc tgaaggatct ctggaatgat    1800
ggacgcatca tgggctttgt gagtcggagc caggagcgcc ggctgctgaa gaagaccatg    1860
tctggcacct ttctactgcg cttcagtgaa tcgtcagaag ggggcattac ctgctcctgg    1920
gtggagcacc aggatgatga caaggtgctc atctactctg tgcaaccgta cacgaaggag    1980
```

```
gtgctgcagt cactcccgct gactgaaatc atccgccatt accagttgct cactgaggag    2040
aatatacctg aaaacccact gcgcttcctc tatccccgaa tcccccggga tgaagctttt    2100
gggtgctact accaggagaa agttaatctc caggaacgga ggaaatacct gaaacacagg    2160
ctcattgtgg tctctaatag acaggtggat gaactgcaac aaccgctgga gcttaagcca    2220
gagccagagc tggagtcatt agagctggaa ctagggctgg tgccagagcc agagctcagc    2280
ctggacttag agccactgct gaaggcaggg ctggatctgg ggccagagct agagtctgtg    2340
ctggagtcca ctctggagcc tgtgatagag cccacactat gcatggtatc acaaacagtg    2400
ccagagccag accaaggacc tgtatcacag ccagtgccag agccagattt gccctgtgat    2460
ctgagacatt tgaacactga gccaatggaa atcttcagaa actgtgtaaa gattgaagaa    2520
atcatgccga atggtgaccc actgttggct ggccagaaca ccgtggatga ggtttacgtc    2580
tcccgcccca gccacttcta cactgatgga cccttgatgc cttctgactt ctaggaacca    2640
catttcctct gttcttttca tatctcttgc ccttcctact cctcatagca tgatattgtt    2700
ctccaaggat gggaatcagg catgtgtccc ttccaagctg tgttaactgt tcaaactcag    2760
gcctgtgtga ctccattggg gtgagaggtg aaagcataac atgggtacag aggggacaac    2820
aatgaatcag aacagatgct gagccatagg tctaaatagg atcctggagg ctgcctgctg    2880
tgctgggagg tataggggtc ctgggggcag gccaggcag ttgacaggta cttggagggc     2940
tcagggcagt ggcttctttc cagtatggaa ggatttcaac attttaatag ttggttaggc    3000
taaactggtg catactggca ttggcccttg gtggggagca cagacacagg ataggactcc    3060
atttctttct tccattcctt catgtctagg ataacttgct ttcttctttc ctttactcct    3120
ggctcaagcc ctgaatttct tcttttcctg caggggttga gagctttctg ccttagccta    3180
ccatgtgaaa ctctaccctg aagaaaggga tggataggaa gtagacctct ttttcttacc    3240
agtctcctcc cctactctgc ccctaagctg gctgtacctg ttcctcccccc ataaaatgat    3300 cctgccaatc taatgtgagt gtgaagcttt gcacactagt ttatgctacc tagtctccac    3360
tttctcaatg cttaggagac agatcactcc tggaggctgg ggatggtagg attgctgggg    3420
attttttttt ttttaaacag ggtctcactc tgttgcccag gctagagtgc aatggtgcaa    3480
tcacagctca ctgcagcctc aacctcctgg gttcaagcaa tcctcctacc tcagcctcct    3540
gggtagctag caccatggca tgcgccacca tgccctattt ttttttttta aagacagggt    3600
cttgctatat tgcccaggct ggtcttgaac tgggctcaag tgatcctcac gccttggcct    3660
cccaaagtgc tgggattata ggcatgagcc actgtgcttg gccaggattt tttttttttt    3720
ttttttgaga tggagtttct ctcttgttgt ccaggctgga gtgcaatggt gtgatctcgg    3780
ctcactgcaa cctccgcctt ccgggttcaa gtgactctcc tgcctcagcc tcccagtag    3840 ctgggattac agatctgcac caccatgccc agctaatttt gtattttag tagagacggg     3900 gtttctccat gttggtcagg ctggtctcga actcctgacc tcaagtgatc tgtccacctc    3960
ggcctcccag agtgctggga ttacaggcgt gagccactgt cccagcagg aatttctttt     4020 ttatagtatt ggataaagtt tggtgttttt acagaggaga agcaatgggt cttagctctt    4080
tctctattat gttatcatcc tccctttttt gtacaatatg ttgtttacct gaaaggaagg    4140
tttctattcg ttggttgtgg acctggacaa agtccaagtc tgtggaactt aaaaccttga    4200
aggtctgtca taggactctg gacaatctca caccttagct attcccaggg aaccccaggg    4260
ggcaactgac attgctccaa gatgttctcc tgatgtagct tgagatataa aggaaaggcc    4320
ctgcacaggt ggctgttttct tgtctgttat gtcagaggaa cagtcctgtt cagaaagggg    4380
```

```
ctcttctgag cagaaatggc taataaactt tgtgctgatc tggaaaaaaa aaaaaaaaaa      4440
aaaaaaaaaa a                                                          4451
```

<210> SEQ ID NO 31
<211> LENGTH: 851
<212> TYPE: PRT
<213> ORGANISM: Homo sapiens

<400> SEQUENCE: 31

```
Met Ala Gln Trp Glu Met Leu Gln Asn Leu Asp Ser Pro Phe Gln Asp
1               5                   10                  15

Gln Leu His Gln Leu Tyr Ser His Ser Leu Leu Pro Val Asp Ile Arg
            20                  25                  30

Gln Tyr Leu Ala Val Trp Ile Glu Asp Gln Asn Trp Gln Glu Ala Ala
        35                  40                  45

Leu Gly Ser Asp Asp Ser Lys Ala Thr Met Leu Phe Phe His Phe Leu
    50                  55                  60

Asp Gln Leu Asn Tyr Glu Cys Gly Arg Cys Ser Gln Asp Pro Glu Ser
65                  70                  75                  80

Leu Leu Leu Gln His Asn Leu Arg Lys Phe Cys Arg Asp Ile Gln Pro
                85                  90                  95

Phe Ser Gln Asp Pro Thr Gln Leu Ala Glu Met Ile Phe Asn Leu Leu
            100                 105                 110

Leu Glu Glu Lys Arg Ile Leu Ile Gln Ala Gln Arg Ala Gln Leu Glu
        115                 120                 125

Gln Gly Glu Pro Val Leu Glu Thr Pro Val Glu Ser Gln Gln His Glu
    130                 135                 140

Ile Glu Ser Arg Ile Leu Asp Leu Arg Ala Met Met Glu Lys Leu Val
145                 150                 155                 160

Lys Ser Ile Ser Gln Leu Lys Asp Gln Gln Asp Val Phe Cys Phe Arg
                165                 170                 175

Tyr Lys Ile Gln Ala Lys Gly Lys Thr Pro Ser Leu Asp Pro His Gln
            180                 185                 190

Thr Lys Glu Gln Lys Ile Leu Gln Glu Thr Leu Asn Glu Leu Asp Lys
        195                 200                 205

Arg Arg Lys Glu Val Leu Asp Ala Ser Lys Ala Leu Leu Gly Arg Leu
    210                 215                 220

Thr Thr Leu Ile Glu Leu Leu Pro Lys Leu Glu Glu Trp Lys Ala
225                 230                 235                 240

Gln Gln Gln Lys Ala Cys Ile Arg Ala Pro Ile Asp His Gly Leu Glu
                245                 250                 255

Gln Leu Glu Thr Trp Phe Thr Ala Gly Ala Lys Leu Leu Phe His Leu
            260                 265                 270

Arg Gln Leu Leu Lys Glu Leu Lys Gly Leu Ser Cys Leu Val Ser Tyr
        275                 280                 285

Gln Asp Asp Pro Leu Thr Lys Gly Val Asp Leu Arg Asn Ala Gln Val
    290                 295                 300

Thr Glu Leu Leu Gln Arg Leu His Arg Ala Phe Val Val Glu Thr
305                 310                 315                 320

Gln Pro Cys Met Pro Gln Thr Pro His Arg Pro Leu Ile Leu Lys Thr
                325                 330                 335

Gly Ser Lys Phe Thr Val Arg Thr Arg Leu Leu Val Arg Leu Gln Glu
            340                 345                 350

Gly Asn Glu Ser Leu Thr Val Glu Val Ser Ile Asp Arg Asn Pro Pro
        355                 360                 365
```

```
Gln Leu Gln Gly Phe Arg Lys Phe Asn Ile Leu Thr Ser Asn Gln Lys
    370                 375                 380

Thr Leu Thr Pro Glu Lys Gly Gln Ser Gln Gly Leu Ile Trp Asp Phe
385                 390                 395                 400

Gly Tyr Leu Thr Leu Val Glu Gln Arg Ser Gly Ser Gly Lys Gly
                405                 410                 415

Ser Asn Lys Gly Pro Leu Gly Val Thr Glu Glu Leu His Ile Ile Ser
            420                 425                 430

Phe Thr Val Lys Tyr Thr Tyr Gln Gly Leu Lys Gln Glu Leu Lys Thr
        435                 440                 445

Asp Thr Leu Pro Val Val Ile Ile Ser Asn Met Asn Gln Leu Ser Ile
        450                 455                 460

Ala Trp Ala Ser Val Leu Trp Phe Asn Leu Leu Ser Pro Asn Leu Gln
465                 470                 475                 480

Asn Gln Gln Phe Phe Ser Asn Pro Pro Lys Ala Pro Trp Ser Leu Leu
                485                 490                 495

Gly Pro Ala Leu Ser Trp Gln Phe Ser Ser Tyr Val Gly Arg Gly Leu
            500                 505                 510

Asn Ser Asp Gln Leu Ser Met Leu Arg Asn Lys Leu Phe Gly Gln Asn
        515                 520                 525

Cys Arg Thr Glu Asp Pro Leu Leu Ser Trp Ala Asp Phe Thr Lys Arg
        530                 535                 540

Glu Ser Pro Pro Gly Lys Leu Pro Phe Trp Thr Trp Leu Asp Lys Ile
545                 550                 555                 560

Leu Glu Leu Val His Asp His Leu Lys Asp Leu Trp Asn Asp Gly Arg
                565                 570                 575

Ile Met Gly Phe Val Ser Arg Ser Gln Glu Arg Arg Leu Leu Lys Lys
            580                 585                 590

Thr Met Ser Gly Thr Phe Leu Leu Arg Phe Ser Glu Ser Ser Glu Gly
        595                 600                 605

Gly Ile Thr Cys Ser Trp Val Glu His Gln Asp Asp Asp Lys Val Leu
        610                 615                 620

Ile Tyr Ser Val Gln Pro Tyr Thr Lys Glu Val Leu Gln Ser Leu Pro
625                 630                 635                 640

Leu Thr Glu Ile Ile Arg His Tyr Gln Leu Leu Thr Glu Glu Asn Ile
                645                 650                 655

Pro Glu Asn Pro Leu Arg Phe Leu Tyr Pro Arg Ile Pro Arg Asp Glu
            660                 665                 670

Ala Phe Gly Cys Tyr Tyr Gln Glu Lys Val Asn Leu Gln Glu Arg Arg
        675                 680                 685

Lys Tyr Leu Lys His Arg Leu Ile Val Val Ser Asn Arg Gln Val Asp
        690                 695                 700

Glu Leu Gln Gln Pro Leu Glu Leu Lys Pro Glu Pro Glu Leu Glu Ser
705                 710                 715                 720

Leu Glu Leu Glu Leu Gly Leu Val Pro Glu Pro Glu Leu Ser Leu Asp
                725                 730                 735

Leu Glu Pro Leu Leu Lys Ala Gly Leu Asp Leu Gly Pro Glu Leu Glu
            740                 745                 750

Ser Val Leu Glu Ser Thr Leu Glu Pro Val Ile Glu Pro Thr Leu Cys
        755                 760                 765

Met Val Ser Gln Thr Val Pro Glu Pro Asp Gln Gly Pro Val Ser Gln
        770                 775                 780

Pro Val Pro Glu Pro Asp Leu Pro Cys Asp Leu Arg His Leu Asn Thr
```

```
785                 790                 795                 800
Glu Pro Met Glu Ile Phe Arg Asn Cys Val Lys Ile Glu Glu Ile Met
                805                 810                 815

Pro Asn Gly Asp Pro Leu Leu Ala Gly Gln Asn Thr Val Asp Glu Val
            820                 825                 830

Tyr Val Ser Arg Pro Ser His Phe Tyr Thr Asp Gly Pro Leu Met Pro
        835                 840                 845

Ser Asp Phe
    850

<210> SEQ ID NO 32
<211> LENGTH: 60
<212> TYPE: DNA
<213> ORGANISM: Homo sapiens

<400> SEQUENCE: 32
tgaagaaagg gatggatagg aagtagacct ctttttctta ccagtctcct cccctactct     60
```